US007390937B2

(12) United States Patent
Good et al.

(10) Patent No.: US 7,390,937 B2
(45) Date of Patent: *Jun. 24, 2008

(54) PLANTS WITH ENHANCED LEVELS OF NITROGEN UTILIZATION PROTEINS IN THEIR ROOT EPIDERMIS AND USES THEREOF

(75) Inventors: Allen G. Good, Edmonton (CA); Virginia L. Stroeher, Sherbrooke (CA); Douglas G. Muench, Calgary (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 412 days.

This patent is subject to a terminal disclaimer.

(21) Appl. No.: 10/756,213

(22) Filed: Jan. 12, 2004

(65) Prior Publication Data

US 2005/0044585 A1 Feb. 24, 2005

Related U.S. Application Data

(63) Continuation-in-part of application No. 10/321,718, filed on Dec. 17, 2002, now abandoned, which is a continuation of application No. 09/568,221, filed on May 9, 2000, now abandoned, which is a continuation of application No. 08/599,968, filed on Feb. 14, 1996, now Pat. No. 6,084,153, application No. 10/756,213, which is a continuation-in-part of application No. 09/493,803, filed on Jan. 28, 2000, now abandoned.

(51) Int. Cl.
*A01H 5/00* (2006.01)
*A01H 5/10* (2006.01)
*C12N 15/82* (2006.01)

(52) U.S. Cl. ...................... 800/298; 800/287
(58) Field of Classification Search ................ None
See application file for complete search history.

(56) References Cited

U.S. PATENT DOCUMENTS

| 5,256,558 A | 10/1993 | Coruzzi et al. |
| 5,750,399 A | 5/1998 | Dixon et al. |
| 5,955,651 A * | 9/1999 | Coruzzi et al. .............. 800/298 |
| 6,084,153 A | 7/2000 | Good et al. |

FOREIGN PATENT DOCUMENTS

| AU | 17321/88 | 12/1988 |
| WO | WO 90/13633 | 11/1990 |
| WO | WO 91/04325 | 4/1991 |
| WO | WO 93/07279 | 4/1993 |
| WO | WO 95/09911 | 4/1994 |
| WO | WO 97/30163 | 8/1997 |
| WO | WO 01/55433 | 8/2001 |

OTHER PUBLICATIONS

Son et al 1992, Plant Molecular Biology 20:705-713.*
Muench et al 1994 Plant Molecular Biology 24:417-427.*
Hirel et al 1992, Plant Molecular Biology 20: 207-218.*
Edwards et al 1990, Proceedings of the National Academy of Science, USA 87: 3459-3463.*
Suzuki et al Jan. 1993, Plant Molecular Biology 21: 109-119.*
Good, A.G. et al. (1992) "Purification and characterization of an Anaerobically Induced Alanine Aminotransferase from Barley Roots." *Plant Physiol.*, 99:1520-1525.
Coruzzi, G. M. (Sep. 30, 2003). "Primary N-Assimilation Into Amino Acids in Arabidopsis," *The Arabidopsis Book*, American Society of Plant Biologists, pp. 1-17.
Good, A. G. et al. (1989). "Anaerobic Induction of Alanine Aminotransferase in Barley Root Tissue," *Plant Physiology* 90:1305-1309.
Kim. J. et al. (Jan. 2002). "Constitutive Overexpression of Cystathionine Gamma-Synthase in Arabidopsis Leads to Accumulation of Soluble Methionine and S-Methylmethionine," *Plant Physiology* 128:95-107.
Liaw, S.-H. et al. (Jun. 1993). "Feedback Inhibition of Fully Unadenylylated Glutamine Synthetase from *Salmonella typhimurium* by Glycine, Alanine, and Serine," *Proceedings of the National Academy of Sciences* 90:4996-5000.
O'Neal, T. D. et al. (1975). "Pea Leaf Glutamine Synthetase," *Plant Physiology* 55:968-974.
Tzchori, I. B.-T. et al. (Nov. 1996). "Lysine and Threonine Metabolism are Subject to Complex Patterns of Regulation in Arabidopsis," *Plant Molecular Biology* 32(4):727-734.
Wakasa, K. et al. (2006). "High-Level Tryptophan Accumulation in Seeds of Transgenic Rice and its Limited Effects on Agronomic Traits and Seed Metabolite Profile," *Journal of Experimental Botany* 57(12):3069-3078.
Montgomery, J. et al., (1993) "Identification of an Ethylene-Responsive Region in the Promoter of a Fruit Ripening Gene." Proc. Natl. Acad. Sci., vol. 90, pp. 5939-5943.
Koziel, M. G. et al. (1996) "Optimizing Expression of Transgenes with an Emphasis on Post-Transcriptional Events." Plant Molecular Biology, vol. 32, pp. 393-405.
Back et al. Plant Molecular Biology 17:9-18, 1991.

(Continued)

*Primary Examiner*—David H Kruse
(74) *Attorney, Agent, or Firm*—Morrison & Foerster LLP

(57) ABSTRACT

The present invention relates to non-naturally occurring plants that display enhanced agronomic characteristics due to elevated levels of nitrogen utilization proteins in the root of the plants. In particular, the present invention relates to non-naturally occurring plants with elevated levels of nitrogen utilization proteins specifically localized to the root epidermis of the plant. In addition, the present invention includes a preferred method of generating such non-naturally occurring plants by introducing into the plant a transgene encoding a nitrogen utilization protein operably linked to a root-epidermis-specific promoter.

20 Claims, 26 Drawing Sheets

OTHER PUBLICATIONS

Jones, Jennifer T. et al. (1995) "Developmental Expression of a Turgor-Responsive gene that Encodes an Intrinsic Membrane Protein." Plant Molecular Biology, vol. 28, No. 6, pp. 983-996.

Bohnert, Hans J. et al. "Adaptions to Environmental Stresses" Plant Call 7:1099-111 (1995).

Cheng, Chi-lien et al. "A new locus (NIA 1) in *Arabidopsis thaliana* encoding nitrate reductase" The EMBO J. 7(11):3309-14 (1988).

Cheng et al. "Differential expression of the two arabidopsis nitrate reductase genes" Plant Physiol. 96: 275-279, (1991).

Crawford, Nigel M. "Nitrate: Nutrient and Signal for Plant Growth" Plant Cell 7:859-68 (1995).

Eckes, Peter et al. "Overproduction of alfalfa glutamine synthetase in transgenic tobacco plants" Molec. Gen. Genet. 217:263-68 (1989).

Good, A.G. and Maclagan, J.L. "Effects of drought stress on the water relations in Brassica species" Can. J. Plant. Sci. 73:525-29 (1993).

Good, Allen G. and Zaplachinski, Steven T. "The effects of drought stress on free amino acid accumulation and protein synthesis in *Brassica napus*" Physiol. Plant 90:9-14 (1994).

Goodwin and Mercer, Introduction to Plant Biochemistry, 2nd Edition (Pergamon Press, New York, N.Y., 1983), Chapter 9 "Nitrogen Fixation, Amino Acid Biosynthesis and Proteins" pp. 328-361.

Hageman, R.H. and Lambert, R.J. "The Use of Physiological Traits for corn improvement" Corn and Corn Improvement, 3rd Edition (Sprague & Dudley, American Society of Agronomy, 1988) pp. 431-461.

Hanson, Andrew D. and Hitz, William D. "Metabolic Responses of Mesophytes to Plant Water Deficits" Annu. Rev. Plant Physiol. 33:163-203 (1982).

Hemon, Pascale et al. "Targeting of glutamine synthetase to the mitochondria of transgenic tobacco" Plant Mol. Blot. 15:895-904 (1990).

Hirel, Bertrand et al. "Forcing expression of a soybean root glutamine synthetase gene in tobacco leaves induces a native gene endocing cytosolic enzyme" Plant Mol. Biol. 20:207-18 (1992).

Lam, Hon-Ming et al. "Use of Arabidopsis Mutants and Genes To Study Amide Amino Acid Biosynthesis" Plant Celt 7:887-98 (1995).

Morgan, James M. "Osmoregulation and Water Stress in Higher Plants" Annu. Rev. Plant Physiol. 35:299319 (1984).

Muench, Douglas G. and Good, Allen G. "Hypoxically inducible barely alanine aminotransferase: cDNA cloning and expression analysis" Plant Mol. Biol. 24:417-27 (1994).

Peterman, T. Kaye and Goodman, Howard M. "The glutamine synthetase gene family of *Arabidopsis thaliana*: light-regulation and differential expression in leaves, roots and seeds" Mol. Gen. Genet. 230:14554(1991).

Rhodes, David et al. "Metabolic Changes Associated with Adaptation of Plant Cells to Water Stress" Plant Physiol. 82:890-903 (1986).

Sakakibara, Hitoshi et al. "Isolation and Characterization of a cDNA That Encodes Maize Glutamate Dehydrogenase" Plant Cell Physiol. 36(5):789-97 (1995).

Skriver, Karen and Mundy, John "Gene Expression in Response to Abscisic Acid and Osmotic Stress" Plant Cell 2:503-12 (1990).

Son, Daeyoung and Sugiyama, Tatsuo "Molecular cloning of an alanine aminotransferase from NAD-malic enzyme type C4 *Panicum miliaceum*" Plant. Mol. Biol. 20:705-13 (1993).

Son, Daeyoung et al. "Purification and Characterization of Alanine Aminotransferase from *Panicum miliaceum* leaves" Arch. Biochem. Biophys. 289(2):262-66 (1991).

Stewart, Cecil R. et al. "Inhibition of Proline Oxidation by Water Stress" Plant Physiol. 59:930-32 (1977).

Temple, Stephen et al. "Modulation of glutamine synthetase gene expression in tobacco by the introduction of an alfalfa glutamine synthetase gene in sense and antisense orientation: molecular and biochemical analysis" Mol Gen. Genet. 236:315-25 (1993).

Tsai, Fong-Ying and Coruzzi, Gloria M. "Dark-induced and organ-specific expression of two asparagine synthetase genes in *Pisum sativum*" The EMBO J. 9(2):323-32 (1990).

Turner, N.C. "Drought resistance and Adaption to Water Deficits in Crop Plants" Stress Physiology in Crop Plants (Harry Mussell & Richard C. Staples eds., John Wiley & Sons, New York, 1979) pp. 343-372.

Udvardi, Michael K. and Kahn, Michael L. "Isolation and analysis of a cDNA clone that encodes an alfalfa (*Medicago saliva*) aspartate aminotransferase" Mol Gen. Genet. 231:97-105 (1991).

Vanlerberge, Greg C. et al. "Anaerobic Metabolism in the N-Limited Green Alga *Selenastrum minutum*" Plant Physiol. 95:655-58 (1993).

Voetberg, Gary S. and Sharp, Robert E. "Growth of the Maize Primary Root at Low Water Potentials" Plant Physiol. 96:1125-30 (1991).

Zehnacker, Claire et al. "Purification and properties of tobacco ferredoxin-dependent glutamate synthase, and isolation of corresponding cDNA clones" Planta 187:266-74 (1992).

Stroeher, V. L. et al. "Molecular cloning and expression of a turgor-responsive gene in brassica napus" Plant Molecular Biology 27: 541-551 (1995).

Guerrero, F. D. et al. "Turgor-responsive gene transcription and RNA levels increase rapidly when pea shoots are wilted. Sequence and expression of three inducible genes" Plant Molecular Biology 15: 11-26 (1990).

Guerrero, et al. "Tissue specific expression of a plant turgor-responsive gene with amino acid sequence homology to transport-facilitating proteins" Plant Molecular Biology 21: 929-935, (1993).

Watson et al. Benjamin/Cummings, Publishing Co., Menlo Park, CA, p. 313, (1987).

Jones, Madeleine M. and Turner, Neil C. "Osmostic Adjustment of Sorghum in Response to Water Deficits" Plant Physiol. 61:122-26 (1978).

New England Biolabs 1988-1989 catalog, product #1230.

* cited by examiner

```
GTCGACCTGCAGGTCAACGGATCCTAATCGGGGTATATCCCGACCCGGAAAAAGAAACGTAGGACACGTG  -250
ACAAAACTTCATATGATCCGAGTGAATCAAGCCAAAAGGGGGATTGACACAGCTCAGCTTTCGTTTT     -180
CGGTCCAATCGCTGTTCCAACTTTACTTACACAAGTCGTACAGCGTCTCTCTCTCTCTCTCTCACTC    -110
ACTTCCTCTTATAAAGACTCTGATCAAACGTATAATCGGAAAACTCCATTCTTTGATACCATCGATAA    -40
                                  +1→
TACTAAGAGAGGTGATTGATTCTTTAATCACTGTTGATATCCCTTAACTTTGATCCATTACTCTGTTCA    31
ATCATTTTTGTAGAG
```

FIG. 3

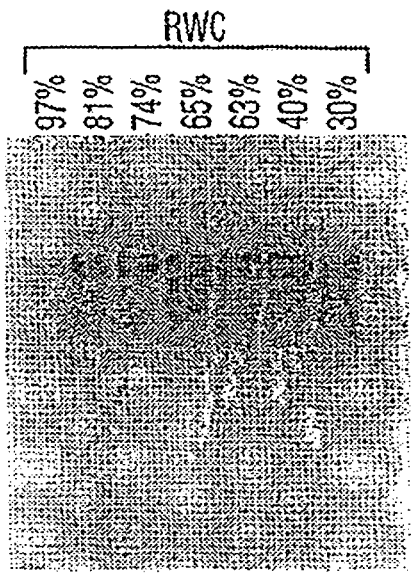
FIG. 4A
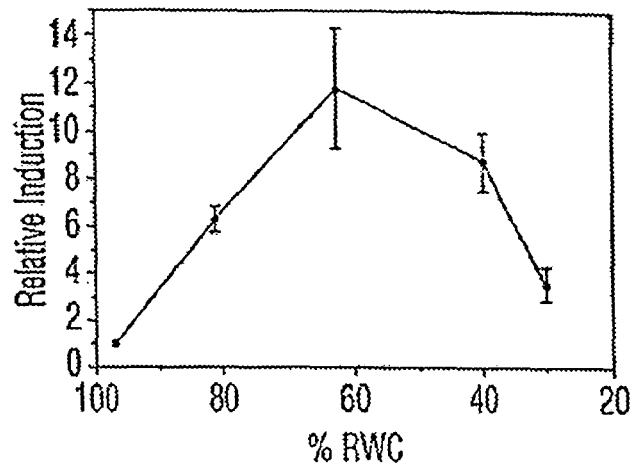
FIG. 4B
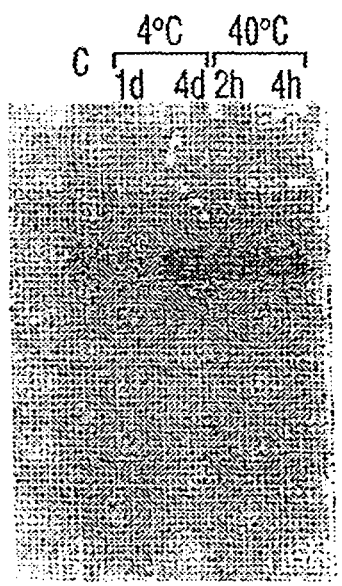
FIG. 4C
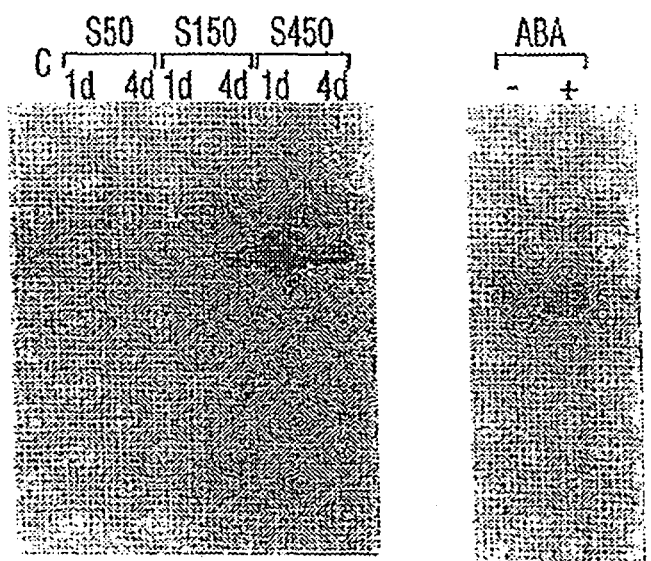
FIG. 4D
FIG. 4E

```
GGCCACAAAACCGGCGAAGAGATACGCGACAGCTAGAGGCGTCGAGGCCCCTTGTCTCTTAGTTGATCTCGCC                                    94

ATGGCTGCCACCGTCGCCGTGGACAATCTGAACCCCAAGGTTTAAAATGTGAGTATGCTGTGGTGGAGAGATTGTCATCCATGCTCAGCGCTTG            190
 M  A  A  T  V  A  V  D  N  L  N  P  K  V  K  C  E  Y  A  V  V  R  G  E  I  V  I  H  A  Q  R  L            32

CAGGAACAGCTAAAGACTCAACCAGGGTCTCTACCTTTTGATGAGATCCTCTATGTAACATTGGAACCCAATCTCTTGGTCAGCAACCAGTT             286
 Q  E  Q  L  K  T  Q  P  G  S  L  P  F  D  E  I  L  Y  C  N  I  G  N  P  Q  S  L  G  Q  Q  P  V            64

ACATTCTCAGGGAGGTTCTTGCCATGATACCTGGAAGAGCAACAGGAGCATACAGCCATGGTATTAAAGGACTTCGTGATGCAATTGCTTCGA           382
 T  F  F  R  E  V  L  A  L  C  D  H  P  D  L  L  Q  R  E  E  I  K  T  L  F  S  A  D  S  I  S  R            96

GCAAAGCAGATTCTTGCCATGATACCTGGAAGAGCAACAGGAGCATACAGCCATGGTATTAAAGGACTTCGTGATGCAATTGCTTCTGGG             478
 A  K  Q  I  L  A  M  I  P  G  R  A  T  G  A  Y  S  H  S  Q  G  I  K  G  L  R  D  A  I  A  S  G            128

ATCGCTTCACGAGATGGATTCCCTGCTAATGCTGATGACATTTTCTCACAGATGCTGACTTGGGACTGCAAGTCCTGAGCCCCAGGGTGTCACTGATTACTGATA 574
 I  A  S  R  D  G  F  P  A  N  A  D  D  I  F  L  T  D  G  A  S  P  G  V  H  L  M  M  Q  L  L  I           160

AGGAATGAGAAAGATGGCATTCTGGTTCCGCCGATTCCTCAGTACCCCGTTGTCCGAGCTCCTATAGCTCTTGTCCATACTAT                    670
 R  N  E  K  D  G  I  L  V  P  P  I  P  Q  Y  P  P  L  Y  S  A  S  I  A  L  H  G  G  A  L  V  P  Y  Y      192

CTCAATGAATGAGAGCACGGGCTGGGGTTTGGAAACCTCTGATGTTAAGAAGCAACTTGAAGATGCTCGGTTCAAGAGGCATCAACGTTAGGCTTGGTG       766
 L  N  E  S  T  G  W  G  L  E  T  S  D  V  K  K  Q  L  E  D  A  R  S  R  G  I  N  V  R  A  L  V            224

GTTATCAATCCAGGAAATCCAACTGGACAGGTACTTGCTGAAGAAAACCAATATGACATTGTGAAGTTCTGCAAAAATGAGGGTCTTGTTCTTA           862
 V  I  N  P  G  N  P  T  G  Q  V  L  A  E  E  N  Q  Y  D  I  V  K  F  C  K  N  E  G  L  V  L  L            256

GCTGATGAGGTATACCAAGAGAACATCTATGTTGACAACAAGAAGAAATTCCACTCTTTCAAGAAGATAGTGAGATCCTTGGGATACGGCGAGGAGGAT      958
 A  D  E  V  Y  Q  E  N  I  Y  V  D  N  K  K  K  F  H  S  F  K  K  I  V  R  S  L  G  Y  G  E  E  D        288
```

FIG. 5

```
CTCCCTCAGTATCATATCAATCTGTTCTAAGGATATTATGTGAGTGTGGTAAAAGAGGTGGTTACTTTGAGATTACTGGCTTCAGTGCTTCCA    1054
 L  P  L  V  S  Y  Q  S  V  S  K  G  Y  Y  G  E  C  G  K  R  G  G  Y  F  E  I  T  G  F  S  A  P    320

GTAAGAGAGCAGATCTACAAATAGCAGTCAGTGAACCTATGCTCCAATATCACTGGCCAGATCCTTGTCTAGTCTTGTCATGAACCACCAAAGGCT   1150
 V  R  E  Q  I  Y  K  I  A  S  V  N  L  C  S  N  I  T  G  Q  I  L  A  S  L  V  M  N  P  P  K  A    352

AGTGATGAATCATACGCTTCATACAGGCAGAAAAAGATGGAATCCTCGCATCTTTAGCTCGTGCGAAGGCATTGGAGCATGCATTCAATAAA    1246
 S  D  E  S  Y  A  S  Y  K  A  E  K  D  G  I  L  A  S  L  A  R  R  A  K  A  L  E  H  A  F  N  K    384

CTTGAGGGAATTACTTGCAACGAGGCTGAAGGAGCAATGTACGTGTTCCCTCAAATCTGTCTGCCACAGAAGGCAATTGAGGCTGTAAAGCTGCT    1342
 L  E  G  I  T  C  N  E  A  E  G  A  M  Y  V  F  P  Q  I  C  L  P  Q  K  A  I  E  A  A  A  K  A    416

AACAAGGCACCTGATGCATTCTATGCTCTTCGTCTCCTGAGTGGAATGCGTGTTGTCCCCAGGTTCCTGGCACA    1438
 N  K  A  P  D  A  F  Y  A  L  R  L  L  E  S  T  G  I  V  V  V  P  G  S  G  F  G  Q  V  P  G  T    448

TGGCACTTCAGGTGCGACGATCCTTCCGCAGGAGATAAGATCCCGGCAGTGTTCATGAGGCGTTCATGTCAGAGTAT    1534
 W  H  F  R  C  T  I  L  P  Q  E  D  K  I  P  A  V  I  S  R  F  T  V  F  H  E  A  F  M  S  E  Y    480

CGTGACTAAACTGGTGCAACATGTGGGATTACATACAACCCTCATGGGGTTTCGTAGGCGTTCTTGGTTTGCCCCCCCCTTCTCTCTCTC    1630
 R  D                                                                                              482

TCTCTCTCCTGACAGCATCCCTCCTCTAGATGAGACAAAATAAAGCAAAGCCATGTCATCCTTAAAAAAAAAA    1701
```

FIG. 5 Cont'd

Root/shoot ratios:

btg26/GUS, line 4  -  19.5
btg26/GUS, line 8  -  1.9
btg26/GUS, line 13 -  6.5
btg26/GUS, line 17 -  15.7
btg26/GUS, line 18 -  13.2

```
                            SEQUENCE LISTING

<160> NUMBER OF SEQ ID NOS: 2

<210> SEQ ID NO 1
<211> LENGTH: 365
<212> TYPE: DNA
<213> ORGANISM: Brassica napus

<400> SEQUENCE: 1
gtcgacctgc aggtcaacgg atcctaatcg gggtatatcc cgacccggaa aaagaaacgt      60
aggacacgtg acaaaacttc atatgatccg agtgaatcaa gccaaaaggg ggattgacac     120
aacagctcag ctttcgtttt cggtccaatc gctgttccaa ctttacttac aagtcgtaca     180
cgtctctctc tctctctctc tctctcactc acttcctctt ataaagactc tctgatcaaa     240
cgtataatcg gaaaactcca ttctttgata ccatcgataa tactaagaga ggtgattgat     300
tctttaatca ctgtttgata tccttaactt tgatccattt actctgttca atcatttttg     360
tagag                                                                365

<210> SEQ ID NO 2
<211> LENGTH: 1701
<212> TYPE: DNA
<213> ORGANISM: Brassica napus

<400> SEQUENCE: 2
ggccacaaaa ccgcggaaag agatagacgg acagctagag gcgtcggaag atactcgctg      60
ctctgccgcc cccttcgtct tagttgatct cgccatggct gccaccgtcg ccgtggacaa     120
cctgaacccc aaggttttaa aatgtgagta tgctgtgcgt ggagagattg tcatccatgc     180
tcagcgcttg caggaacagc taaagactca accagggtct ctaccttttg atgagatcct     240
ctattgtaac attgggaacc cacaatctct tggtcagcaa ccagttacat tcttcaggga     300
ggttcttgcc ctttgtgatc atccagacct gttgcaaaga gaggaaatca aacattgtt     360 cagtgctgat tctatttctc gagcaaagca gattcttgcc atgatacctg gaagagcaac     420
aggagcatac agccatagcc agggtattaa aggacttcgt gatgcaattg cttctgggat     480
cgcttcacga gatggattcc ctgctaatgc tgatgacatt tttctcacag atggagcaag     540
tcctggggtg cacctgatga tgcaattact gataaggaat gagaaagatg gcattcttgt     600
cccgattcct cagtacccct tgtactcggc ttccatagct cttcatggcg gagctcttgt     660
```

-continued

```
cccatactat ctcaatgaat cgacgggctg gggtttggaa acctctgatg ttaagaagca      720
acttgaagat gctcggtcaa gaggcatcaa cgttagggct ttggtggtta tcaatccagg      780
aaatccaact ggacaggtac ttgctgaaga aaaccaatat gacatagtga agttctgcaa      840
aaatgagggt cttgttcttc tagctgatga ggtataccaa gagaacatct atgttgacaa      900
caagaaattc cactctttca agaagatagt gagatccttg ggatacggcg aggaggatct      960
ccctctagta tcatatcaat ctgtttctaa gggatattat ggtgagtgtg gtaaaagagg     1020
tggttacttt gagattactg gcttcagtgc tccagtaaga gagcagatct acaaaatagc     1080
atcagtgaac ctatgctcca atatcactgg ccagatcctt gctagtcttg tcatgaaccc     1140
accaaaggct agtgatgaat catacgcttc atacaaggca gaaaagatg gaatcctcgc      1200
atctttagct cgtcgtgcga aggcattgga gcatgcattc aataaacttg agggaattac     1260
ttgcaacgag gctgaaggag caatgtacgt gttccctcaa atctgtctgc cacagaaggc     1320
aattgaggct gctaaagctg ctaacaaagc acctgatgca ttctatgctc ttcgtctcct     1380
cgagtcgact ggaatcgtcg ttgtccctgg atcaggattt ggccaggttc ctggcacatg     1440
gcacttcagg tgcacgatcc ttccgcagga ggataagatc ccggcagtca tctcccgctt     1500
cacggtgttc catgaggcgt tcatgtcaga gtatcgtgac taaactggtg caacatgtgg     1560
gattacatac aaccctcatg gggttttcgt aggcgttctt ggttttgccc cccccccct     1620
tctctctctc tctctctctg acagcatcct cctctagatg agacaaaata aagcaaagcc     1680
atgtcatcct taaaaaaaaa a                                               1701
```

PLANTS WITH ENHANCED LEVELS OF NITROGEN UTILIZATION PROTEINS IN THEIR ROOT EPIDERMIS AND USES THEREOF

RELATED APPLICATIONS

This application is a continuation-in-part application of U.S. application Ser. No. 10/321,718 filed Dec. 17, 2002, now abandoned, which is a continuation of U.S. application Ser. No. 09/568,221, filed May 9, 2000, now abandoned, which is a continuation of U.S. application Ser. No. 08/599,968, filed Feb. 14, 1996, now U.S. Pat. No. 6,084,153, which are all incorporated by reference herein in their entirety. This application is also a continuation-in-part application of U.S. application Ser. No. 09/493,803, filed Jan. 1, 2000, which is incorporated by reference herein in its entirety.

FIELD OF THE INVENTION

The present invention relates to non-naturally occurring plants that display enhanced agronomic characteristics due to elevated levels of nitrogen utilization proteins in the root of the plants. The present invention also relates to an inducible promoter and, in particular, a promoter element which exhibits stress inducible expression in a root specific manner.

BACKGROUND OF THE INVENTION

In the last 50 years, the "green revolution" has contributed to higher yields, greater stability of harvests and, as a result, higher farm income. This "green revolution" (Borlaug, 2000) resulted in part from conventional plant breeding yielding superior plant varieties, but also from (1) expansion of land mass for cultivation; (2) improved agricultural practices through fertilizer application and crop rotation and (3) pesticide and herbicide use which decrease the loss in productivity arising from plant pathogens and insect pests. However, the limits of these strategies are currently being realized. One approach, which will aid in addressing these limitations, is the development of crop species that have increased nitrogen use efficiency, thus increasing productivity on land of both marginal and good quality.

Nitrogen is an essential, limiting nutrient required for plant growth (Vance, 1997). To increase plant productivity, high levels of N-fertilizer are normally applied to crops. Global usage of fertilizer has increased from 32 to 87 million MT (1970 to 2000) and is projected to increase to 240 million MT by 2050 (Tilman, 1999). In Canada and the US alone 25 million tons of N, P, and K fertilizer are applied annually at a cost of $10 B (US) (Tisdale et al., 1985). To sustain high crop yields, up to 200 kg per hectare of fertilizer is often applied to many agricultural species. For example canola shows a positive correlation for seed yield, with fertilizer applications of up to 135 kg per hectare, after which there is a slight decrease in yield (Porter 1993). In addition to the economic costs of fertilizer application, there are environmental effects including the deterioration of soil quality, pollution and health hazards. The extensive use of $NH_4^+$, urea or nitrate as fertilizers all have negative impact on the environment. Heavy use of urea and ammonium based fertilizers causes acidification of soils, which results in decreases in both yield and the quality of crops (Goulding et al., 1998). Nitrate based fertilizers are problematic in that they do not remain in the soil, with up to 50% being lost through leaching (Carpenter et al., 1995). The release of gaseous nitrogen compounds from fertilizers also exacerbates acid rain (Matson et al., 1998) and the greenhouse effect (Tilman, 1999). Thus there is a need for plants that are capable of utilizing nitrogen more efficiently so that less nitrogen is required for the same yield or higher yields may be obtained with current levels of nitrogen use.

SUMMARY OF THE INVENTION

The present invention addresses the need for plants with enhanced nitrogen utilization by providing non-naturally occurring plants with elevated levels of nitrogen utilization proteins where the plant needs such enzymes—in the root, preferably the root epidermis. The non-naturally occurring or transgenic plants of the present invention have elevated levels of nitrogen utilization proteins in their roots, preferably localized to the root epidermis and therefore show enhanced growth when compared to the same variety of naturally occurring plant on limiting levels of nitrogen. In some embodiments, the elevated levels localized to the specific tissue are at least 50% greater, at least $100$% greater, at least 150% greater, at least 200% greater, at least 250% greater, at least 300% greater, at least 500% greater, at least 750% greater, at least 1000% greater, at least 2000% greater, at least 3000% greater, at least 4000% greater, or at least 5000% greater than the average levels in the remaining plant tissues. In another aspect, the non-naturally occurring or transgenic plants of the present invention may be stimulated to further increase the levels of such nitrogen utilization protein by exposure to stress or drought.

In certain embodiments of the present invention, the nitrogen utilization protein is chosen from fungal nitrate reductases, mutant nitrate reductases lacking post-translational regulation, glutamate synthetase-1, glutamate dehydrogenase, aminotransferases, nitrate transporters (high affinity and low affinities), ammonia transporters and amino acid transporters. The nitrogen utilization proteins may be isolated from plants, fungi, yeast or microbes. In yet other embodiments, the non-naturally occurring plant comprises a gene encoding a nitrogen utilization protein operably linked to a promoter which directs root specific expression and is inducible by drought and/or stress. In a preferred embodiment, the promoter directs root epidermis specific expression. In still another embodiment, the promoter directs root epidermis specific expression and is inducible by drought and/or stress. In certain other embodiments, the promoter is chosen from the LeAMT1 promoter, the LeNRT1 promoter, the GmNRT2 promoter, the KDC1 promoter, the PHT1 promoter, the GOGAT promoter, the OsRAB5 promoter, and the ALF5 promoter. In various embodiments, the plant is chosen from corn, wheat, rice, barley, canola, soybean, cotton, alfalfa, safflower, tomato and potato.

The present invention also includes the preferred method of making the non-naturally occurring plants of the present invention. The preferred method involves a gene which includes a nitrogen utilization protein such as a nitrogen assimilation/metabolic pathway enzyme coding sequence operably associated with a promoter that directs expression of the protein in a root specific manner. In certain preferred embodiments, the nitrogen utilization protein will be ectopically expressed. In one embodiment, the promoter is root specific and drought and/or stress inducible. In another embodiment, the promoter is root epidermis specific. In still another embodiment, the promoter is root epidermis specific and drought and/or stress inducible. Such a genetic construct acts to confer to a plant or plant cell, into which it is introduced, enhanced nitrogen uptake/assimilation/metabolic properties by virtue of expressing a nitrogen utilization protein when and where the plant can most efficiently utilize such a protein.

Such genetic constructs can be inserted into plant transformation vectors and/or introduced to plant cells. Transformed plants can be produced which contain the genetic construct of the present invention.

In accordance with a broad aspect of the present invention, there is provided a plant gene adapted for transcription and translation in a plant system comprising a nitrogen utilization protein such as a nitrogen uptake/assimilation/metabolism enzyme coding sequence operably associated with a promoter further inducible under conditions where it is desirable that plants have enhanced ability to assimilate or metabolize nitrogen.

In accordance with another broad aspect of the present invention, there is provided a method for producing a plant having inducible nitrogen uptake, assimilation and/or metabolic capabilities comprising: transforming a plant cell by introducing a genetic construct having a nitrogen utilization protein coding sequence operably associated with a promoter further inducible under conditions where it is desirable that plants have enhanced ability to assimilate or metabolize nitrogen.

The promoter is selected to be further inducible under any condition where it would be desirable to cause the plant to have enhanced nitrogen uptake, assimilation or use capabilities. For example, suitable promoters may include, but are not limited to, those which are induced by application of sources of nitrogen, wound inducible or induced by application of certain chemicals. Transgenic plants containing the genetic construct of the present invention exhibit enhanced agronomic characteristics such as ability to grow on lower amounts of nitrogen or grow better on the same amounts of nitrogen when compared to control plants or plants having constitutively over-expressed nitrogen utilization protein encoding genes. The particular agronomic characteristic which is enhanced usually depends on the nature of the promoter, the growth conditions selected for the plant, and can include enhanced stress tolerance and/or more efficient nitrogen uptake, storage or metabolism, allowing the plants of the present invention to be cultivated with lower nitrogen fertilizer input and in nitrogen starved conditions or allowing faster growth, greater vegetative and/or reproductive yield under normal growing conditions.

In addition to the above described plants, the present invention includes plant parts of the above described plants and seeds from the above described plants.

BRIEF DESCRIPTION OF THE DRAWINGS

FIG. 3: DNA sequence of the *Brassica napus* btg-26 promoter (SEQ ID NO:1).

FIG. 4A: Northern blot analysis of btg-26 expression during drought. Total RNA (10 mg) from leaf tissue taken from control plants having 97% relative water content (97% RWC) and plants dehydrated to the % RWC's as, indicated, was fractionated on a 1.2% agarose formaldehyde gel and probed with btg-26 genomic DNA.

FIG. 4B: Quantitative analysis of btg-26 induction. Each time point represents the mean induction determined from three independent slot blots and two Northern blots. All blots were reprobed with a cyclophilin cDNA control to correct for loading error. Induction is determined relative to the level of expression in fully hydrated plants (97%).

FIG. 4C: Northern blot analysis of btg-26 expression during cold acclimation and heat shock. Total RNA (10 mg) from leaf tissue taken from control plants (C) or plants exposed to 4° C. for one or four days or exposed to 40° C. for two or four hours. The RNA was fractionated on a 1.2% agarose formaldehyde gel and probed with btg-26 genomic DNA.

FIG. 4D: Northern blot analysis of btg-26 expression during salinity stress. Total RNA (10 mg) from leaf tissue taken from control plants (C) or plants exposed to salinity stress by watering with 50 mM NaCl (S50), 150 mM NaCl (S150) or 450 mM NaCl (S450) for one or four days. The RNA was fractionated on a 1.2% agarose formaldehyde gel and probed with btg-26 genomic DNA.

FIG. 4E: Northern blot analysis of btg-26 expression during exposure to abscisic acid (ABA). Total RNA (10 mg) from leaf tissue taken from plants soaked for one day in a solution containing either 0 μM (−) or 100 μM ABA (+). The RNA was fractionated on a 1.2% agarose formaldehyde gel and probed with btg-26 genomic DNA.

FIG. 5: Nucleotide (SEQ ID NO: 2) and deduced amino acid sequence (SEQ ID NO:3) of the AlaAT cDNA from barley.

DETAILED DESCRIPTION OF THE INVENTION

The present invention provides a non-naturally occurring plant that is characterized by elevated levels of one or more nitrogen utilization proteins in the root, preferably the root epidermis, as compared to the naturally occurring variety of the plant. A preferred method of making such non-naturally occurring plant is to ectopically express a nucleic acid molecule encoding a nitrogen utilization protein operably linked to a root or root epidermal specific promoter. In some embodiments, the promoter is also stress or drought inducible. The nitrogen utilization protein may be selected, for example, from the following list of proteins: fungal nitrate reductases, mutant nitrate reductases lacking post-translational regulation, glutamate synthetase-1, glutamate dehydrogenase, aminotransferases, nitrate transporters (high affinity and low affinities), ammonia transporters, amino acid transporters, and other proteins involved in nitrogen metabolism. The proteins and nucleic acids encoding such can be isolated from plants, yeast, fungi, bacteria or other organisms.

One preferred method of making the non-naturally occurring plants of the present invention involves the expression of nitrogen utilization proteins such as alanine amino transferase (AlaAT) and Aspartate amino transferase (AspAT) under control of a root-specific promoter such as btg-26 in plants results in a plant with enhanced growth. As set forth in the Examples, root specific expression of AlaAT and AspAT lead to enhanced growth of the non-naturally occurring plants when compared to the naturally occurring plants. In view of the Examples set forth, the skilled artisan will recognize that root-specific expression of nitrogen utilization proteins results in plants with enhanced agronomic properties. Thus, the invention provides a non-naturally occurring plants with improved agronomic properties.

Definitions

The term "plant" is art-recognized, and includes any monocotyledonous or dicotyledonous plant. Preferred plants for use in the invention include canola, safflower, barley, corn, rice, tobacco, soybean, cotton, alfalfa, tomato, wheat, potato, and certain tree genera, including conifers, deciduous and *Populus species*.

Figure 24:
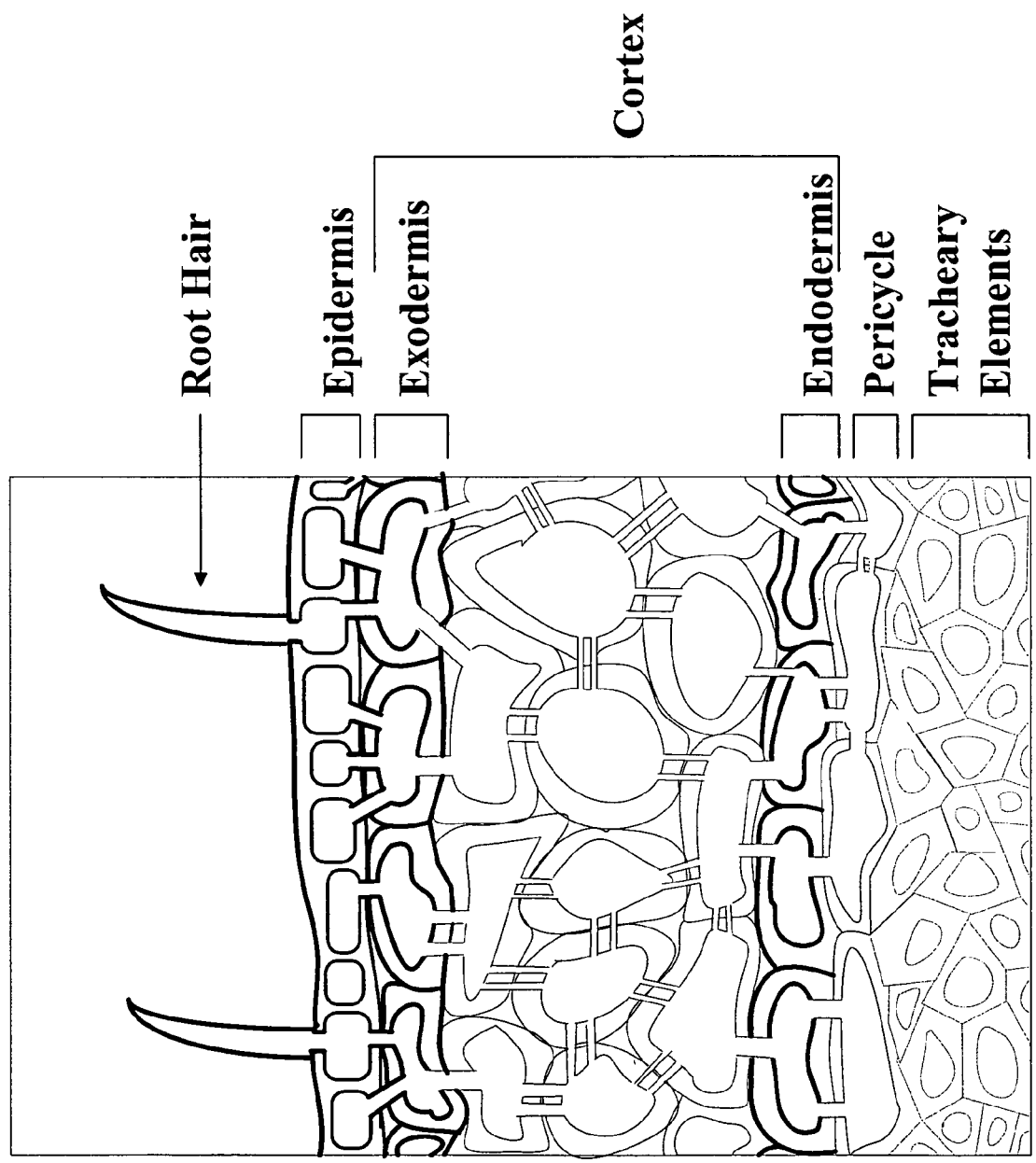
FIG. 24: Representative cross-section of a plant root.

The term "plant part" is art recognized, and includes all parts derived from a plant including, without limitation, stems, shoots, roots, leaves, flowers, fruits, fruiting bodies, and seeds. Plant parts also include discrete tissues, where on of skill in the art would recognize a tissue by the common definition as a group of cells similar to each other, along with their associated intercellular substances, which perform the same function within a plant. Examples of major tissue types include epidermal, and vascular tissues. The root and the parts of the root are all defined by terms commonly used in the art. As root tissues differentiate behind the growing root tip, they form a pattern of layers (tubes) within layers (See FIG. 24). Each layer is composed of tissue that has a specific role to play for the plant. The outermost layer is the epidermis, which is generally only one cell in thickness. This encloses and protects the underlying tissues. Some epidermis cells differentiate into root hair cells and therefore the root hair cells may be included in the epidermis for the purposes of the present invention. These cells extend out into surrounding soil spaces and absorb water, selected mineral ions, and certain organic materials. Under the epidermis is the cortex. The cortex is composed of up to three layers. The outermost layer, which is found in some roots, is the exodermis. The exodermis is a type of hypodermis that may be suberized or lignified. In addition, the exodermis may also have Casparian strips. The midlayer is composed of Parenchymal cells. Parenchymal cells store excess nutrients; for example, sugars are stored as starch. These cells are loosely packed so that the spaces between them can direct water and mineral ions absorbed by root hairs into the central vascular core. The inner layer of cells in the cortex consists of endodermal cells, which surround the vascular cylinder. Endodermal cells are joined by Casparian strips. Casparian strips are a waterproof thickening in the radial and end walls of endodermal and, in some circumstances, exodermal cells of plants. Beneath the endodermis is the pericycle. Pericycle cells can function like meristem and mitotically produce secondary or branch roots. The pericycle also constitutes the outer boundary of the vascular core, a structure that contains the internal, liquid transport highways of the plant in the form of highly specialized tube like or conducting tissues. The vascular core is comprised of tissues that transport nutrients. Water and mineral ions taken in by root hairs and concentrated into the core by the endodermis are transported up into the plant shoot by xylem tubes.

As used herein, the term "non-naturally occurring," when used in reference to a plant, means a plant that has been genetically modified by human intervention. A transgenic plant of the invention, for example, is a non-naturally occurring plant that contains an exogenous nucleic acid molecule, such as a nucleic acid molecule encoding a nitrogen utilization protein and, therefore, has been genetically modified by human intervention. In addition, a plant that contains, for example, a mutation in an endogenous nitrogen utilization regulatory element or coding sequence as a result of calculated exposure to a mutagenic agent, such as a chemical mutagen, or an "insertional mutagen," such as a transposon, also is considered a non-naturally occurring plant, since it has been genetically modified by human intervention. Furthermore, a plant generated by cross breeding with different strains and varieties or selecting a plant that has been genetically modified by human intervention are also considered a "non-naturally occurring plant," because the selection and breeding is performed by human intervention such that the selected plants have the human generated genetic modification. In contrast, a plant containing only spontaneous or naturally occurring mutations is not a "non-naturally occurring plant" as defined herein and, therefore, is not encompassed within the invention.

Based upon the above definitions, it will be clear that a "non-naturally occurring plant comprising elevated levels of one or more nitrogen utilization proteins specifically localized to the root epidermis" is a plant variety that has been genetically modified by human intervention and has at least two fold higher levels of one or more nitrogen utilization proteins in the root epidermis when compared to the same naturally occurring plant and substantially the same levels of the one or more nitrogen utilization proteins in other tissues.

The term "ectopically," as used herein in reference to expression of a nucleic acid molecule, refers to an expression pattern in a non-naturally occurring plant that is distinct from the expression pattern in a comparable naturally occurring plant. Thus, one skilled in the art understands that ectopic expression of a nucleic acid molecule encoding a nitrogen utilization protein can refer to expression in a cell type other than a cell type in which the nucleic acid molecule normally is expressed, or at a time other than a time at which the nucleic acid molecule normally is expressed, or at a level other than the level at which the nucleic acid molecule normally is expressed. For example, under control of the btg-26 promoter, AlaAT is expressed in the roots at elevated levels, and thus, is ectopically expressed.

As used herein, the term "transgenic" refers to a plant that contains an exogenous nucleic acid molecule, which can be derived from the same plant species, from a heterologous plant species, or from a non-plant species.

The term "exogenous," as used herein in reference to a nucleic acid molecule and a transgenic plant, means a nucleic acid molecule originating from outside the plant. An exogenous nucleic acid molecule can have a naturally occurring or non-naturally occurring nucleotide sequence. One skilled in the art understands that an exogenous nucleic acid molecule can be a heterologous nucleic acid molecule derived from the same plant species or a different plant species than the plant into which the nucleic acid molecule is introduced or can be a nucleic acid molecule derived from the a non-plant species such as fungi, yeast, bacteria or other non-plant organisms.

The term "operatively linked," as used in reference to a regulatory element and a nucleic acid molecule, such as a nucleic acid molecule encoding a nitrogen utilization protein, means that the regulatory element confers regulated expression upon the operatively linked nucleic acid molecule. Thus, the term "operatively linked," as used in reference to an exogenous regulatory element such as a root-specific regulatory element and a nucleic acid molecule encoding a nitrogen utilization protein, means that the root-specific regulatory element is linked to the nucleic acid molecule encoding an nitrogen utilization protein such that the expression pattern of the root-specific regulatory element is conferred upon the nucleic acid molecule encoding the nitrogen utilization protein. It is recognized that a regulatory element and a nucleic acid molecule that are operatively linked have, at a minimum, all elements essential for transcription, including, for example, a TATA box.

The term "elevated levels" of a protein of interest, as used herein in reference to protein levels in a non-naturally occurring plant of the invention, means higher levels of protein as compared to the protein levels of a corresponding plant variety lacking the genetic modification introduced by human intervention such as an ectopically expressed nucleic acid molecule encoding a nitrogen utilization protein.

It is recognized that there can be natural variation in the protein levels in a particular plant species or variety. However, the protein levels in a plant of the present invention can be identified by sampling a population of such plants and determining that the normal distribution of the protein in such plants in a given tissue of interest is greater, on average, than the normal distribution of the protein in the corresponding plant variety or species lacking a genetic modification introduced by human intervention such as an ectopically expressed nucleic acid molecule encoding a nitrogen utilization protein. Thus, production of non-naturally occurring plants of the invention provides a means to skew the normal distribution of the protein in a plant, such that the protein levels are, on average, at least about 50% greater, 100% greater, 150% greater, 200% greater, 250% greater, 300% greater, 500% greater, 750% greater, 1000% greater, 2000% greater, 3000% greater, 4000% greater or 5000% greater than in the corresponding plant species that does not contain a genetic modification introduced by human intervention such as an ectopically expressed nucleic acid molecule encoding a nitrogen utilization protein.

When such "elevated levels" are further limited to being localized to a specific tissue, the levels of the protein are higher in the specified tissue than in the other tissues of the plant. In certain embodiments, the protein may be found in all tissues, but the average levels of the protein in the specified tissue are higher than the average levels of the protein in the rest of the plants tissues. Thus, the protein may be found at higher levels in a few other tissues, for example the stomata, but still be considered elevated levels of the protein localized to the specified tissue. The non-naturally occurring plants of the invention will have average levels of the protein of interest in the specified tissue which are at least 50% greater, 100% greater, 150% greater, 200% greater, 250% greater, 300% greater, 500% greater, 750% greater, 1000% greater, 2000% greater, 3000% greater, 4000% greater or 5000% greater than in the average levels of the protein in the rest of the tissues of the plant.

Tissue-specific and Inducible Expression

The term "tissue-specific expression of a protein" is known in the art and includes the expression of a protein in only selected tissues; although the protein may be present in multiple tissues, it is expressed in only a subset of those tissues. In addition, in some cases, the expression may occur throughout the plant but at elevated levels in specific tissues, e.g., a promoter that directs expression in all plant tissues but at elevated levels such as a three fold higher level in root epidermal tissue would be a root epidermal specific promoter. Such selective expression may be due to the influence of one or more regulatory genetic elements, e.g., promoter, repressor, or enhancer elements. One of skill in the art may create artificial promoters by combining such regulatory elements to generate the desired tissue and/or inducible promoter.

It is recognized that there can be natural variation in the tissue-specific protein expression in different tissues in a particular plant species or variety. However, the protein expression levels in a plant of the present invention can be identified by sampling a population of such plants' tissues and determining that the normal distribution of protein expression in such plants in a given tissue of interest is greater, on average, than the normal distribution of aggregate protein expression in the other tissues of such plants. Thus, tissue specific expression provides a means to skew the normal distribution of protein expression in a plant, such that the protein expression levels in the specific tissue are, on average, at least about 50% greater, 100% greater, 150% greater, 200% greater, 250% greater, 300% greater, 500% greater, 750% greater, 1000% greater, 2000% greater, 3000% greater, 4000% greater or 5000% greater than in the other tissues of such plant, recognizing that certain other tissues may also have elevated levels of expression.

As used herein, the term "root-specific promoter" means a promoter that confers a level of expression upon an operatively linked nucleic molecule that is relatively expressed in the root more highly than in other tissues. A root-specific promoter that is expressed in a plant may also lead to relatively higher expression in certain other tissues such as stomatal cells for example and still constitute a root-specific promoter.

As used herein, the term "root-epidermis-specific promoter" means a promoter that confers a level of expression upon an operatively linked nucleic molecule that is relatively expressed in the root epidermis more highly than in other tissues. A root-epidermis-specific promoter that is expressed in a plant may also lead to relatively higher expression in certain other tissues such as stomatal cells for example and still constitute a root-epidermis specific promoter.

As used herein, the term "stress inducible promoter" means a promoter that confers a level of expression upon an operatively linked nucleic molecule that is induced in response to stress. Such stresses may include heat stress, drought, salt or osmotic stress, cold or frost, oxidative stress and chemical stress such as heavy metal exposure.

It is recognized that there can be natural variation in the stress-induced protein expression in a particular plant species or variety. However, the protein expression levels in a plant of the present invention can be identified by sampling a population of such plants under the particular and determining that the normal distribution of protein expression in such plants is greater, on average, than the normal distribution of aggregate protein expression such plants under no stress. Thus, stress-induced expression provides a means to skew the normal distribution of protein expression in a plant, such that the protein expression levels in the specific tissue are, on average, at least about 50% greater, 100% greater, 150% greater, 200% greater, 250% greater, 300% greater, 500% greater, 750% greater, 1000% greater, 2000% greater, 3000% greater, 4000% greater or 5000% greater when such plant is exposed to the particular stress.

In making a plant of the present invention, one of skill in the art may select an existing promoter with the desired tissue specific and/or inducible expression or may construct a promoter by combining regulatory elements with the desired specificity or inducible expression to generate an artificial promoter. A variety of root-specific, root-epidermis-specific and stress inducible regulatory elements useful for ectopic expression in a transgenic plant of the invention are well known in the art. The following list is illustrative of the broad scope of available promoters with associated regulatory elements. The following promoters as well as any other promoter with the desired characteristics may be useful without modification, or may provide regulatory elements for constructing artificial promoters.

The BTG-26 gene is from *Brassica napus*. The promoter directs high levels of protein expression in the root epidermis as described herein.

LeAMT1 encodes an ammonium transporter protein in tomato. The promoter directs preferential expression in root hairs with little to no expression in stems or leaves. Lauter et al. (1996, PNAS 3:8139)

The LeNRT1-1 gene is a nitrate transporter found in the tomato plant. The promoter directs preferential expression in root tissues with little to no expression in stem or leaves. Furthermore, the transcripts accumulate preferentially in root hairs when tomato plants are exposed to nitrate. Lauter et al. (1996, PNAS 3:8139). However, without exposure to nitrate, the promoter may direct higher expression in non-root hair cells of the roots than in root hairs in the absence of nitrate GmNRT2 is a putative high-affinity nitrate transporter in soybean. The promoter is induced by both nitrogen starvation and the addition of external nitrate. However, the presence of ammonium prevents the strong induction seen under N-starvation and nitrate addition. No studies have been performed on the tissue specificity of expression, so this gene is not necessarily root-specific. Also, this gene is from a dicot. Amarasinghe et al. (1998, Planta 206:44).

KDC1 encodes a K+ channel in carrot. This gene has a homolog in at least *Arabidopsis* that has a similar expression pattern. Downey et al. (2000, J. Biol. Chem. 275:39420) The promoter directs expression in roots, but not in leaves, stem, or tubers. The expression is localized to root epidermal cells, and particularly to root hair cells. The promoter of a KDC1 homolog is strongly up-regulated by nitrate at 1 h of exposure to nitrate, and remained so until 24 h after exposure. Wang et al. (2001, Plant Physiol. 127:345)

In *Arabidopsis*, the PHT1;1 gene encodes a phosphate transporter molecule. The promoter directs expression in roots. This expression was strongest in the epidermis, and in the trichoblast cells. Mudge et al. (2002, Plant J. 31:341). However, the promoter also directs expression in hydathodes of cotyledons and leaves, axillary buds, and in the peripheral endosperm of germinating seeds. In older, flowering plants, expression was found only in young lateral roots. Low Pi soil increases expression in the root hair zone and induces expression in the columella and lateral root cap.

In *Arabidopsis*, the PHT1;2 gene encodes a phosphate transporter. The promoter directs expression only in roots. Strong expression occurs in epidermal cells and root hairs in low Pi soil. There is much stronger expression in trichoblasts than in atrichoblasts. (Mudge et al. 2002, The Plant J. 31:341). However, the promoter directs weaker expression than that of PHT1;1 in high Pi soil. Thus, the strong expression in low Pi soil is not found in soils with higher levels of Pi. Also, no expression is seen in root tips. In older regions of primary roots (near the hypocotyl junction) the highest expression is in cortical cells, and not the epidermis. Older plants only expressed PHT1;2 in young lateral roots.

In *Arabidopsis*, the PHT1;3 gene encodes a phosphate transporter molecule. The promoter directs expression mainly in root tissues. Also, both in lateral roots and near the tip of the primary root, it expresses most strongly in trichoblasts and much lower in the stele than in the primary root proper. Mudge et al. (2002, Plant J. 31:341). However, in the primary root, this promoter directs expression predominately in the stele. Furthermore, it expresses only in the pericycle layer in primary roots and in lateral roots near the junction with the primary root. Also, some plants weakly expressed the gene in vascular tissue of young leaves and in hydathodes. Besides this, the gene also proved to be induced by low Pi levels, which would not be good for plants grown in soils with higher levels of Pi.

In *Arabidopsis*, the PHT1;4 gene encodes a phosphate transporter. The promoter directs expression in the roots. Specifically, expression in the epidermis and root tips. (Mudge et al. 2002, Plant J. 31:341) However, there is some expression in hydathodes, axillary buds, and, at lower levels, throughout the cotyledons. Additionally, the promoter is induced in low Pi soil, which makes its usefulness questionable for soils with more regular levels of Pi.

The NADH GOGAT gene is for a glutamine:oxoglutarate aminotransferase enzyme found in barley and rice. The promoter directs expression in the root of nitrogen depleted plants in response to addition of 1 mM ammonium. Yamaya et al. (1995, Plant Cell Physiol. 36:1197). The promoter directs expression to the epidermis and exodermis. Tobin and Yamaya (2001, J. Exp. Bot. 52:591) Conversely, in N-depleted plants, the promoter directs expression in the central cylinder, apical meristem, and in secondary root primordia, with only weak expression in the epidermis. However, the promoter directs some expression in rice leaves, with the highest level of expression in the youngest, non-green, unexpanded leaves; these levels both decreased with increasing age and with expansion of these leaves (Yamaya et al. 1992, Plant Physiol. 100:1427).

The OsRAB5a gene encodes a small GTP-binding protein in rice. The promoter directs higher expression in root, weaker expression in shoot, flower and immature grain, and little to no expression in leaves or stem. It showed similarity to *Arabidopsis* gene RHAL. OsRAB5a promoter is upregulated by nitrate, and by nitrogen and phosphorus starvation. (Wang et al. 2002, Plant Sci. 163:273).

The ALF5 gene is from the multidrug and toxic compound extrusion (MATE) family in *Arabidopsis*. The promoter directs high levels of protein expression in the root epidermis and cortex, especially in the elongation zone of young roots. In older roots, the staining spreads into the meristematic region. The promoter directs no expression in the stem. Diener et al. (2001, Plant Cell 13:1625).

The following promoters are examples of promoters that one of skill in the art could take regulatory elements from in constructing promoters with the desired characteristics.

The TUA2 gene encodes an alpha-tubulin subunit in many plants. In maize, this promoter directs expression only in the epidermis, or rarely in discrete meristematic cells as demonstrated by in situ hybridization (Uribe et al. 1998, Plant Mol. Biol. 37:1069). However, the promoter yields relatively lower expression and is more specific to the root meristems and immature root cap. The epidermal expression seems to be in apical undifferentiated cells (Uribe et al. 1998, Plant Mol. Biol. 37:1069). Also, Villemur et al. (1994, Plant Mol. Biol. 24:295) found TUA2 transcripts in pollen and shoot of seedlings.

GOS9 is a gene found in rice. The promoter directs expression that is concentrated much more densely in roots than in leaves (Rey et al. 1993, Plant Mol. Biol. 23:889). The highest levels are in the epidermis, but it also expresses strongly in the exodermis. In the indica variety, cultivar IR36 showed high transcript levels in roots in both young seedlings and mature plants, while very low levels were found in the leaves of young seedlings, and no mRNA was found in green tissues of mature plants. Also, expression in roots of mature plants is higher in IR36 than in T309.

However, GOS9 in other varieties is expressed in leaves, and in the roots is expressed strongly in the endodermis, and in cortical cells near the endodermis. In addition, seedlings of the variety japonica T309 contained similar mRNA levels in leaves and roots at both the 2 and 3 week stage. Thus, the GOS9 promoter preferably should be from one of the varieties that has low expression in the leaves.

IRE is a putative protein kinase is encoded by this gene in *Arabidopsis*. The promoter directs expression in the specialization zone and the proximal part of the elongation zone. In epidermis, there is higher expression in trichoblasts than atrichoblasts. Furthermore, root hair cells show higher levels of expression than the surrounding cells. Cis-elements in 5' upstream region appear to be responsible for directing this expression. The promoter directs very high expression in the roots. Oyama et al. (2002, Plant J. 30:289). However, the promoter still directs low-level expression in all tissues, with higher expression in floral organs.

The KOJAK/AtCSLD3 gene encodes a putative cellulose synthase in *Arabidopsis*. The promoter directs preferential expression in growing root hair cells. Favery et al. (2001, Genes & Dev. 15:79). However, the levels are quite low. Also, mRNA from the gene was found throughout the plant using RT-PCR. Also the promoter may not direct expression in mature root hairs.

The LeRSE-1 gene is a putative mannitol dehydrogenase found in tomato. Expression of this gene is induced by exposure of the shoot to light. The promoter directs expression in roots and root hairs of tomato plants without detectable expression in hypocotyls, cotyledons, leaves, sink leaves, flowers, or green fruit. (Lauter 1996, Mol. Gen. Genet. 252: 751)

The LeNRT1-2 gene is a nitrate transporter found in the tomato plant. The promoter directs preferential expression in root hairs may be induced by nitrate. In addition, there was no detectable expression in the stem or leaves. (Lauter et al. 1996, PNAS 3:8139). However, the promoter is not induced by ammonium. Moreover, after 18 hours of exposure to nitrate, the expression levels from this promoter become undetectable.

The NRT2;1Np gene encodes a putative nitrate transporter in *Nicotiana* plumbaginifolia. The promoter direct strong expression in roots, and only in low amounts in other tissues. The promoter is also moderately induced by nitrate. Quesada et al. (1997, Plant Mol. Biol. 34:265) a dicotyledonous plant.

AS encodes the enzyme asparagine synthetase in rice. The promoter directs expression that is markedly increased in roots but not leaves upon addition of 1 mM $NH_4^+$. Glutamine also produced induction of the promoter. Kawachi et al. (2002, Physiol. Plant. 114:41).

ZMRPRN1 is a putative ferredoxin-NADP+ oxidoreductase (FNR) in maize (Ritchie et al. 1994, Plant Mol. Biol. 26:679). The promoter directs only 5% of the expression level in leaf tissue as in root tissue. The promoter is rapidly and transiently induced by nitrate, even at low levels (10 mM). Furthermore, potassium and ammonium do not induce the promoter. However, the tissue specific expression within the root is as yet unknown.

FNR encodes a ferredoxin-NADP+ oxidoreductase. The promoter is induced rapidly by nitrate. Aoki and Ida (1994, Biochim. Biophys. Acta 1183:553). However, the nitrate induction is transient, as induction drops off rapidly after 2 hours from the addition of nitrate. The promoter is not induced by ammonium. The tissue-specific expression within the root is unknown.

The FD gene encodes a ferredoxin in rice. (Doyama et al. 1998, Plant Sci. 137:53). The promoter is induced in the roots by potassium nitrate, and also by ammonium chloride. The induction is rapid, within 1 hour of addition of nutrient. The promoter is not known to be root specific, since tests for tissue-specific expression have not been reported.

The FD IV gene codes for a ferredoxin in maize. The promoter is nitrate inducible, showing high induction within 2 hours of addition of 16 mM calcium nitrate. Matsumura et al. (1997, Plant Physiol. 114:653) The promoter is not known to be root specific, since tests for tissue-specific expression have not been reported.

The LRX1 gene encodes a chimeric leucine-rich repeat/ extensin protein in *Arabidopsis* (Baumberger et al. 2001, Genes & Dev. 15:1128). The promoter directs expression exclusively in the root, specifically in developing root hair cells. However, there is little to no expression in the mature zone of the root.

The RCG2 gene is found in rice. The promoter directs expression in the root cap and elongation zone, and in cortical tissues. Xu et al. (1995, Plant Mol. Biol. 27:237). However, expression is also seen in the vascular tissues, but little in the epidermis of roots. The promoter also directs strong expression in the vascular tissues of leaves. In fact, about equal expression is observed in root and leaf tissue.

Chimeric regulatory elements, which combine elements from different genes such as those listed above, also can be useful for ectopically expressing a nucleic acid molecule encoding a nitrogen utilization protein in the root epidermis (Comai et al., Plant Mol. Biol. 15:373 (1990)). One skilled in the art understands that a particular tissue-specific or stress inducible regulatory element is chosen based, in part, on the plant species in which a nucleic acid molecule encoding a nitrogen utilization protein is to be ectopically expressed and on the desired level of expression and specificity of localization.

An exogenous root specific regulatory element useful in a transgenic plant of the invention also can be an inducible regulatory element, which is a regulatory element that confers conditional expression upon an operatively linked nucleic acid molecule, where expression of the operatively linked nucleic acid molecule is increased in the presence of a particular inducing agent or stimulus as compared to expression of the nucleic acid molecule in the absence of the inducing agent or stimulus. Such inducible regulatory elements include copper-inducible regulatory elements (Mett et al., Proc. Natl. Acad. Sci. USA 90:4567-4571 (1993); Furst et al., Cell 55:705-717 (1988)); tetracycline and chlor-tetracycline-inducible regulatory elements (Gatz et al., Plant J. 2:397-404 (1992); Roder et al., Mol. Gen. Genet. 243:32-38 (1994); Gatz, Meth. Cell Biol. 50:411-424 (1995)); ecdysone inducible regulatory elements (Christopherson et al., Proc. Natl. Acad. Sci. USA 89:6314-6318 (1992); Kreutzweiser et al., Ecotoxicol. Environ. Safety 28:14-24 (1994)); heat shock inducible regulatory elements (Takahashi et al., Plant Physiol. 99:383-390 (1992); Yabe et al., Plant Cell Physiol. 35:1207-1219 (1994); Ueda et al., Mol. Gen. Genet. 250:533-539 (1996)); and lac operon elements, which are used in combination with a constitutively expressed lac repressor to confer, for example, IPTG-inducible expression (Wilde et al., EMBO J. 11:1251-1259 (1992)).

An inducible regulatory element useful in the transgenic plants of the invention also can be, for example, a nitrate-inducible promoter derived from the spinach nitrite reductase gene (Back et al., Plant Mol. Biol. 17:9 (1991)). Additional inducible regulatory elements include salicylic acid inducible regulatory elements (Uknes et al., Plant Cell 5:159-169 (1993); Bi et al., Plant J. 8:235-245 (1995)); plant hormone-inducible regulatory elements (Yamaguchi-Shinozaki et al., Plant Mol. Biol. 15:905 (1990); Kares et al., Plant Mol. Biol. 15:225 (1990)); and human hormone-inducible regulatory elements such as the human glucocorticoid response element (Schena et al., Proc. Natl. Acad. Sci. USA 88:10421 (1991)).

It should be recognized that a non-naturally occurring plant of the invention, which contains an ectopically expressed nucleic acid molecule encoding a nitrogen utilization protein, also can contain one or more additional modifications, including naturally and non-naturally occurring mutations that can, for example, increase activity of the nitrogen utilization protein.

Nitrogen Utilization Proteins

As used herein, the term "nitrogen utilization protein" means a protein that when expressed appropriately enhances the ability of a plant to utilize nitrogen. This enhanced ability may be detected in a number of different methods. The simplest way is by comparing the growth of a non-naturally occurring plant expressing such protein with the growth of a naturally occurring plant of the same variety under limiting nitrogen condition. The non-naturally occurring plant grows better than the naturally occurring plant under the same condition if the protein is a nitrogen utilization protein.

In addition to testing plants through direct comparison, the enhanced ability to utilize nitrogen may be determined by measuring the nitrogen use efficiency as defined by Moll, et al. (1982). Moll et al. defined the nitrogen use efficiency as grain production per unit of N available:

$$NUE = Gw/Ns$$

where Gw=grain weight and Ns=Nitrogen available.

In this case, Ns equals the amount of available nitrogen in the soil, plus the amount of applied nitrogen. A second related way to define NUE is by looking at applied nitrogen. With this method, the calculation is as follows:

$$NUE_{app} = Gw/Napp$$

where Gw=grain weight and Napp=Nitrogen applied.

Both of these calculations are widely used methods of describing nitrogen utilization efficiency. In Alberta Canada, a commonly used reference is that 3.0 bushels of canola can be expected for each pound of nitrogen applied, with some varieties being more efficient than others. In Brawley, Calif., the application of one pound of fertilizer yielded between 15 to 57 pounds of canola seed, depending upon the amount of nitrogen applied. See example 6 below. It is recognized, of course, that nitrogen response is not a straight line, i.e., increasing amounts of nitrogen does not correlate directly with an increase in plant mass. The nitrogen level used therefore must always be stated when this type of analysis is employed. Expressing nitrogen use efficiency in this manner is invaluable for making cropping and fertilizer decisions. It is less valuable in describing the underling physiological principles. In certain embodiments of the present invention, the non-naturally occurring plant will have a nitrogen use efficiency rating that is at least 10% higher, at least 20% higher, at least 30% higher, at least 40% higher, at least 50% higher, at least 75% higher, at least 100% higher, at least 150% higher, at least 200% higher, or at least 250% higher than the naturally occurring plant of the same variety at limiting nitrogen levels.

Given the above definition and the current understanding of nitrogen metabolism in the art, one of ordinary skill will have no difficulty in determining what proteins constitute nitrogen utilization proteins of the present invention. Once one of skill in the art has identified a likely nitrogen utilization protein, the protein can be expressed in plants in order to verify that it enhances nitrogen utilization. The examples provide demonstration of testing proteins likely to be nitrogen utilization proteins and unlikely to be nitrogen utilization proteins.

The following discussion illustrates how one of skill in the art may identify likely nitrogen utilization proteins. The following discussion is intended to describe one general method that one of skill in the art may use without limiting the scope of what constitutes a nitrogen utilization protein to one selected by the following methods. Utilization of nitrogen by plants involves three steps: uptake, assimilation, and translocation. A nitrogen utilization protein may enhance utilization of nitrogen by directly or indirectly affecting any one or more of these three steps. Soil nitrogen is in the form of $NO_3^-$, $NO_2^-$, $NH_4^+$ and urea. The main forms of nitrogen available in the soil are $NH_4^+$ and $NO_3^-$. The uptake of $NH_4^+$ and $NO_3^-$ into the plant from the soil solution is mediated by at least two transport systems for each ion. These systems are called high-affinity and low-affinity transport systems (HATS and LATS) respectively (Crawford and Glass 1998). Plant genes encoding high-affinity and low-affinity transporters have been identified for both nitrate and ammonium in *A. thaliana* (Ninnenman et al., 1994; Zhuo et al., 1999; Tsay et al., 1993; Sohlenkamp et al., 2000; Howitt et al., 2000). Fraisier et al., (2000) increased NRT2 protein levels by transforming *N. plumbiginafolia* with NpNrt2.1 under the control of the rolD or CaMV35S promoters. Transcript abundance increased dramatically, but resulted in no increase in nitrate transport. It has also been demonstrated that when tissue nitrate levels were elevated due to environmental and genetic manipulations (eg. tungstate addition, an inhibitor of nitrate reductase (Deng et al., 1989; Vidmar et al., 2000b) and a NR double mutant (Lejay et. al. 1999)) it resulted in an increase in Nrt2.1 transcript, but a decrease in nitrate transport capacity. This decrease in transport capacity is hypothesized to be post-translational mediated (Lejay et al., 1999; Vidmar et al., 2000b). Currently the mode of this post-translational regulation is unknown, but is hypothesized to be regulated by the phosphorylation-dephosphorylation events at conserved serine sites within the NRT2 proteins (Amarashinghe et al., 1998; Forde, 2000; Vidmar et al., 2000a). Thus one of skill in the art would take care in selecting nitrogen utilization proteins that enhance uptake directly. Nitrogen utilization proteins that are nitrogen transporters may be used; however, they either must not be post translationally regulated or the expression must include other proteins responsible for such post translational regulation. Another set of nitrogen utilization proteins that may be used in the present invention are proteins that up regulate the endogenous nitrogen transport proteins post translationally.

Nitrogen utilization proteins may also include enzymes involved in nitrogen assimilation. Once nitrate has entered the cell it is reduced by nitrate reductase to nitrite. Nitrate reductase (EC 1.6.6.1 and EC1.6.6.2) is substrate and light inducible, has a high turnover rate, is present in the cytoplasm and in the plasma membrane, and is regulated post-translationally (Oaks et al., 1979; Huber et al., 1996; Moorhead et al., 1996, 1999; Campbell, 1999). There are two different isoforms, the NADH-dependent NR, which uses NADH as a source of electrons, and the bispecific NAD(P)H-dependent NR that can use either NADH or NADPH as sources of reducing power. Both have been shown to be functional in the root and shoot, dependent on the age and growth conditions of the plant (Guerrero et al., 1981). The NR enzyme in higher plants has been shown to be a homodimer of 105-kDa to 120-kDa subunits. The subunit consists of three prosthetic groups, namely flavin, heme and a molybdenum-pterin cofactor (Campbell and Smarelli, 1986). The NR expression is controlled by many different factors, both internal and external, including nitrate, amino acids, $CO_2$, light, cytokinin, and circadian rhythms (reviewed by Caboche and Rouze, 1990). At present, two different cDNAs have been cloned in *Arabidopsis*, nia1 and nia2, which encode two nitrate reductase enzymes (Cheng et al., 1988; Crawford et al., 1988). Both proteins encode NADH-specific NR. The *Arabidopsis thaliana* genome does not contain a gene encoding NAD(P)H-bispecific NR. In *Brassica napus*, two cDNAs have been isolated encoding NR, again, both are NADH-specific and are developmentally regulated (Fukuoka et al., 1993).

Molecular analysis of nitrate reductase has demonstrated that regulation of NR occurs at multiple levels. 1) Transcriptional regulation of genes encoding NR has been demonstrated (Cheng et al., 1988; Deng et al., 1989) with an increase in NR transcript after treatment of plants with nitrate (Cheng et al., 1991; Vincentz et al., 1993) and a decrease in transcript abundance with amino acids (especially glutamine) (Deng et al., 1991). 2) NR activity is regulated post-translationally through phosphorylation-dephosphorylation events. The phosphorylation of NR on serine 543 (spinach) or the equivalent serine in *Arabidopsis* (serine 534) creates a high affinity binding site for 14-3-3 proteins. The binding of 14-3-3 inhibits the activity of NR and this is the signal that initiates proteolysis of the enzyme (Moorhead et al., 1996; Weiner and Kaiser, 1999; Cotelle et al., 2000). The fungal NR does not have a corresponding phosphorylation site or 14-3-3 binding motif. This indicates that the endogenous plant regulatory system may be bypassed by over-expressing the fungal NR. In addition, mutated plant NR which can not be phosphorylated and therefore inhibited may also be expressed as nitrogen utilization proteins. For example, mutation of serine 534 to an aspartate in the *Arabidopsis* NR resulted in a protein that was no longer inhibited by 14-3-3 and would therefore be a good candidate for a nitrogen utilization protein (Su et al., 1996).

Nitrogen utilization proteins may also be obtained from nitrogen translocation and assimilation enzymes. Once nitrite is produced, it is transported into the chloroplast where is it reduced to ammonium by nitrite reductase. Nitrite reductase is a monomer of 60 to 70 kDa. NiR is thought to be transcriptionally regulated in the same manner as NR. The $NH_4^+$ generated is then incorporated into glutamate to form glutamine (Oaks, 1994; Lam et al., 1996) by glutamine synthetase. Radiotracer, kinetic and inhibitor studies have shown that glutamate dehydrogenase (GDH) plays principally a catabolic role in plant cells and may only play a part in primary assimilation when ammonium levels are very high (Coruzzi and Last, 2000). Glutamine synthetase plays a central role in nitrogen metabolism since it catalyzes the transfer of inorganic nitrogen into an organic form. Plant glutamine synthetase (GS) has a molecular weight of 320-380 kDa. GS is made up of eight subunits in the form of two tetramers. GS isoforms can be divided into two types: GS1 present in the cytosol and GS2 present in the plastid. The chloroplast GS2 enzyme is predominant in leaves, where it is thought to function in primary assimilation and the reassimilation of photorespiratory ammonium. GS1 is present in low levels in photosynthetic tissue, but is at high concentrations in roots and is believed to have a role in primary ammonium assimilation there.

It has been established for several plant species that GS is encoded by a multi-gene family and the heterogeneity of isoforms has a genetic origin. Plants generally contain only one gene per haploid genome coding for the plastidial GS and several genes coding for the cytosolic GS. The genes that encode for the cytosolic form account for at least three loci in *Arabidopsis thaliana* (Peterman and Goodman, 1991), and pea (Tingey et al., 1988; Tingey et al., 1987). Transcription of plastidal GS is primarily regulated by light and nitrogen (Lightfoot et al., 1988; Edwards and Corruzi, 1989), whereas cytoplasmic GS is regulated by external N-supply (Finnemann and Schjoerring, 1999) and non-external factors such as senescence (Downs et al., 1994). Early studies investigating the role of GS attempted to alter N-metabolism by over-expression of either GS1 or GS2 under the control of CaMV35S promoter, however no effect was observed (Hirel et al., 1992; Eckes et al., 1997). Vincent et al. (1997), found that over-expression of soybean GS1 in Lotus (controlled by CaMV35s promoter) had no effect on growth rate except under high $NH_4^+$ treatment (12 mM), in which plants developed at an increased rate. Also, Migge et al. (2000) over-expressed GS2 under the control of a shoot specific promoter (soybean ribulose-1,5-biphossphate carboxylase/oxygenase small subunit gene promoter) resulting in a 15-fold increase in foliar GS2 transcript compared to wild type. However, GS2 activity was only 2-fold higher reflecting post-translational control and this resulted in only a marginal increase in biomass (20%).

From the GS-GOGAT cycle, glutamate is used to continue nitrogen flow in the plant through a number of different reactions (Oaks, 1994; Lam et al., 1996). This flow is mediated predominantly by trans-amination events in which an amino group of glutamate is shuffled to a new carbon skeleton. This trans-amination reaction completes the process of bringing nitrogen into the plant and converting it to a readily usable resource.

In addition to the proteins directly involved in uptake and assimilation and the regulatory proteins of those proteins, nitrogen utilization proteins can also include downstream enzymes that affect the nitrogen balance. It is believed that when downstream enzymes transfer amino-groups from compounds that are involved in nitrogen storage to other compounds this disturbs the nitrogen balance by depleting pools of nitrogen, the plants will react to the lowered levels but increasing its uptake and assimilation to restore the balance. An example of such enzymes are amino transferases. As demonstrated in the Examples, both AlaAT and AspAT function as nitrogen utilization proteins. While not limiting the invention to a particular mechanism, it is believed that such enzymes function by depleting the available pools of nitrogen storing amino acids which in turn leads to upregulation of the uptake and assimilation pathways in the plant. Each of AlaAT and AspAT transfer an amino-group from glutamate to another amino acid, thus depleting the pools of glutamate, a nitrogen storage compound. Examples of aminotransferases include, without limitation, alanine aminotransferase, aspartate aminotransferase, cysteine aminotransferase, glycine aminotransferase, tyrosine aminotransferase, leucine aminotransferase, kynurenine—oxoglutarate aminotransferase, 2,5-diaminovalerate aminotransferase, histidinol-phosphate aminotransferase, acetylornithine aminotransferase, succinyldiaminopimelate aminotransferase, 4-aminobutyrate aminotransferase, D-alanine aminotransferase, (S)-3-amino-2-methylpropionate aminotransferase, 4-hydroxyglutamate aminotransferase, tryptophan aminotransferase, diamine aminotransferase, dTDP-4-amino-4,6-dideoxy-D-glucose aminotransferase, UDP-4-amino-2-acetamido-2,4,6-trideoxyglucose aminotransferase, L-lysine aminotransferase, histidine aminotransferase, 2-aminoadipate aminotransferase, branched-chain amino acid aminotransferase, 5-aminovalerate aminotransferase, dihydroxyphenylalanine aminotransferase, phosphoserine aminotransferase, pyridoxamine-phosphate aminotransferase, taurine aminotransferase, 1D-1-guanidino-3-amino-1,3-dideoxy-scyllo-inositol aminotransferase, aromatic amino acid transferase, dTDP-4-amino-4,6-dideoxygalactose aminotransferase, N(6)-acetyl-beta-lysine aminotransferase, 2-aminohexanoate aminotransferase, ornithine(lysine) aminotransferase. N(2)-acetylornithine 5-aminotransferase, D-4-hydroxyphenylglycine aminotransferase, cysteine-conjugate transaminase, and diaminobutyrate-2-oxoglutarate transaminase. One of skill in the art could select from the available aminotransferases based upon the availability of the target substrates in the plant of interest.

Preferably, a nitrogen utilization protein is orthologous to the plant species in which it is ectopically expressed to produce a non-naturally occurring plant. A nucleic acid molecule encoding tomato AlaAT, for example, can be ectopically expressed in a tomato plant to produce a non-naturally occurring tomato variety characterized by elevated levels of a nitrogen utilization protein. Similarly, a nucleic acid molecule encoding canola AlaAT, for example, can be ectopically expressed in canola to produce a non-naturally occurring canola plant characterized by elevated levels of a nitrogen utilization protein.

A nucleic acid molecule encoding a nitrogen utilization protein also can be ectopically expressed in a heterologous plant to produce a non-naturally occurring plant characterized by elevated levels of a nitrogen utilization protein. Nitrogen utilization proteins have been cloned from a number of species (including *Arabidopsis*, tomato, sugar beets, petunia, rice, etc). Thus, ectopic expression of a nucleic acid molecule encoding a nitrogen utilization protein in a heterologous plant can produce a plant with enhanced agronomic properties. Furthermore, a nucleic acid molecule encoding a nitrogen utilization protein, for example, can be ectopically expressed in more distantly related heterologous plants, including dicotyledonous and monocotyledonous angiosperms and gymnosperms, fruit trees, berry plants and vines and, upon appropriate ectopic expression, can enhance the nitrogen utilization efficiency of the plant. Also, the nitrogen utilization protein can be of non-plant origin such as fungi, yeast, bacteria and other organisms and will still function within a plant.

Potential nitrogen utilization proteins can be routinely assayed for the ability to enhance plant growth and nitrogen use efficiency. Numerous examples of screening a variety of constructs are provided below.

The nitrogen utilization protein gene may be a gene naturally expressed in the selected plant, or it may be heterologous to the selected plant. The gene may originate from any source, including viral, bacterial, plant or animal sources. The gene can be modified in any suitable way in order to engineer a gene or plant with desirable properties. In one embodiment, the gene is modified to be transcribable and translatable in a plant system; for example, the gene can be modified such that it contains all of the necessary poly-adenylation sequences, start sites and termination sites which allow the coding sequence to be transcribed to mRNA (messenger ribonucleic acid) and the mRNA to be translated in the selected plant system. Further, the target gene may be modified such that its codon usage is more similar to that of native genes of the selected plant. Such target gene modifications and the methods by which they may be made are well known in the art.

Nitrogen utilization proteins may include full length proteins, protein fragments with nitrogen utilization activity as well as proteins generated by gene shuffling or other methods such as those disclosed in U.S. Pat. Nos. 6,395,547, 6,376, 246, 6,365,408, and 6,358,740, which are herein incorporated by reference.

Plants of the Present Invention

The non-naturally occurring plants of the present invention display an enhanced growth phenotype due to superior nitrogen use efficiency when compared to naturally occurring plants of the same variety. One embodiment of such non-naturally occurring plants includes plants with elevated levels of one or more nitrogen utilization proteins in the root epidermis of the plant. In a preferred embodiment, the levels of the one or more nitrogen utilization protein(s) may be further elevated by exposing the plant to stress. In another embodiment, the non-naturally occurring plant has elevated levels of one or more nitrogen utilization proteins that may be further elevated by exposing the plant to stress.

The non-naturally occurring plants of the invention can be any one of a variety of plant species, including a monocotyledonous or dicotyledonous angiosperm or a gymnosperm.

A preferred method of making such non-naturally occurring plants is by ectopic expression of an exogenous nucleic acid molecule encoding a nitrogen utilization protein operably linked to an appropriate promoter. The appropriate promoter will depend upon the particular embodiment. In one embodiment, the invention provides a transgenic plant having an ectopically expressed nitrogen utilization protein that is operatively linked to a root-epidermis-specific promoter. In another embodiment, the invention provides a transgenic plant having an ectopically expressed nitrogen utilization protein that is operatively linked to a root-epidermis-specific promoter that is also stress inducible. In yet another embodiment, the invention provides a transgenic plant having an ectopically expressed nitrogen utilization protein that is operatively linked to a root-specific promoter that is also stress inducible. Use of the btg-26 promoter is a preferred method of making the plants of the present invention; however, the plants may be constructed using root specific promoters other than the btg-26 promoter (including derivatives of the btg-26 promoter). Furthermore, use of the alanine aminotransferase protein as a nitrogen utilization protein is a preferred method of making the plants of the present invention; however, the plants may be generated with elevated levels of nitrogen utilization proteins other than the alanine aminotransferase protein (including derivatives of the alanine aminotransferase protein).

In still other embodiments, an exogenous regulatory element with the appropriate expression characteristics may be introduced into the plant such that the exogenous regulatory element is operably linked to an endogenous nitrogen utilization gene and alters the expression pattern of the gene in a manner that elevates tissue specific expression. One example of this would be to transfect a plant with the btg-26 promoter such that the promoter integrates in a way that it is operably linked to one of the plant's endogenous nitrogen utilization proteins. Examples of such methods may be found in U.S. Pat. No. 5,641,670, herein incorporated by reference.

In yet another embodiment, an exogenous nitrogen utilization gene may be introduced to the plant such that the exogenous nitrogen utilization gene is operably linked to an endogenous promoter which directs the appropriate expression of the gene in a manner that enhances nitrogen use efficiency.

The methods and genetic constructs disclosed herein may be used to produce a plant of any species capable of utilizing the promoter such that the transgenic plant has tissue-specific expression of one or more nitrogen utilization proteins. Both monocotyledonous and dicotyledonous plants are amenable to such alteration. The invention is intended to be particularly applicable to, for example, crop plants (especially those of the *genus Brassica*), ornamental plants, and trees (particularly conifers and the *genus Populus*). Particularly suitable plants for the practice of the present invention include, but are not limited to, canola, barley, corn, rice, tobacco, soybean, cotton, alfalfa, tomato, wheat, potato, aspen, cottonwood, conifers and poplar.

The transgenic plants and seeds produced according to the present invention may be further useful in breeding programs for the production of plant species having enhanced nitrogen use efficiency (e.g., two transgenic plants of the invention each having expression of a different desired transgene in the same plant tissue may be crossed to result in progeny transgenic plants having tissue-specific expression of both transgenes or a transgenic plant of the present invention may be crossed with a non-transgenic plant to generate a non-naturally occurring plant that has the transgene of the transgenic plant and other desired traits from the non-transgenic plant). In this fashion it is possible to produce non-naturally occurring plants having a combination of desirable traits in selected tissue(s) of the plant.

Furthermore, it will be understood by one skilled in the art that different species of plants may be more or less amenable to genetic manipulation in general, and that, therefore, it may be advantageous to first transform a related species of the desired plant by the methods and with the constructs of the invention and to subsequently introduce the tissue-specific expression of the target gene into the desired plant species by cross-breeding techniques. Such techniques and appropriately related plant species are well known to one skilled in the art.

Plant cells or protoplasts that have been transformed with the gene construct of the present invention can be regenerated into differentiated plants using standard nutrient media supplemented with shoot-inducing or root-inducing hormone, using methods known to those skilled in the art (see, for example, Shahin, E. A. U.S. Pat. No. 4,634,674 and references therein, incorporated herein by reference in their entirety). Seeds may additionally be harvested from such transgenic plants using methods well known in the art and further used to regrow the transgenic plants and hybrids of the invention.

In addition to the above plants, the present invention includes the various parts of such plants, including without limitation, stems, shoots, roots, leaves, flowers, fruits, fruiting bodies, and seeds.

Uses of the Invention

The plants of the present invention may be used in different ways depending upon the conditions. The plants are better able to thrive on nutrient-poor soils. It is well known in the art that certain plant species, particularly crop plants, deplete the soil of nitrogen. In order to replenish the nitrogen, it is necessary either to fertilize the soil (an expensive and environmentally damaging procedure) or to cultivate plants known to fix nitrogen thereby increasing the nitrogen in the soil (e.g., clover or soybean), which may be less economically or nutritively desirable crops. The methods of the invention permit the targeted expression of genes involved in nitrogen uptake (e.g., transport molecules) to those tissues in which the uptake occurs (e.g., the root or root hairs) to thereby improve the ability of the plant to absorb nitrogen from the environment. Thus, the non-naturally occurring plants of the present invention may be grown on nutrient poor soil without supplementation with nitrogen fertilizer.

In addition, the non-naturally occurring plants of the present invention may also be cultivated with lower amounts of nitrogen fertilizer and still produce the same yield as the naturally occurring variety. This may be used in areas that are at particular risk for the negative environmental impact caused by overuse of nitrogen fertilizer.

Also, the non-naturally occurring plants of the present invention may be cultivated with the same levels of nitrogen fertilizer as the naturally occurring variety. The non-naturally occurring plants will produce higher yields which will result in the end in less fertilizer being used because fewer acres will be required to grow the same amount of a given crop.

As another example, where the appropriate promoter is additionally includes a regulatory element induced by the presence of nitrate, such as, for example, elements in the nitrate reductase promoter (Cheng et al., 1988, ibid.; Cheng et al., 1991, Plant Physiol. 96:275-279), the plant will be induced to assimilate and/or use nitrogen upon application of a nitrogenous fertilizer. Alternately, or in addition, the promoter can be inducible, for example, by an exogenously applied chemical such as alcohol or ABA (see, e.g., Marcotte et al., 1989, Plant Cell 1:969-976). This chemical could be included in nitrogenous fertilizer thereby inducing expression of the nitrogen utilization protein. Thus, plants can more efficiently utilize fertilizer input by rapidly taking up the nitrogen in the fertilizer and storing it at the time of application, to thereby reduce the amounts of nitrogenous fertilizer which are lost to leaching, etc. This may permit a further reduction in the amount of nitrogenous fertilizer required to be applied to a crop, to obtain crop yields comparable to those obtained using normal cultivation techniques and plants which have not been modified according to the present invention. Additional agronomic advantages can include faster growth and crop yield, Where nitrogenous fertilizer input is maintained at levels used in common crop cultivation techniques.

Methods of the Invention

The invention further provides a method of producing a non-naturally occurring plant characterized by elevated levels of one or more nitrogen utilization proteins localized to the root epidermis. One method is practiced by ectopically expressing a nucleic acid molecule encoding a nitrogen utilization protein operably linked to a root-epidermis-specific promoter in the plant, whereby nitrogen utilization protein levels in the root epidermis are increased due to ectopic expression of the nucleic acid molecule. In a preferred embodiment, the levels of the nitrogen utilization protein are further elevated when the plant is exposed to stress. Another method is practiced by ectopically expressing a nucleic acid encoding a nitrogen utilization protein operably linked to a root-specific, stress inducible promoter, whereby nitrogen utilization protein levels in the root are increased due to the ectopic expression and may be further increased by exposing the plant to stress.

As discussed above, the term "ectopically" refers to expression of a nucleic acid molecule encoding a nitrogen utilization protein in a cell type other than a cell type in which the nucleic acid molecule is normally expressed, at a time other than a time at which the nucleic acid molecule is normally expressed or at an expression level other than the level at which the nucleic acid molecule normally is expressed.

Actual ectopic expression of a nitrogen utilization protein is dependent on various factors. The ectopic expression is generally limited to root epidermal tissues or root tissues, as appropriate, but can include expression restricted to a small number of other tissues, and can be achieved by a variety of routine techniques. Mutagenesis, including seed or pollen mutagenesis, can be used to generate a non-naturally occurring plant, in which a nucleic acid molecule encoding a nitrogen utilization protein is ectopically expressed. Ethylmethane sulfonate (EMS) mutagenesis, X-Ray mutagenesis, transposon mediated mutagenesis or T-DNA mediated mutagenesis also can be useful in ectopically expressing a nitrogen utilization protein to produce a plant with enhance nitrogen use efficiency (see, generally, Glick and Thompson, supra, 1993). While not wishing to be bound by any particular mechanism, ectopic expression in a mutagenized plant can result from inactivation of one or more negative regulators of an endogenous nitrogen utilization protein, for example.

Ectopic expression of a nitrogen utilization protein also can be achieved by expression of a nucleic acid molecule encoding a nitrogen utilization protein from a heterologous regulatory element or from a modified variant of its own promoter. Heterologous regulatory elements include root-epidermis-specific elements, which result in expression of the nitrogen utilization protein in the root epidermis as well as in limited number of other cell types, and inducible regulatory elements, which produce selective expression of a nitrogen utilization protein in response to a stimulus or chemical agent, including stress or drought.

Ectopic expression of a nucleic acid molecule encoding a nitrogen utilization protein can be achieved using an endogenous or exogenous nucleic acid molecule encoding a nitrogen utilization protein. A recombinant exogenous nucleic acid molecule can contain a heterologous regulatory element that is operatively linked to a nucleic acid sequence encoding a nitrogen utilization protein. Methods for producing the desired recombinant nucleic acid molecule under control of a heterologous regulatory element and for producing a non-naturally occurring plant of the invention are well known in the art (see, generally, Sambrook et al., supra, 1989; Glick and Thompson, supra, 1993).

Transformation

An exogenous nucleic acid molecule can be introduced into a plant for ectopic expression using a variety of transformation methodologies including Agrobacterium-mediated transformation and direct gene transfer methods such as electroporation and microprojectile-mediated transformation (see, generally, Wang et al. (eds), Transformation of Plants and Soil Microorganisms, Cambridge, UK: University Press (1995), which is incorporated herein by reference). Transformation methods based upon the soil bacterium Agrobacterium tumefaciens are particularly useful for introducing an exogenous nucleic acid molecule into a seed plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in which the tumor inducing functions are replaced by the nucleic acid sequence of interest to be introduced into the plant host.

Agrobacterium-mediated transformation generally employs cointegrate vectors or, preferably, binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art (Glick and Thompson, supra, 1993). Wounded cells within the plant tissue that have been infected by *Agrobacterium* can develop organs de novo when cultured under the appropriate conditions; the resulting transgenic shoots eventually give rise to transgenic plants that ectopically express a nucleic acid molecule encoding a nitrogen utilization protein. *Agrobacterium* also can be used for transformation of whole seed plants as described in Bechtold et al., C.R. Acad. Sci. Paris. Life Sci. 316:1194-1199 (1993), (which is incorporated herein by reference). *Agrobacterium*-mediated transformation is useful for producing a variety of transgenic seed plants (Wang et al., supra, 1995) including transgenic plants of the Brassicaceae family, such as rapeseed and flax, and transgenic plants of the Fabaceae family such as soybean, pea, lentil and bean.

Microprojectile-mediated transformation also can be used to produce a transgenic plant that ectopically expresses a nitrogen utilization protein. This method, first described by Klein et al. (Nature 327:70-73 (1987), which is incorporated herein by reference), relies on microprojectiles such as gold or tungsten that are coated with the desired nucleic acid molecule by precipitation with calcium chloride, spermidine or PEG. The microprojectile particles are accelerated at high speed into an angiosperm tissue using a device such as the BIOLISTIC PD-1000 (Biorad; Hercules Calif.).

Microprojectile-mediated delivery or "particle bombardment" is especially useful to transform plants that are difficult to transform or regenerate using other methods. Microprojectile-mediated transformation has been used, for example, to generate a variety of transgenic plant species, including cotton, tobacco, corn, hybrid poplar and papaya (see Glick and Thompson, supra, 1993) as well as cereal crops such as wheat, oat, barley, sorghum and rice (Duan et al., Nature Biotech. 14:494-498 (1996); Shimamoto, Curr. Opin. Biotech. 5:158-162 (1994), each of which is incorporated herein by reference). In view of the above, the skilled artisan will recognize that *Agrobacterium*-mediated or microprojectile-mediated transformation, as disclosed herein, or other methods known in the art can be used to produce a transgenic seed plant of the invention.

Kits

Kits for generating a transgenic plant characterized by elevated levels of nitrogen utilization proteins localized to the root epidermis are provided herein. The kits of the invention include a nucleic acid molecule encoding a nitrogen utilization protein and a root-epidermis-specific regulatory element. In a kit of the invention, the nitrogen utilization protein may be, for example, fungal nitrate reductases, mutant nitrate reductases lacking post-translational regulation, glutamate synthetase-1, glutamate dehydrogenase, aminotransferases, nitrate transporters (high affinity and low affinities), ammonia transporters and amino acid transporters. If desired, a kit for generating a transgenic plant characterized by elevated levels of nitrogen utilization proteins localized to the root epidermis can include a plant expression vector containing a nucleic acid molecule encoding a nitrogen utilization protein operatively linked to a root-epidermis-specific regulatory element and a stress or drought inducible regulatory element, which may be the same element as in the case of btg-26.

Nucleic acid molecules encoding nitrogen utilization proteins, such as fungal nitrate reductases, mutant nitrate reductases lacking post-translational regulation, glutamate synthetase-1, glutamate dehydrogenase, aminotransferases, nitrate transporters (high affinity and low affinities), ammonia transporters and amino acid transporters have been described hereinabove. A kit of the invention can contain one of a variety of nucleic acid molecules encoding a nitrogen utilization protein and any root-epidermis-specific regulatory element, such as an element described hereinabove.

If desired, a kit of the invention also can contain a plant expression vector. As used herein, the term "plant expression vector" means a self-replicating nucleic acid molecule that provides a means to transfer an exogenous nucleic acid molecule into a plant host cell and to express the molecule therein. Plant expression vectors encompass vectors suitable for *Agrobacterium*-mediated transformation, including binary and cointegrating vectors, as well as vectors for physical transformation.

Plant expression vectors can be used for transient expression of the exogenous nucleic acid molecule, or can integrate and stably express the exogenous sequence. One skilled in the art understands that a plant expression vector can contain all the functions needed for transfer and expression of an exogenous nucleic acid molecule; alternatively, one or more functions can be supplied in trans as in a binary vector system for *Agrobacterium*-mediated transformation.

In addition to containing a nucleic acid molecule encoding a nitrogen utilization protein operatively linked to both a root-epidermis-specific regulatory element, a plant expression vector of the invention can contain, if desired, additional elements. A binary vector for *Agrobacterium*-mediated transformation contains one or both T-DNA border repeats and can also contain, for example, one or more of the following: a broad host range replicon, an ori T for efficient transfer from *E. coli* to *Agrobacterium*, a bacterial selectable marker such as ampicillin and a polylinker containing multiple cloning sites.

A plant expression vector for physical transformation can have, if desired, a plant selectable marker and can be based on a vector such as pBR322, pUC, pGEM and M13, which are commercially available, for example, from Pharmacia (Piscataway, N.J.) or Promega (Madison, Wis.). In plant expression vectors for physical transformation of a seed plant, the T-DNA borders or the ori T region can optionally be included but provide no advantage.

The invention also provides a method of generating a non-naturally occurring plant that is characterized by elevated levels of one or more nitrogen utilization proteins localized to the root epidermis. The method includes the step of ectopically expressing a nucleic acid molecule encoding a nitrogen utilization protein in the plant, whereby nitrogen utilization protein levels in the root epidermis are increased due to ectopic expression of the nucleic acid molecule. In one embodiment, the method includes the step of introducing an exogenous nucleic acid molecule encoding an nitrogen utilization protein into the plant.

Examples of a non-naturally occurring plant of the invention characterized by elevated levels of one or more nitrogen utilization proteins localized to the root epidermis include plants such as corn, wheat, rice, barley, canola, soybean, cotton, alfalfa, safflower, tomato and potato.

The following examples further demonstrate several preferred embodiments of this invention. While the examples illustrate the invention, they are not intended to limit the invention.

EXAMPLES

Example 1

Isolation and Characterization of Osmotic Stress-Induced Promoter

A *Brassica napus* (cv. Bridger) genomic DNA library (Clontech, Palo Alto, Calif.) was screened using standard techniques (Ausubel et al., 1989, Current Protocols in Molecular Biology, Wiley, Wiley, N.Y.) with the *Pisum sativum* 26 g cDNA (complementary deoxyribonucleic acid) clone (Guerrero et al., ibid), $^{32}$P-labelled with a Random Primer Kit (Boehringer Mannheim, Laval, Quebec). A 4.4 kb SalI fragment containing the entire btg-26 gene was subcloned into the commercially available pT7T3-19U vector (Pharmacia Canada, Inc., Baie d'Urfe, Quebec, Canada) for further analyses.

Identification of a Osmotic Stress-induced Promoter in *Brassica napus*

Several genes activated during drought stress have been isolated and characterized from different plant species. Most of these represent later-responding, ABA-inducible genes (reviewed by Skiver and Mundy, ibid.). Recently, however, an ABA-independent, cycloheximide-independent transcript, 26 g, was reported in Pisum sativum (Guerrero and Mullet, ibid; Guerrero et al., ibid). Because this gene does not require protein synthesis for activation, it is postulated that it represents an early factor in the drought signal transduction pathway. To isolate an osmotic stress induced promoter from *Brassica napus*, the cDNA clone representing the *P. sativum* 26 g gene (Guerrero et al., ibid) was used. Total RNA was isolated from the third leaf of whole plants that had been either watered continuously or dehydrated for four days. Using low stringency hybridization, RNA blot analysis identified a single 1.75 kb transcript that is greatly induced in droughted plants (data not shown). To determine if this mRNA represents a single copy gene in *B. napus*, genomic DNA was digested with EcoRI, HindIII or BglII and analyzed by DNA blot hybridization using the *P. sativum* 26 g cDNA. A single band was identified in each lane (data not shown). It was concluded that this transcript represents a single copy, drought-induced gene in *B. napus*. This gene is referred to as btg-26 (*Brassica* turgor gene—26).

Structure of btg-26 Gene

To isolate the btg-26 gene, a *B. napus* genomic DNA library in EMBL-3 (Clontech, Palo Alto, Calif.) was screened with the *P. sativum* 26 g cDNA. From 40,000 plaques analyzed, a single positive clone was identified with an insert size of approximately 16 kb. A 4.4 kb SalI fragment containing the entire gene was subcloned. The promoter sequence of the btg-26 gene was determined by identification of the mRNA start site using primer extension (Ausubel, ibid.) and is shown in FIG. 3 and SEQ ID NO:1. In FIG. 3, the transcription start site is bolded, underlined and indicated by +1. The TATA box and CAAT box are in bold and double underlined. Postulated functional regions are underlined. The sequence of the btg-26 promoter, coding region and 3' region has been presented in Stroeher et al, (1995, Plant Mol. Biol. 27:541-551).

Expression Analysis of btg-26

Induction of btg-26 expression during drought was examined by RNA blot analysis. Potted *B. napus* plants were naturally dehydrated by withholding water for various lengths of time. Whole leaves were used either to determine relative water content (RWC) of individual plants or to isolate total RNA. As shown in FIGS. 4A and 4B, btg-26 expression is induced rapidly during water loss, reaching a six-fold increase over expression in fully hydrated plants at 81% RWC, increasing to eleven-fold induction at 63% RWC. Further decreases in RWC were associated with a decrease in total amount of btg-26 transcript. At 30% RWC expression was only 3.5-fold over fully hydrated levels.

Because other physiological stresses alter intracellular water content, btg-26 expression was examined in *B. napus* plants exposed to cold, heat shock and salt stress. RNA blot analysis indicated that there was no change in btg-26 expression when plants were transferred from normal growth conditions to 4° C. for one day. However, plants left at 4° C. for four days showed a five-fold induction in btg-26 mRNA. A similar increase was seen when plants were shifted to 40° C. for two or four hours. These results are shown in FIG. 4C and demonstrate that expression of btg-26 is induced during temperature stress. To examine the effect of salt stress, plants were watered to capacity one day or four days with 50 mM, 150 mM, or 450 mM NaCl. The level of btg-26 expression was not affected by 50 mM NaCl regardless of length of exposure. However, growth in 150 mM NaCl caused a two-fold increase in btg-26 mRNA after four days. Exposure to 450 mM NaCl caused the most notable induction, twelve-fold after one day, dropping to four-fold after four days. Refer to FIG. 4D for Northern blots showing these results.

Finally, many drought-inducible genes are also ABA responsive. To examine the role of ABA in btg-26 expression, total RNA was isolated from individual leaves treated with or without ABA. In these experiments, leaves were cut at the petiole and placed in a solution of 0 µM, 50 µM or 100 µM ABA (mixed isomers, Sigma), 0.02% Tween-20 and pH 5.5 for 24 hours. As shown in FIG. 4E, btg-26 expression is induced 2.5-fold when exposed to 100 µM ABA. However, when leaves were exposed to 50 µM ABA, no induction of expression was observed (data not shown). These results indicate that btg-26 is ABA responsive, but that this responsiveness is concentration dependent.

Example 2

Creation of Drought-Induced Nitrogen Assimilation Constructs

This step involved the production of either constitutive or drought induced AlaAT constructs and the introduction of them into *Brassica napus* using *Agrobacterium* mediated genetic transformation. The approach of introducing specific sense or antisense cDNA constructs into plants to modify specific metabolic pathways has been used in a number of species and to modify a number of different pathways. (See Stitt & Sonnewald 1995 for a review; Ann. Rev. of Plant Physiol. and Plant Mol. Biol. 46:341-368). The AlaAT cDNA was introduced under the control of three different promoters. (1) The CaMV promoter which has been shown to be a strong constitutive promoter in a number of different plant species; (2) the btg-26 promoter described in Example 1 and (3) the trg-3 1 promoter which was isolated from tobacco by Guerrero and Crossland (ibid.). The CaMV promoter should result in the constitutive overexpression of AlaAT whereas btg-26 and trg-31 should induce over expression of AlaAT only under conditions of specific stresses, including drought stress.

Plasmid Constructs

Figure 1:
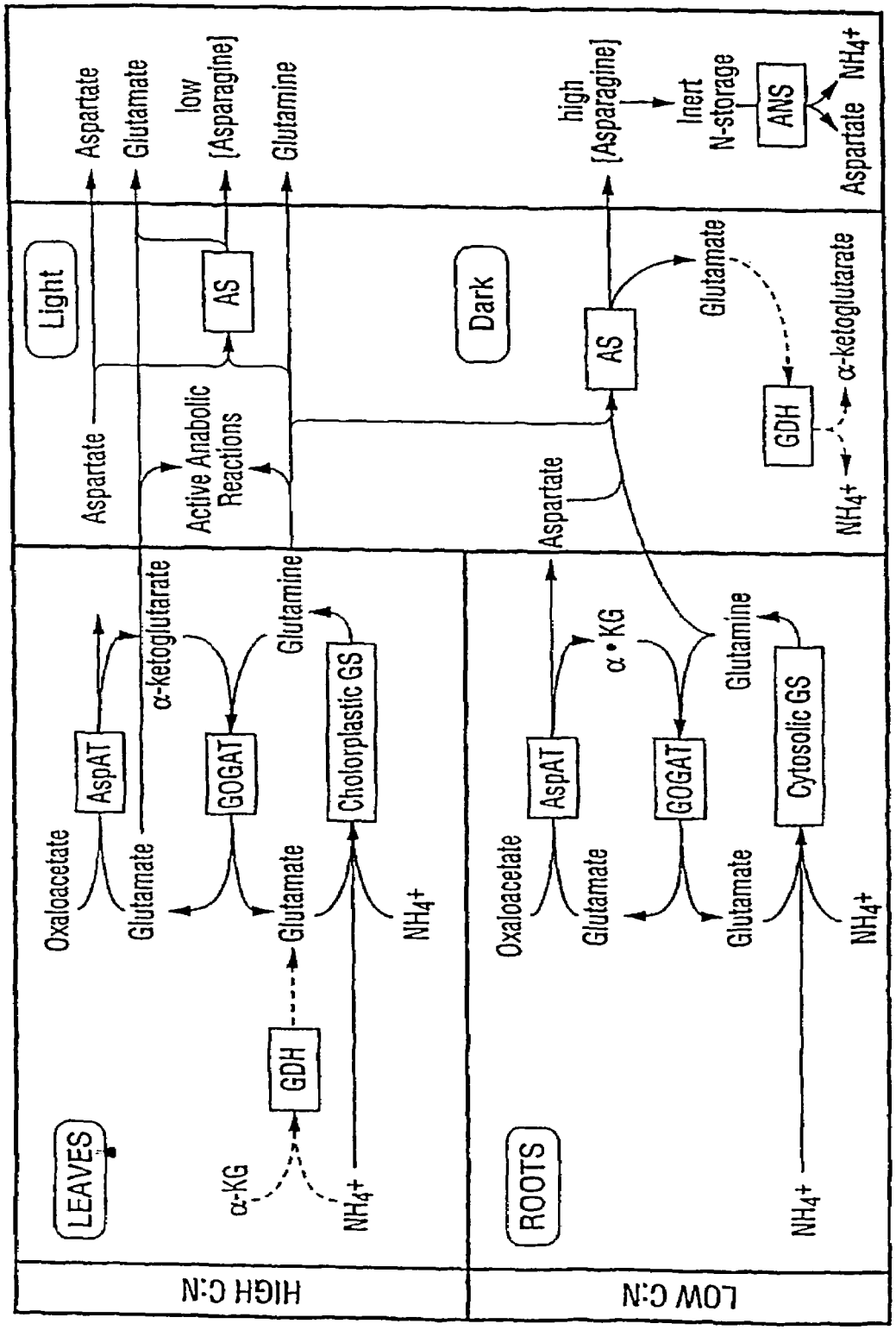
FIG. 1: Major pathways of nitrogen assimilation and metabolism in plants. (Adapted from Lam et al., 1995, Plant Cell 7: 889 where *Arabidopsis* is used as a model system). Some of the enzymes of the nitrogen assimilation and amide amino acid metabolism pathways are shown. Different isoenzymes are known for some of these enzymes which may play different roles under different environmental and tissue conditions. Nitrogen assimilation occurs primarily through the activities of glutamine synthetase (GS) and glutamate synthase (GOGAT). While not indicated as such, aspartate aminotransferase also catalyses the reverse reaction. The roles of glutamate dehydrogenase (GDH) are postulated, as indicated by the dashed lines.
Figure 2:
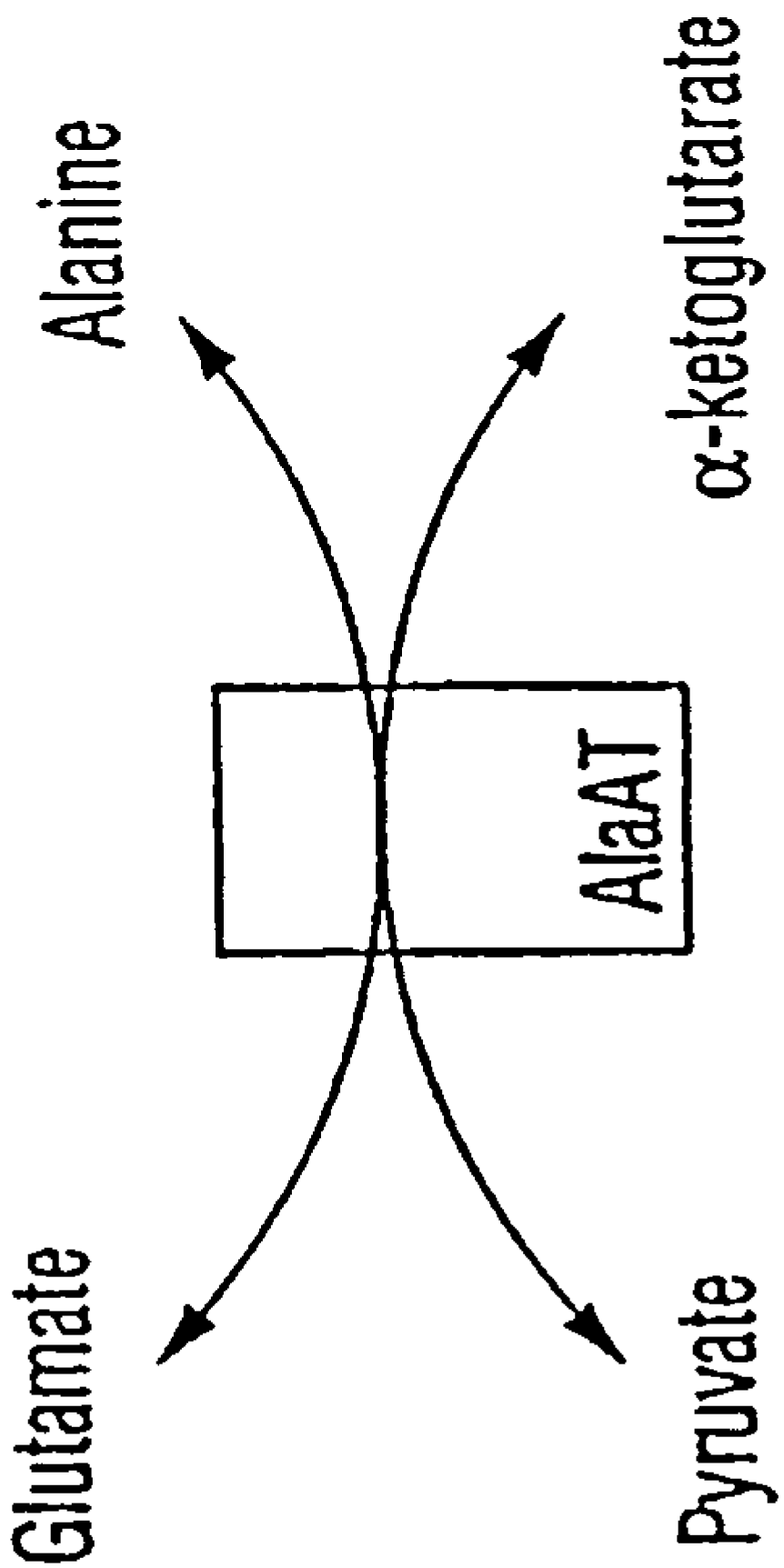
FIG. 2: Pathway for alanine biosynthesis by the enzyme alanine aminotransferase (AlaAT) (From Goodwin and Mercer, 1983).
Figure 6:
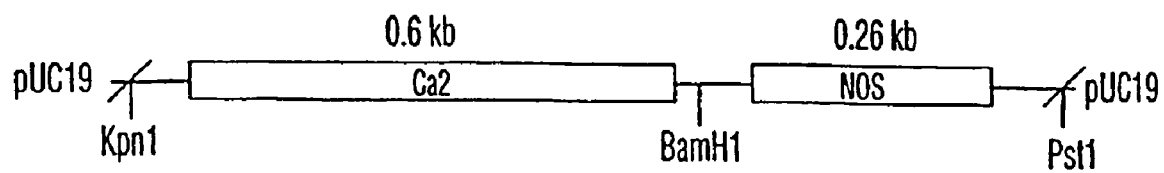
FIG. 6: Plasmid construct p25.

The barley AlaAT cDNA clone 3A (As shown in FIG. 5 and Muench and Good, ibid) was cloned into the pT7T3-19U vector (Pharmacia Canada) and used for site directed mutagenesis using two specific primers. Primer 1 introduced a BamH1 restriction site between nucleotides 48-53, while primer 2 was used to introduce a second BamH1 restriction site between nucleotides 1558-1563 (See FIG. 5). The 1510 bp fragment was then cloned into the vector p25 (FIG. 6) which had been cut with BamH1. p25 was a gift of Dr. Maurice Moloney (Univ. of Calgary, Calgary, Alta., Canada). This construct contains the double CaMV35S promoter, which has been shown to give high constitutive levels of expression, and NOS terminator inserted into the Kpn1 and Pst1 site of pUC19 with a BamH1, Xba1 and Pvu1 polylinker between the CaMV and NOS region of the plasmid. The resulting plasmid was called pCa2/AlaAT/NOS, as shown in FIG. 7A.

The plasmids ptrg-31/AlaAT/NOS and pbtg-26/AlaAT/NOS were created as follows. The trg-31 promoter was subcloned as a 3.0 kb Xba1/BamH1 fragment into the Xba1/BamH1 site of pCa2/AlaAT/NOS which had been digested with Xba1/BamH1 to release only the CaMV promoter, resulting in a 3 kb promoter fragment inserted in front of the AlaAT coding region. btg-26/AlaAT/NOS was created by inserting a BamH1 site at nucleotides +9 to +14 (see FIG. 3) and subcloning the 330 bp Kpn1/BamH1 fragment (from −320 to +10 in FIG. 3) into the Kpn1/BamH1 site of pCa2/AlaAT/NOS which had been digested to release the CaMV promoter. Plasmid constructs pbtg-26/AlaAT/NOS and ptrg-31/AlaAT/NOS and can be seen in FIGS. 7B and 7C, respectively.

Transformation and Aanalysis of *Brassica napus* Plants with AlaAT Constructs.

Figure 7A:
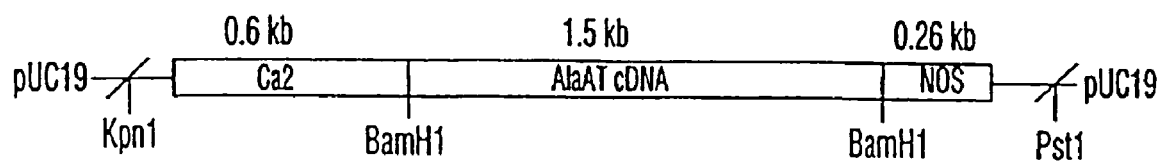
FIGS. 7A to 7C: Plasmid constructs containing the AlaAT coding region and the CaMV, btg-26 and trg-31 promoters that were used for the transformation of *Brassica napus* plants.
Figure 7B:
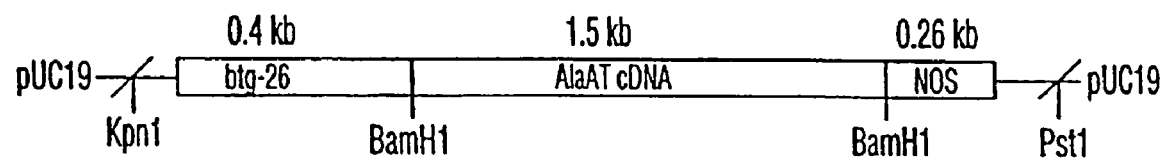
Figure 7C:
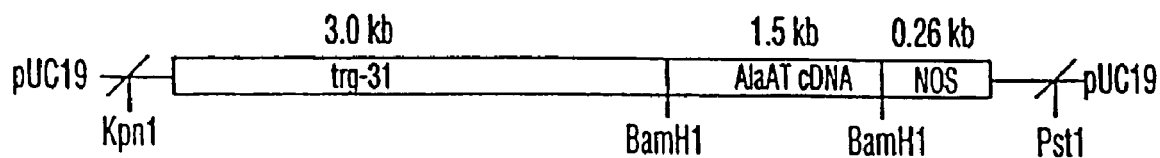
Figure 8:
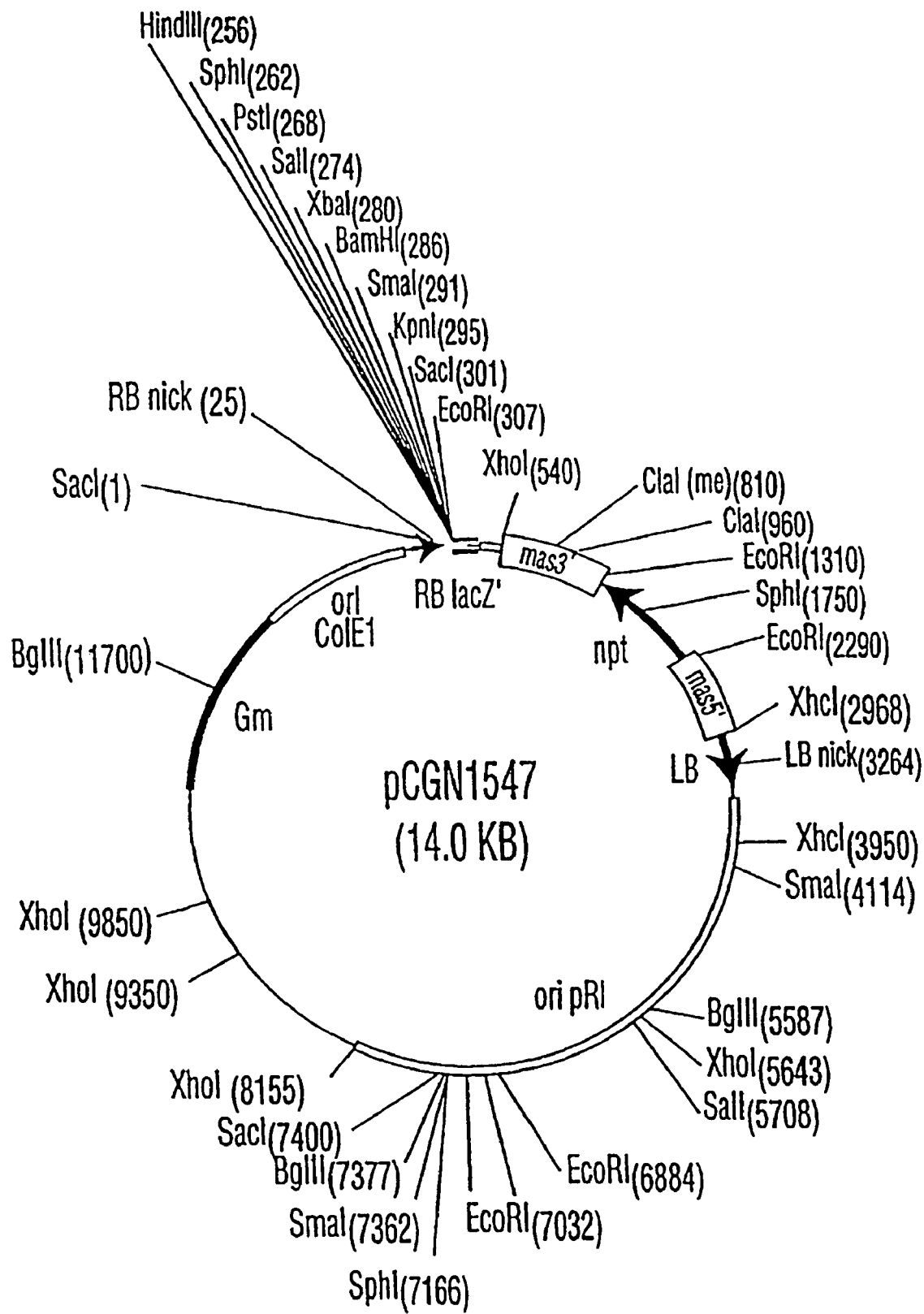
FIG. 8: Plasmid construct pCGN1547 used in producing the overexpressed/AlaAT or drought inducible/AlaAT transformants.

Once the three plasmids, as shown in FIGS. 7A, 7B and 7C, containing the AlaAT gene had been confirmed by restriction analysis and sequencing they were subcloned into the transformation vector pCGN1547 (FIG. 8). pCGN1547 is an *Agrobacterium* binary vector developed by McBride and Summerfelt (1990, Plant Mol. Biol. 14:269-276). pCGN1547 contains the neomycin phosphotransferase II (NPTII) gene which encodes Kanamycin resistance. These constructs were then introduced into the *Agrobacterium* strain EHA101 by electroporation using the protocol of Moloney et al. (1989, Plant Cell Reports 8:238-242). Confirmation that the *Agrobacterium* had been transformed with the pCGN1547 vector containing the specific construct was confirmed by polymerase chain reaction (PCR).

Transgenic plants were produced using a cotyledon transformation approach as described by Moloney et al. (ibid.). Kanamycin resistant plantlets were transferred to soil and then grown. The initial generation, or primary transformants, were referred to as the T0 generation and were allowed to self. Each subsequent generation was bagged to ensure selfing and referred to as the T1, T2 generation respectively. All putative T0 transgenic plants were tested for the insertion of the *Agrobacterium* construct using PCR primers that amplify the NPTII gene and by testing for NPTII activity as described by Moloney et al (ibid.).

Analysis of Transformed *Brassica* Plants Containing the AlaAT Constructs:

Transgenic plants were assayed for AlaAT activity as follows. Extractions were carried out on ice as described previously (Good and Crosby, 1989, Plant Physiol 90:1305-1309). Leaf tissue was weighed and ground with sand in a mortar and pestle in extraction buffer containing 0.1M Tris-HCl (pH 8.5), 10 mM dithiothreitol, 15% glycerol and 10% (w/v) PVPP. The extract was clarified by centrifugation at 6,000 rpm and the supernatant was assayed for enzyme activity. AlaAT assays were performed in the alanine to pyruvate direction as described previously (Good and Crosby, ibid) using alanine to start the reaction.

After transformation 20 Ca2/AlaAT/NOS, 24 btg-26/AlaAT/NOS and 21 trg-31/AlaAT/NOS plants were produced which appeared to be transformed, based on the amplification of an NPTII PCR product and NPT activity. AlaAT activity was measured, using the method described above, in the leaf tissue of several of these transformants. As can be seen from Table 1, the btg-26/AlaAT/NOS plants had AlaAT activity levels that ranged from 1.63 to 3.89 times that of the wild-type, control plants. Ca2/AlaAT/NOS plants had activity levels that ranged from 1.51 to 2.95 times that of wild-type, control plants. Western blots confirmed that the transgenic plants had elevated levels of AlaAT, based on the cross reactivity of a band with the barley AlaAT antibody (not shown).

TABLE 1

Alanine aminotransferase (AlaAT) activity in primary transformants

| Plant | Activity* |
|---|---|
| btg-26/AlaAt/NOS | |
| transformant #4 | 3.89.times. |
| transformant #5 | 1.63.times. |
| transformant #7 | 1.93.times. |
| transformant #8 | 1.98.times. |
| transformant #18 | 1.63.times. |
| Ca2/AlaAT/NOS | |
| transformant #1 | 1.51.times. |
| transformant #2 | 2.77.times. |
| transformant #6 | 1.61.times. |
| transformant #7 | 2.95.times. |
| transformant #9 | 2.14.times. |
| transformant #12 | 1.91.times. |
| transformant #13 | 1.77.times. |

*Enzyme activity is expressed relative to wild type controls

Example 3

Growth of Primary Transformants Under Normal Conditions

T1 seed from the primary transformants of the groups CaMV/AlaAT and btg-26/AlaAT were grown along with control, wild-type plants under normal conditions including planting at a 1 cm depth in 13 cm diameter plastic pots containing a soil and fertilizer mixture as described by Good and Maclagan (ibid.). These pots were placed in growth chambers under the following conditions: i) 16 h of 265 mmol $m^{-2} s^{-1}$ provided by VITA-LITE U.H.O. fluorescent tubes, ii) day and night temperatures of 21° C. and 15° C. respectively, iii) relative humidity of 85%-97% and iv) daily watering with ½ strength Hoagland's solution. The only observable difference observed between the plants was the btg-26/AlaAT plants had thicker stems when compared to the controls and CaMV/AlaAT plants. No significant differences were observed between the three groups in terms of growth rate, plant or leaf size or leaf senescence at identical time points, time to maturity, seed size or seed yield.

Example 4

Growth of Primary Transformants Under Nitrogen-Starved/Drought Conditions

Figure 9:
FIG. 9: *Brassica napus* plants grown under nitrogen starved conditions for three weeks followed by drought for 3 days. The plants are identified as A, B and C, as follows: Plant A is a control, wild-type plant; Plant B contains a CaMV/AlaAT construct; and Plant C contains a btg-26/AlaAT construct.

T1 seed from the primary transformants of the CaMV/AlaAT and btg-26/AlaAT groups were grown along with control, wild-type plants for four weeks under normal conditions (as noted above) and then subjected to nitrogen starvation, by watering with only water for three weeks, followed by drought for 3 days. FIG. 9 shows representative plants from the three groups after the treatment at identical time point. Plant A is a control, wild-type plant; Plant B is a CaMV/AlaAT transformed plant; and Plant C is a btg-26/AlaAT plant. It can be seen that plant C (btg-26) clearly has a faster growth rate than plants A (control) and B (CaMV/AlaAT). In addition, senescing leaves (indicated by arrows) are present on plants A and B while plant C has no senescing leaves. In summary, the following were observed in the treated btg-26/AlaAT plants when compared to the treated CaMV/AlaAT and control plants: faster growth rate; larger plants at similar time points, less senescence in the lower leaves; earlier maturity; thicker stems; larger seeds; and higher seed yields.

Example 5

Tissue-Specific Expression of Genes Utilizing the btg-26 Promoter

To determine whether genes under the regulatory control of the btg 26 promoter were expressed in a tissue-specific manner, experiments were performed in which the levels of the expressed protein product of a transgene placed under the control of the btg 26 promoter were measured in either the shoot or root of a transgenic plant containing the btg 26 construct. Both a reporter gene (GUS) and a functional gene of interest (AlaAT) were utilized, and the expression of their respective protein products in either the shoot or root of transgenic plants was determined both qualitatively and quantitatively.

Production of btg-26/GUS Transgenic Plants

Plants expressing the reporter gene GUS under the regulatory control of the btg-26 promoter were produced. First, a btg 26/GUS plasmid was created by inserting a 300 bp KpnI/BamHI btg 26 promoter fragment into the KpnI/BamHIi site of pBI101 which had been digested to release the CaMV promoter. This plasmid was then subcloned into the transformation vector pCGN1547 which was introduced into the *Agrobacterium* strain EHA101 by electroporation using the protocol of Moloney et al. (ibid). Confirmation that the *Brassica* plants had been transformed was obtained by a) PCR amplification of the NPTII gene coding for neomycin phosphotransferase and by b) testing for NPTII activity as described by Moloney et al. (ibid). Transgenic plants (T0) were allowed to self and then T1 plants selfed to produce T2 seed. The T2 seed was tested using a Kanamycin resistance assay (Moloney et al. 1989, supra) to ensure the seed was homozygous.

GUS Staining of btg 26/GUS Transgenic Lines In Vivo

Figure 10:
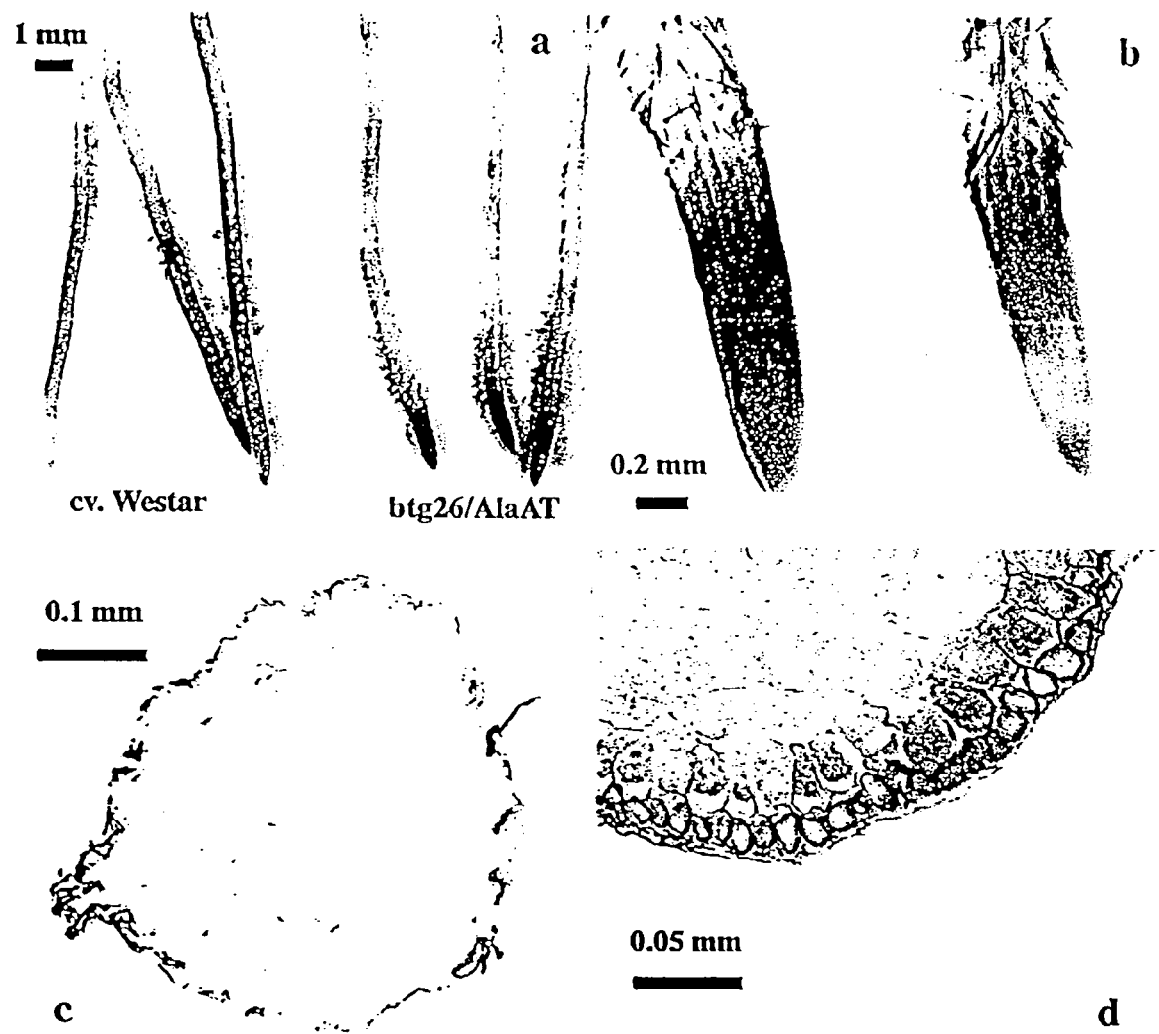
FIG. 10: GUS in vivo staining of btg 26/GUS transgenic plants. Panel A shows wild-type plants on the left and transgenic plants on the right. Panel B shows the root tips of stained transgenic plants. Panel C shows a cross-section of the absorption zone of the root tips of the transgenic plants. Panel D shows a cross-section of the division zone of root tips of the transgenic plants.

To determine the tissue distribution of expression of the GUS gene from the btg 26/GUS construct within the transgenic plants described in the previous section, the activity of GUS in different tissues was ascertained by the utilization of a calorimetric reaction, the results of which could be visually assessed. Plants were germinated and grown hydroponically in sterile conditions in modified Long Ashton media (Savidov et al. 1998) in Magenta jars, which were bubbled with air. Five-week-old plants were stained for in vivo GUS activity by replacing the ms media with 50 mm phosphate buffer (ph 7.5) containing 0.2 mm X-gluc (5-boromo-4-chloro-3-indolyl-beta-glucuronic acid) and incubating the plants in this media for 24 hours. Root tissue was then viewed under a dissection microscope at the magnification indicated and photos were taken. As shown in FIG. 10, the btg 26 promoter directs expression of a reporter gene (GUS) in the root hairs (panel B), and a single layer of epidermal cells in the roots (panels C and D). Moreover, the promoter directs expression in the root tip, the cell division area and the area of cell expansion (panels A-D).

GUS Staining of btg-26/GUS Transgenic Lines in Vitro

Figure 11:
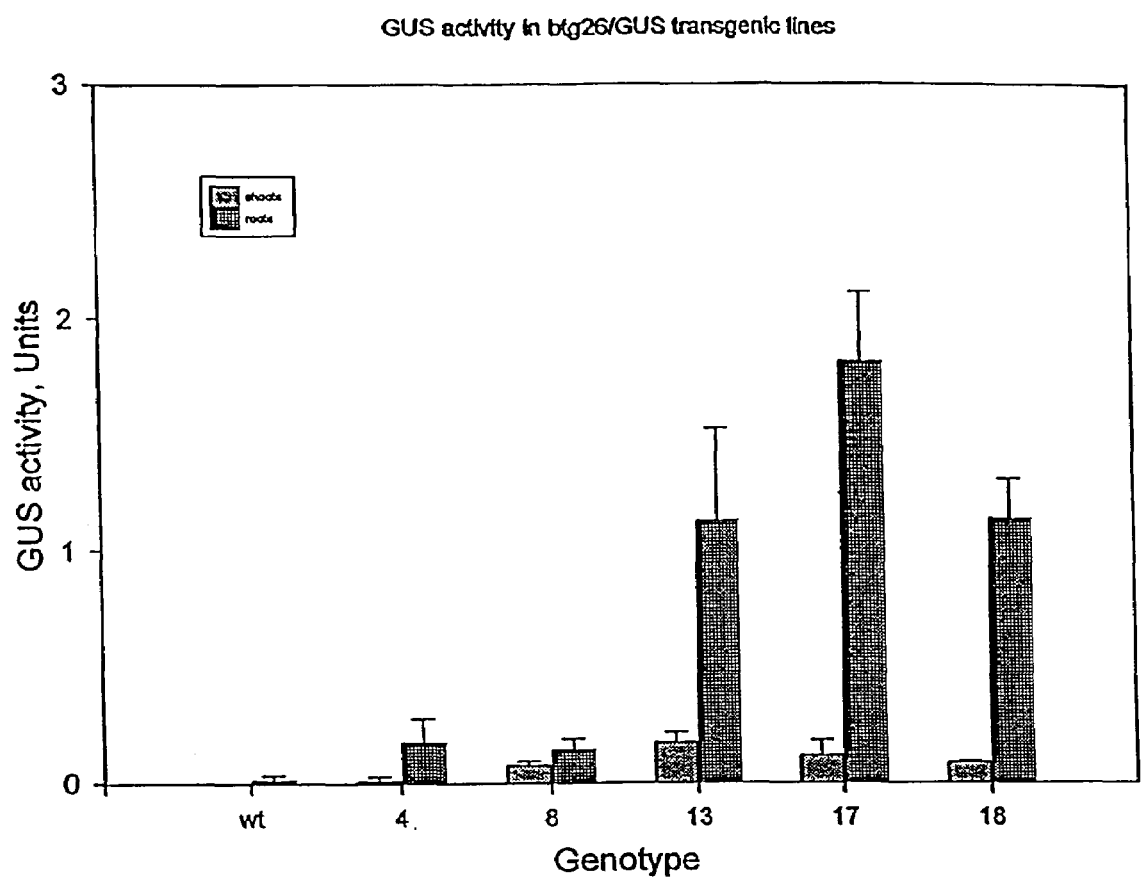
FIG. 11: GUS activity in shoots versus GUS activity in roots of btg 26/GUS transgenic plants. This figure shows a bar graph of the amount of GUS activity present in extracts of root and shoot from plants expressing the btg 26/GUS transgene, and the root:shoot ratio of GUS activity in these plants.

The above-described staining assay permitted a qualitative, visual analysis of the expression pattern of the btg 26/GUS construct in different tissues of the transgenic plant. To obtain a quantitative analysis of the tissue distribution of btg 26-directed expression, the levels of GUS activity in different tissues of the transgenic plant were also measured. Plants were grown as described above (GUS staining of btg 26/GUS transgenic lines in vivo), and the tissue was harvested and ground in GUS assay buffer. The in vitro GUS activity was measured as described by Gallagher, S. R. (1992) GUS Protocols: Using the GUS Gene as a Reporter of Gene Expression. Academic Press: New York, ISBN 0-12-274010-6. As is shown in FIG. 11, the btg 26 promoter directs expression of a reporter gene (GUS) in the root tissue significantly more strongly than in the shoot (leaf) tissue (between about two-fold and about 20-fold more strongly).

Differential Expression of the AlaAT Transgene in the Roots and Leaves of btg 26/AlaAT Transgenic Lines To determine whether the btg 26/AlaAT construct described previously is expressed in a tissue-dependent manner similar to that of the btg 26/GUS construct, the expression of AlaAT in root and leaf tissue of transgenic plants was assessed by reverse transcripts-PCR (RT-PCR). This methodology permits sensitive detection of the presence of AlaAT mRNA, and, coupled with densitometric methods, permits the quantitation of the translated product in a given tissue of the transgenic plant.

Figure 12:
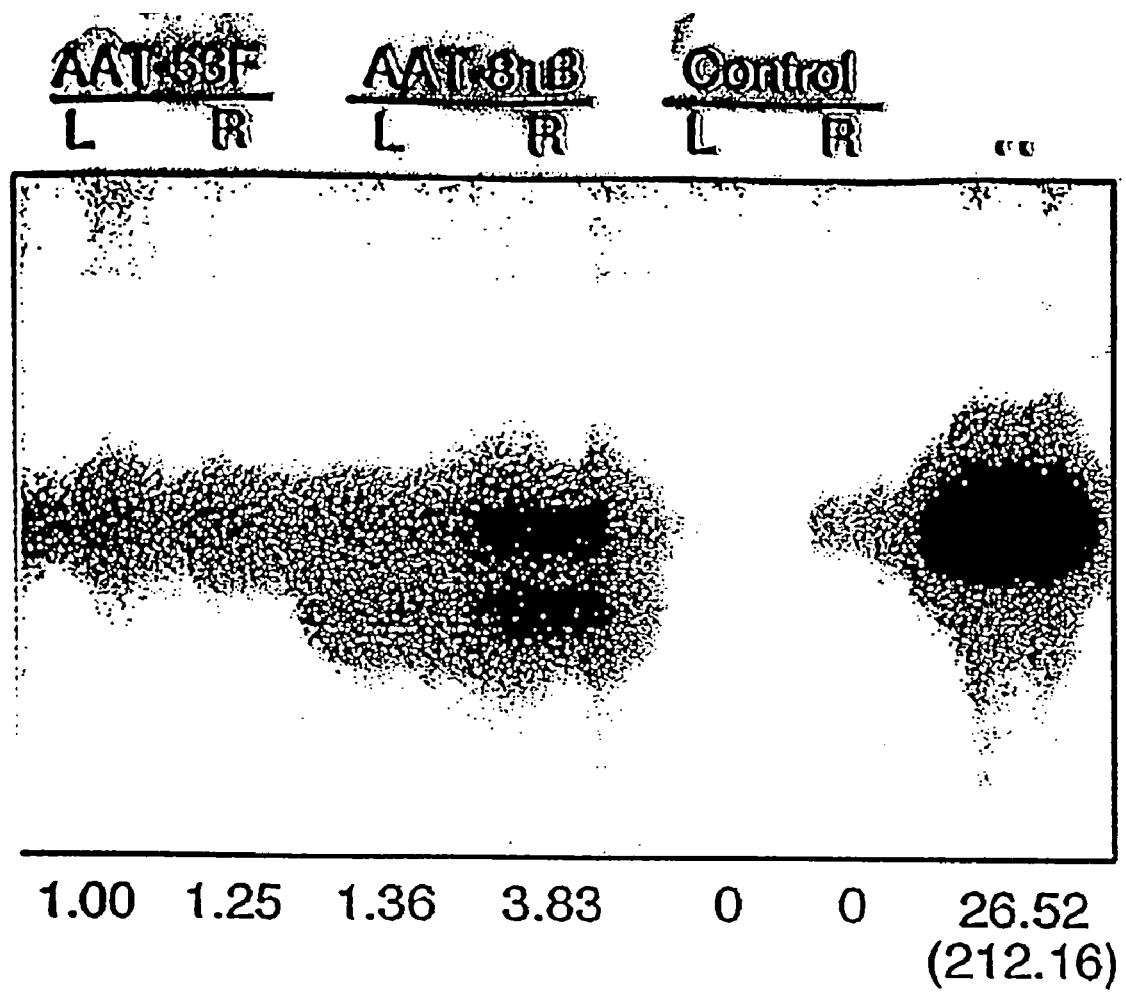
FIG. 12: Southern blot analysis of RT-PCR reactions amplifying AlaAT from leaf (L) and root (R) total RNA. Relative densitometric analysis of the 381 bp product of the RT-PCR reaction is indicated below each lane.

Differential expression of the AlaAT transgene in the roots and leaves of btg 26/AlaAT transgenic lines was confirmed using RT-PCR as per normal molecular protocols. FIG. 12 is a southern blot analysis of RT-PCR products from leaf and root RNA. Leaf tissue was harvested from 5-week-old plants grown as described above (GUS staining of btg 26/GUS transgenic lines in vivo) whereas root tissue was harvested from plants grown as described below (Differential expression of the AlaAT transgene in the root tissue of the btg 26/AlaAT transgenic lines). Primers amplified a 381 bp product at the 5' end of the AlaAT transgene and a 311 bp product which has no homology to the AlaAT cDNA. Based on the relative densitometry of the 381 bp product (indicated below each lane in FIG. 12), it is apparent that the btg 26 promoter directs expression of the transgene preferentially (1.25-2.8 fold greater expression) in root tissue in those transgenic lines which display the N-efficient phenotype (and hence are known to be expressing the AlaAT protein product).

Differential Expression of the AlaAT Transgene in the Root Tissue of btg 26/AlaAT Transgenic Lines Visual confirmation of the above results was achieved by immunolocalization of the AlaAT protein product in root tissues of plants containing the btg 26/AlaAT construct. Plants were grown hydroponically in modified Long Ashton media (Savidov et al. 1998 Plant Sci. 133:33-45) in a growth chamber (18 degrees C., 350 uE, 16 h light/8 hours). The roots were excised after 5 weeks and stained using an AlaAT antibody. Staining involved imbedding roots in paraffin, sectioning with a microtome and then using an AlaAT-specific antibody (Muench, D. G. and A. G. Good (1994) Plant Mol. Biol. 24:417-427) and a peroxidase goat anti-rabbit secondary antibody as per normal immunolocalization protocols.

Figure 18:
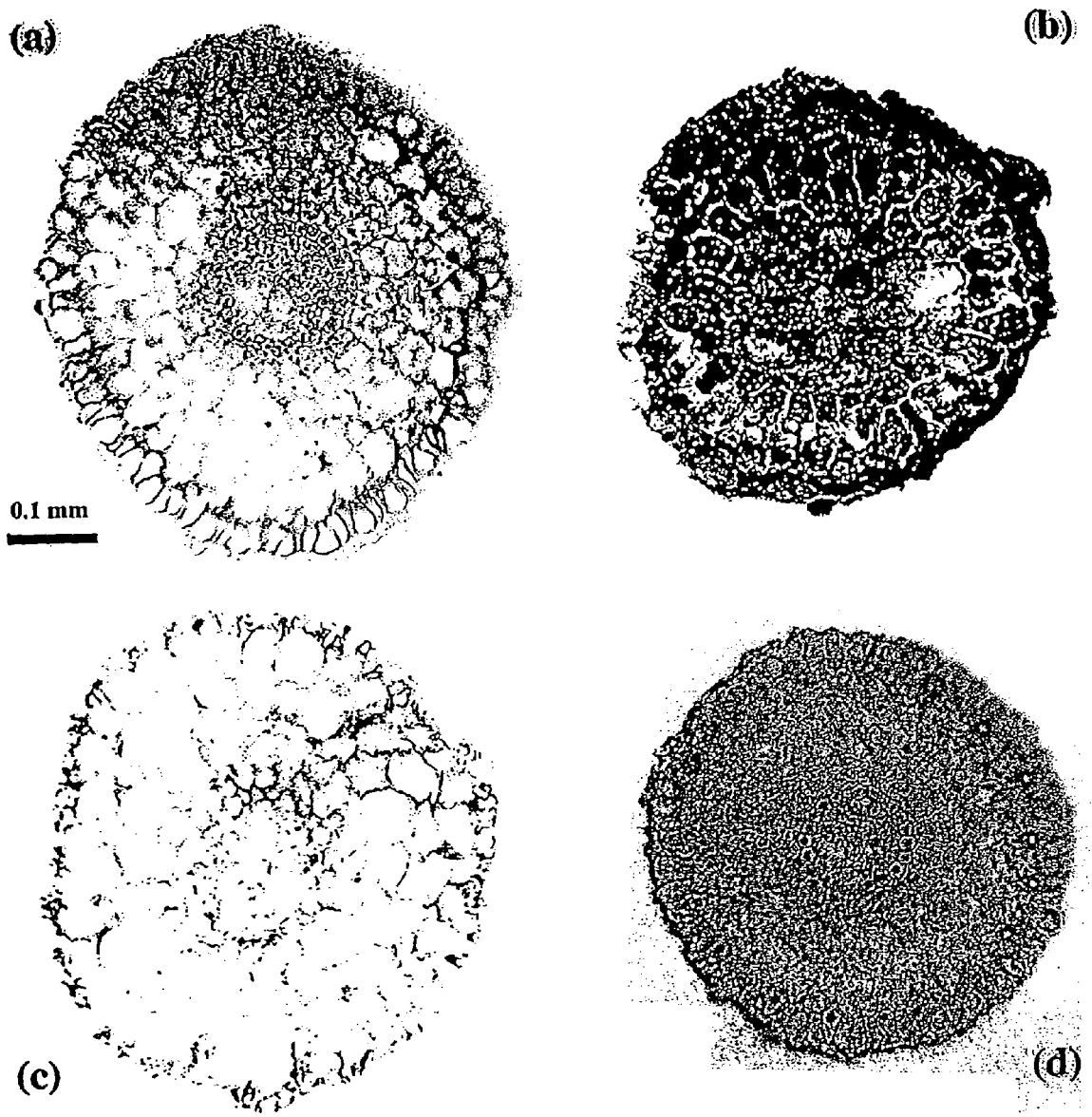
FIG. 18: Immunolocalization of expressed AlaAT protein in wild type and transgenic (btg 26/AlaAT) plants. Panel A shows control wild-type untreated root, panel B shows transgenic untreated root, panel C shows wild-type root treated with 150 mM NaCl, and panel D shows transgenic root treated with 150 mM NaCl.

Specifically, tissues were fixed in FAA (50% ethanol, 5% acetic acid, 10% formalin), dehydrated in tert-butanol, and embedded in paraffin. Sections 10 microns in thickness were deparaffinized in xylenes, were subsequently rehydrated, and were blocked with PBS containing 3% non-fat dry milk for 3 h. The sections were mounted on glass slides that were coated with poly-L-lysine to promote adhesion. The antibody was diluted 1:100 in PBS, and this diluted antibody was incubated with the slide-mounted sections for 1 h. Post incubation, these tissue sections were washed extensively with PBS. Tissue sections were subsequently incubated for 1 h with anti-IgG secondary antibody (diluted 1:300 in PBS) conjugated to alkaline phosphatase. Color development was in AP buffer (100 mM Tris-HCl, pH 9.5, 100 mM NaCl, 5 mM MgCl2) using 5-bromo-4-chloro, 3-indolylphosphate (BCIP) (0.005% (w/v) and nitroblue tetrazolium (NBT) (0.01% (w/v)) as substrates. Developed sections were dehydrated and mounted. As is shown in FIG. 18, the btg 26/AlaAT plants expressed the AlaAT gene in a similar fashion to that seen in the btg 26/GUS transgenic plants; the tissue-specific pattern of expression was identical (see FIG. 18).

Figure 13:
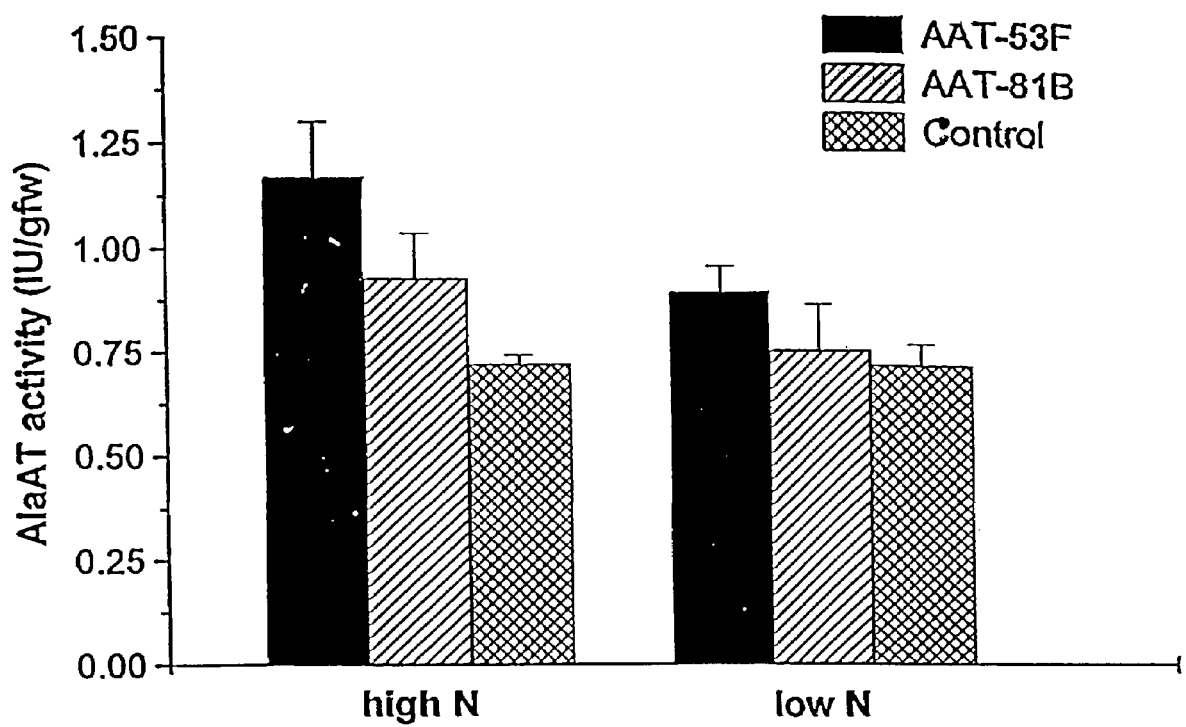
FIG. 13: Transgenic (btg 26/AlaAT) and control (wild-type) leaf AlaAT activity under low and high nitrogen conditions.

Differential Expression of the AlaAT Transgene in Leaf Tissue of the btg 26/AlaAT Transgenic Lines The tissue-specific expression of the AlaAT transgene in leaves of transgenic plants containing the btg 26/AlaAT construct previously identified by RT-PCR (see above) was confirmed by use of spectrophotometric assays measuring the enzymatic activity of AlaAT in leaf extracts from transgenic and control plants. Plants were grown in a standard potting mixture (sand, peat moss, soil and slow release fertilizer, N/P/K), with or without supplementary nitrogen treatment. Plants were grown for 5 weeks in a growth chamber under standard conditions and FW, DW, leaf area and stem diameter were measured. Leaf proteins were extracted by grinding leaf tissue (0.2 gm/ml) in a mortar and pestle in extraction buffer (0.1 m Tris-HCl, ph 8.0, containing 10 mm DTT and 10% (v/v) glycerol). AlaAT activity was assayed spectrophotometrically essentially as described (Good and Muench, supra). The reaction mix contained 5 mM 2-oxoglutarate, 0.1 mM NADH, 100 mM Tris-HCl (ph 8.0), 5 units of LDH (Sigma L1254), and 20 µl of enzyme extract to a final volume of 1 mL. The reaction was started by the addition of 25 mM alanine, and the absorbance change was measured at 340 nm at 21° C. As is seen in FIG. 13, the btg 26/AlaAT transgenic plants have higher levels of AlaAT activity in leaf tissue.

Differential Induction of the AlaAT Transgene in Shoots and Roots Using Salt

Figure 14:
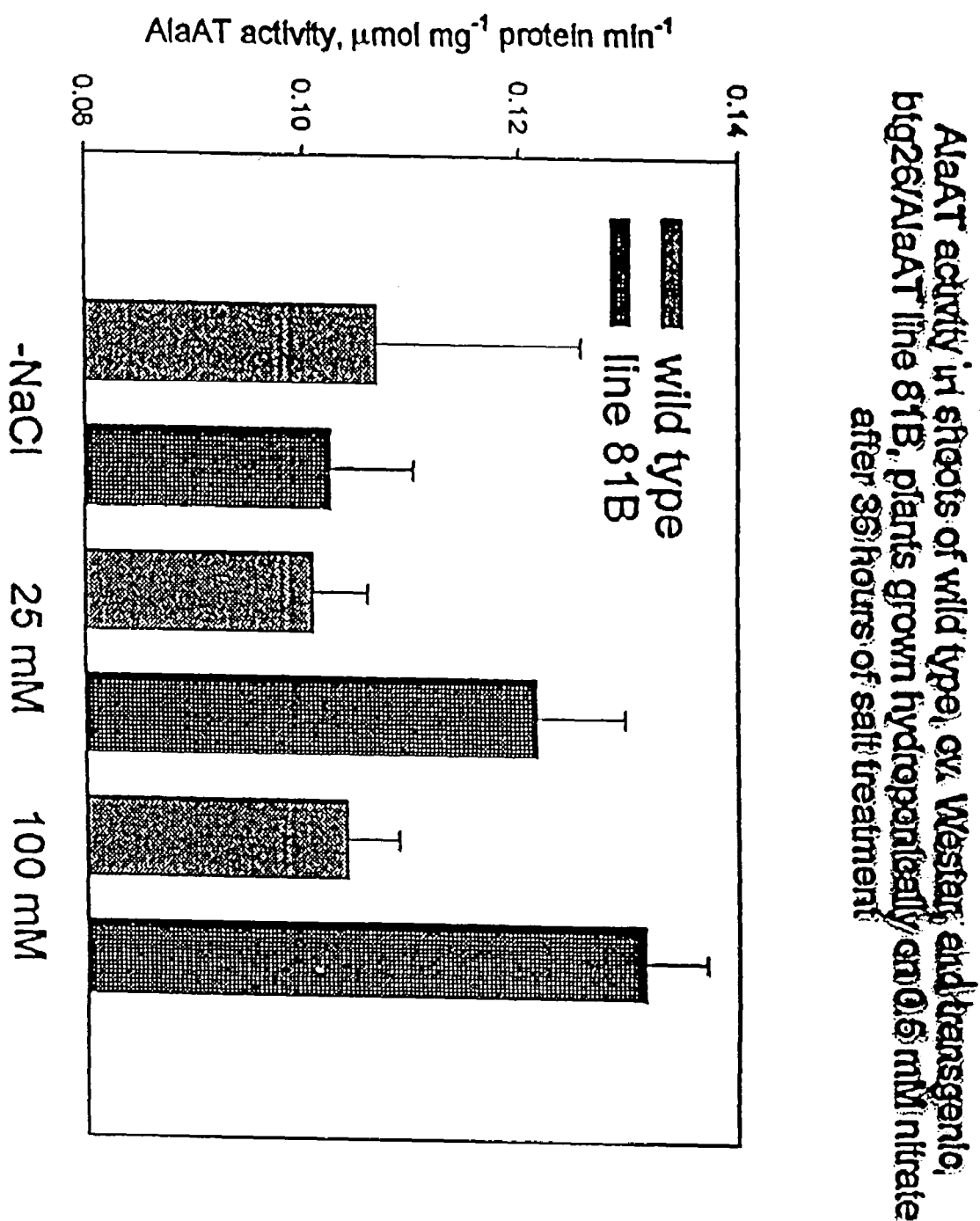
FIG. 14: AlaAT activity in shoots of wild-type, cv. Westar, and transgenic btg 26/AlaAT line 81B plants grown hydroponically with 0.5 mM nitrate after 36 hours of salt treatment.
Figure 15:
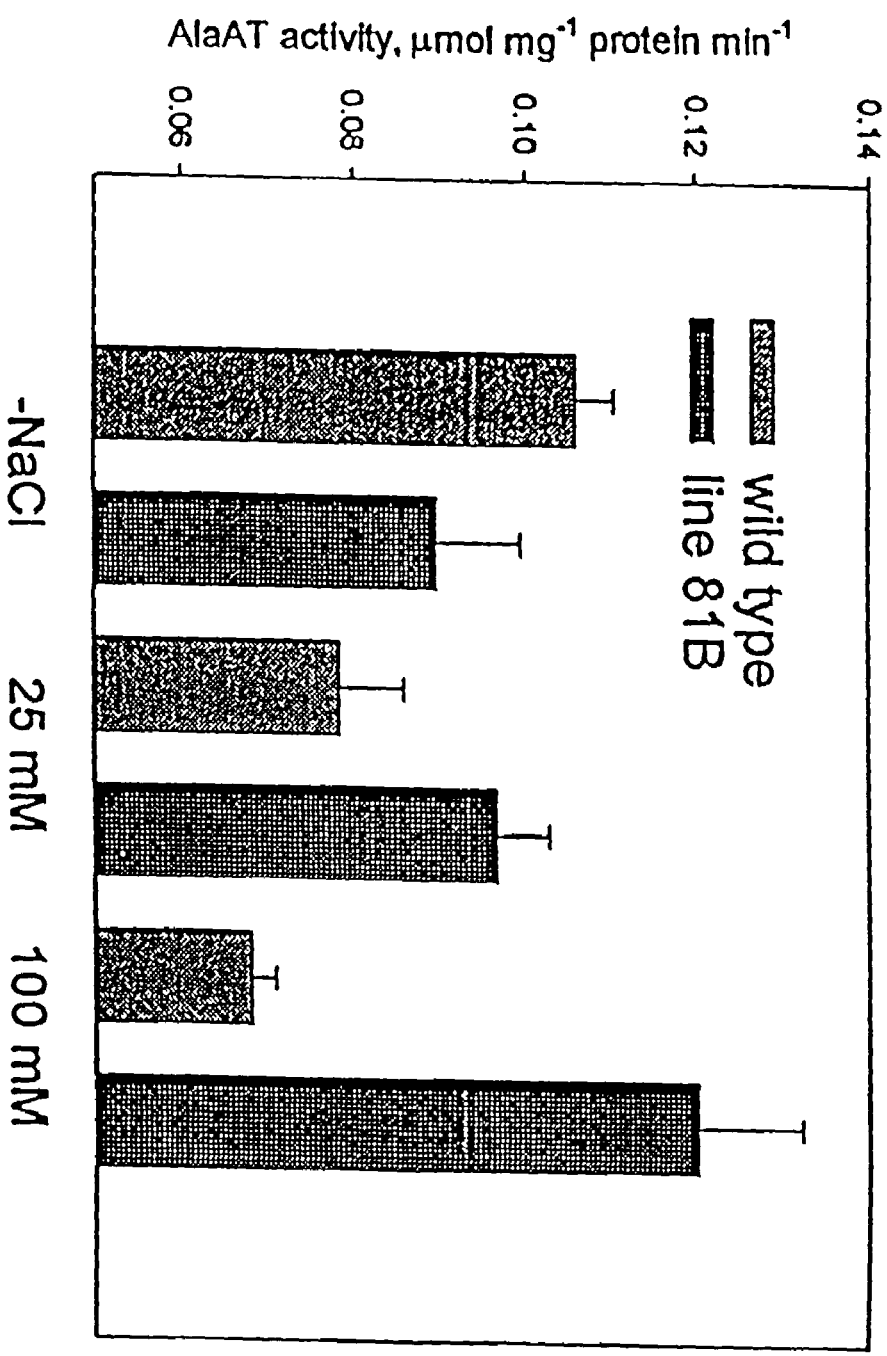
FIG. 15: AlaAT activity in roots of wild-type, cv. Westar, and transgenic btg 26/AlaAT line 81B plants grown hydroponically with 0.5 mM nitrate after 36 hours of salt treatment.

It had been demonstrated (Example 1) that the expression of genes under the control of the btg 26 promoter could be switched on by treatment with NaCl, in a concentration-dependent manner. To determine whether the tissue-specific expression of AlaAT in plants transgenic for the btg 26/AlaAT construct could also be effected by a saline treatment, the following experiment was performed. Plants were grown hydroponically in a modified Long Ashton's nutrient solution containing 0.5 mM nitrate within growth chambers in 60 liter tanks. After 4 weeks of age, differing concentrations of salt were added to the media and the level of AlaAT activity was measured 36 hours after the addition of NaCl, as described by Good and Muench (1992, ibid). The results are shown in FIGS. 14 and 15. Whereas in wild-type shoots or roots, saline-treated plants display decreased AlaAT activity from the untreated controls, the saline-treated btg 26/AlaAT transgenic shoots or roots both display significant increases in AlaAT activity over untreated controls (see, e.g., FIG. 18). This demonstrates that the expression of the AlaAT gene can be switched on in root and shoot tissue by the addition of an inducing compound, in this case NaCl.

Figure 16:
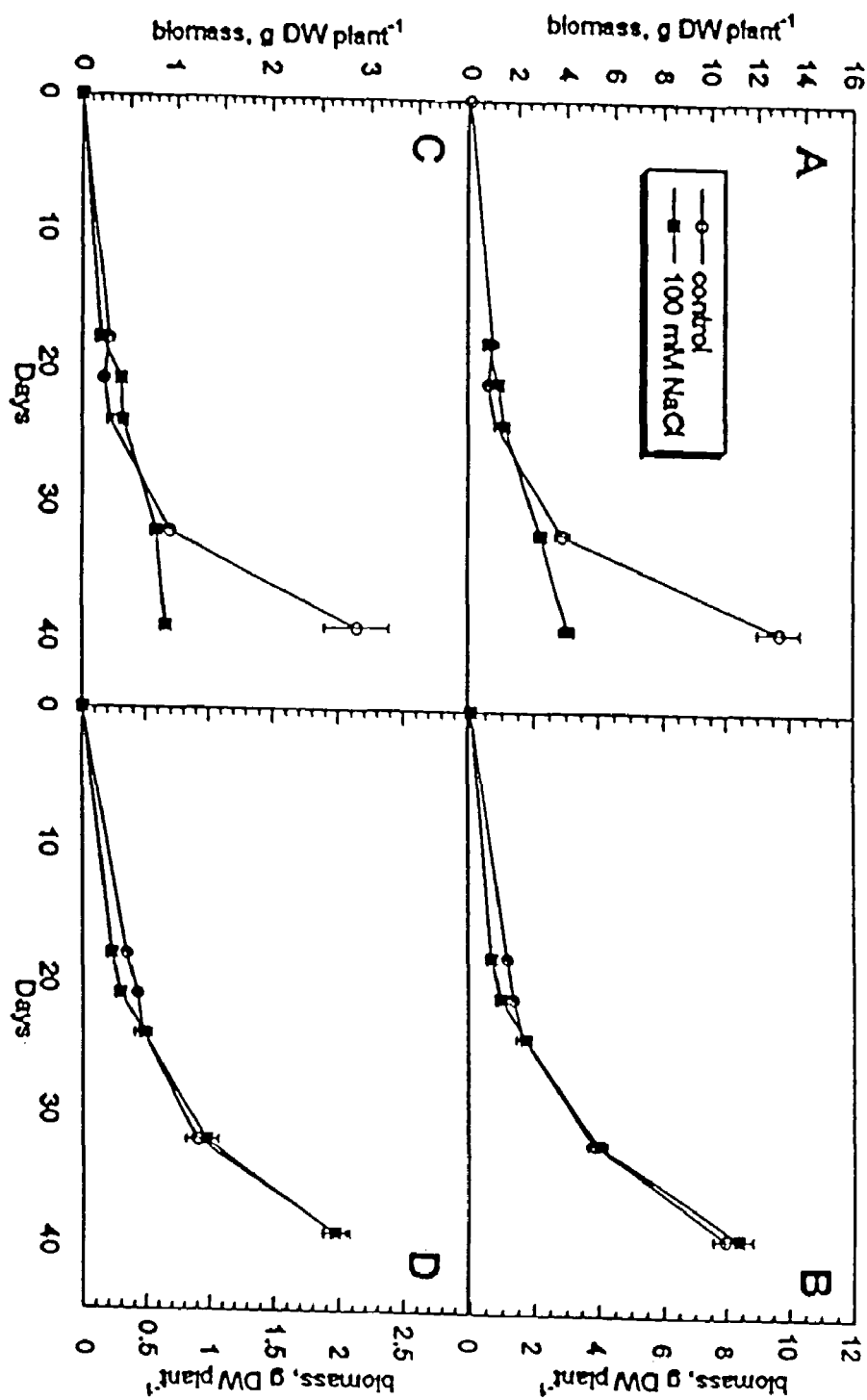
FIG. 16: Effect of salinity on biomass accumulation of wild type, cv. Westar, and transgenic, btg 26/AlaAT, line 81B plants. Panel A shows wild-type shoots, panel B shows btg 26/AlaAT shoots, panel C shows wild-type roots and panel D shows btg 26/AlaAT roots.
Figure 17:
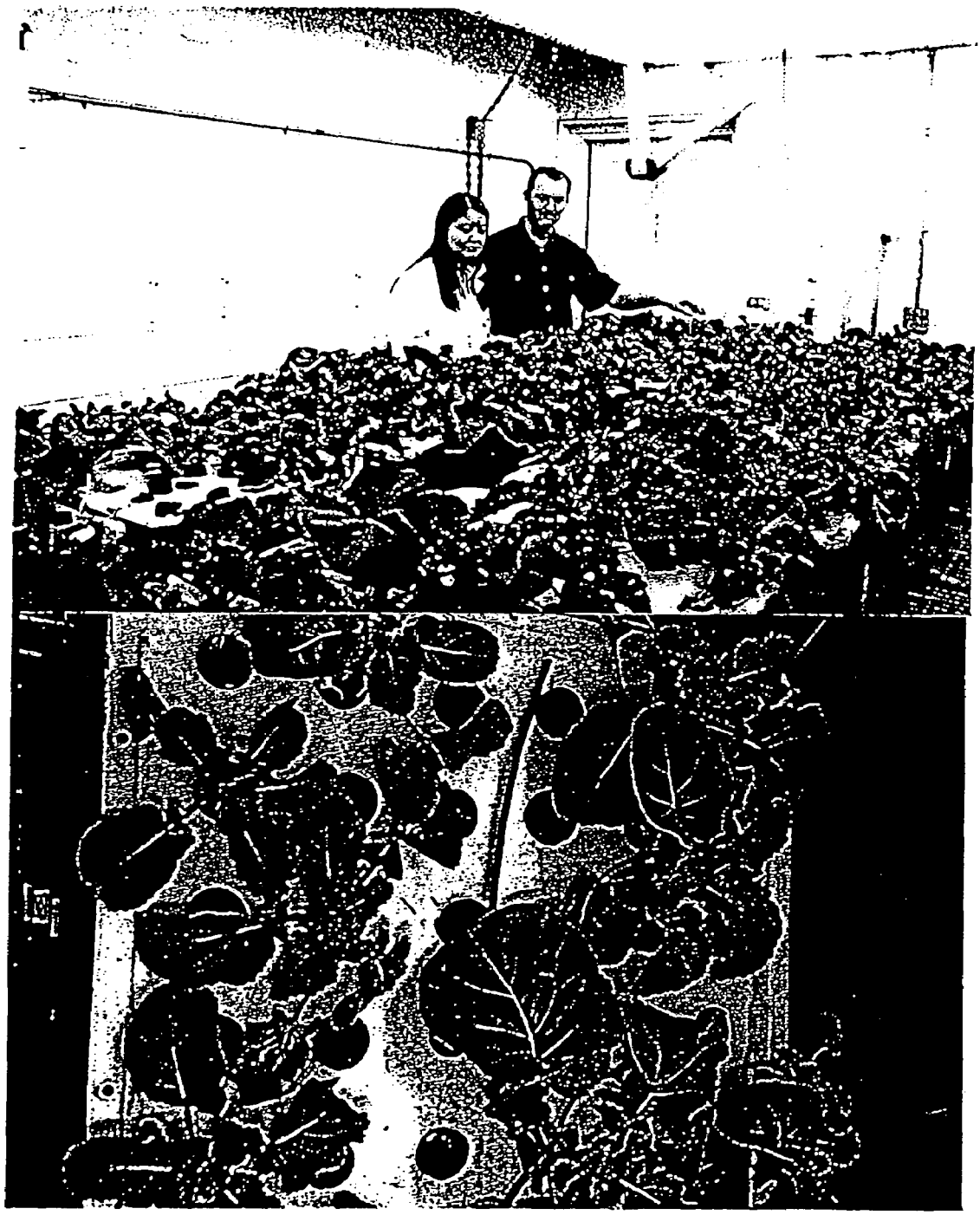
FIG. 17: Effect of salinity on the growth of wild-type, cv. Westar, and transgenic, btg 26/AlaAT, line 81B plants. Wild-type plants are on the left side of the picture, and transgenic plants are on the right side of the picture.

Differential Expression of the AlaAT Transgene, when Induced by Salt, Results in Enhanced Growth Rates Compared to the Untransformed Controls It had been previously ascertained (Example 4) that plants carrying the btg 26/AlaAT construct were visually improved in growth over control plants under conditions of nitrogen starvation or drought. The above-recited results demonstrated that AlaAT expression as directed by the btg 26 promoter is tissue-specific not only to shoots (see FIG. 14), but also to roots (see FIG. 18). Experiments were performed to quantitatively determine whether direct treatment of transgenic plants containing the btg 26/AlaAT construct with NaCl results in a similar growth effect in one or both of the plant tissues demonstrated to have significant AlaAT expression (e.g., shoot and root). Plants were grown hydroponically in growth chambers in 60 liter tanks (as described above) in a modified Long Ashton's nutrient solution containing 0.5 mM nitrate. After 4 weeks of age, differing concentrations of salt were added to the media and the fresh weight and dry weight of the roots were measured. As is shown in FIG. 16, there is enhanced growth (as measured in biomass) in plants expressing the AlaAT gene in root tissue (panels B and D) by the addition of an inducing compound (such as NaCl) as compared to wild-type control plants under similar conditions (panels A and C). This growth effect is sufficiently significant as to be visually apparent (FIG. 17); the btg 26/AlaAT plants treated with 100 mM NaCl for 2 weeks after 4 weeks of age shown on the right side of the figure are visually improved in growth over the wild-type plants treated under the same conditions, shown on the left side of the Figure.

Example 6

Field Trials of Nitrogen Utilization Protein—Transformed Canola

1. Experimental Factors and Treatments

Field trials were conducted at Brawley Calif. (32.59° NL; 115.30° WL) in the crop season 2002-2003, to test three genotypes at four fertilization levels of nitrogen supplied with two different N sources. Taking the practicality of fertilizer application into consideration, field experiments were split into the two trials based on nitrogen fertilizer sources: ammonium nitrate-N trial and urea-N trial. Each trial included the two factors, genotypes (g=3) of two different NUE-transgenic lines and canola check cv. Westar (wild type), and nitrogen fertilization at four levels (n=4). The total number of treatments of the trial was n×g=12. Each treatment was replicated for five times (r=5). Therefore, the total number of experimental units was 60 plots. The factors and treatments are described in Table 1.

TABLE 1

Description of factors and treatments of field trials in Brawley over the crop season 2002-2003.

| Factor | TREATMENT | Description of treatment levels |
|---|---|---|
| Genotype | 3 | BNAT-041 NUE-transgenic line, double insertions of the gene AlaAT BNAT-043 NUE-transgenic line, single insertion of the gene AlaAT |

TABLE 1-continued

Description of factors and treatments of field trials in Brawley over the crop season 2002-2003.

| Factor | TREATMENT | Description of treatment levels |
| --- | --- | --- |
| Nitrogen level | 4 | cv. Westar Wild type as check Application of nitrogen as either ammonium nitrate or urea Level 1: 0 lb N/ac (control) Level 2: 50 lb N/ac (suboptimal) Level 3: 150 lb N/ac (optimal) Level 4: 250 lb N/ac (super-optimal) |

2. Experimental Design

The field trials employed a split-plot design. This assigned the four levels of nitrogen factor into main plots and the three lines of genotypic factor into subplots, respectively. All treatments of either main plots or subplots within each main plot were arranged in a completely randomized fashion. The trials would benefit from this split-plot design both in field practicality and in statistical analysis. Splitting plots based on amount of nitrogen application could facilitate to precisely implement N treatments in field plots and to exclude the fertilizer drift between different levels. In statistics, the split-plot design can improve the precision for comparing the average effects of NUE-transformed lines and wild type cv. Westar assigned to subplots and, when interactions exist, for comparing the effects of subplot treatments for a nitrogen supplementation level. In general, experimental error for main plots is a lot larger than the experimental error that is used to compare subplot treatments (Little and Hills, 1978).

3. Field Layout and Implementation of Trials

Prior to field layouts of the trials, six spots evenly distributed over the trial zones were sampled and tested to understand the mode and gradient of soil variability. Soil samples were taken separately at three depths (0-12, 12-24, and 24-36 inches) for elemental analyses such as total nitrogen, nitrate nitrogen ($NO_3$—N), ammonium nitrogen ($NH_4$—N), reactive phosphorus ($P_2O_5$—P), potassium (K), sulfur (S), boron (B), calcium (Ca), magnesium (Mg), and other micro-nutrients (iron, zinc, copper, manganese, sodium). Soil physical properties were also measured for each soil layer, such as soil texture, bulk density, pH, and electrical conductivity.

In the field, each trial plot had a size of 7.43 $m^2$ (i.e. 80 $ft^2$) in rectangular shape. It consisted of the two seedbeds, 3.66 m (12 ft) long and 1 m (3.3 ft) apart. Each seedbed contained the seed rows, about 0.33 m (1.1 ft) apart. To prevent possible drift effects of different N levels, there was 2 m space between main plots and 1 m space between subplots. In addition, areas surrounding the entire trial zone were grown with canola cv. Quatum to exclude the border effects. Seeding rate of each genotype was adjusted in terms of seed purity test, 1000-seed weight, and germination rate, to ensure a uniform plant density. Hand weeding within subplots and chemical weeding in border spaces by the use of Roundup® were carefully and periodically practiced throughout the crop season.

Fertilizers were applied in early spring (mid January), at the transition period from plant rosette stage to initial bolting and budding. Only one application was made over the crop season, based on the following fact. At pre-planting, soil tests indicated that a quite high level of nitrogen was available in the soil, with an average of 170.2 lb N/ac at depth 0-36". Since excess N applied in the fall could be lost prior to uptake due to very limited nitrogen requirements from young seedlings, nitrogen application at pre-planting appeared to be unnecessary. Nitrogen levels were precisely implemented for each main plot, by evenly injecting fully dissolved fertilizer solutions into the two sides of each seedbed. Prior to nitrogen application, boric acid ($H_3BO_3$) at 1 lb B/ac and simplot ($P_2O_5$) at 40 lb P/ac were evenly applied to the entire trial zone, to exclude the effects from possible deficiencies of these two nutrients based on soil tests.

4. Data Collections 4.1 Assays for Plant Growth and Development

As described in Table 2, plant growth and development was periodically monitored at different growth stages. From Block 5 of each trial, one-foot plants within each subplot were randomly sampled at pre-fertilization, initial flowering, seed filling, and maturity stage, respectively. Sampled plants were divided into tissue components, such as roots, leaves, shoots, buds and flowers, and siliques, dependent upon growth stages. For all the parts, fresh weight was determined immediately in the field and dry weight measured by oven drying samples to constant weight at 77° C. for 48 hrs. Then, biomass yield at defined growth stage, and partitioning of dry matter as well as nitrogen uptake in the plant for each subplot, were determined.

TABLE 2

Observations of plant growth and development.

| Category | Items of investigation or analysis |
| --- | --- |
| Plant density | Number of plants per foot. |
| Plant growth vigor | Plant height, stem diameter at the basal section, maximal canopy width, number of primary branches. |
| Plant leaves | Leaf age |
| | Number of green leaves on the plant |
| | Largest green leaf: leaf length, width, and leaf area |
| | Number of leaves in each group: petiole leaf, winged leaf, and petiole-less leaf |
| Developmental stage | Sowing date, seedling emergence, seedling establishment, rosette stage, bolting and budding, initial flowering stage, ending flowering stage, seed-filling stage, maturity, and crop cycle. |
| Abiotic and biotic stresses | Number of nitrogen-deficient plants per foot, number of plants attacked by leaf miners, thrips, aphids, and any other insects, respectively. |
| Plant biomass | Fresh weight (g), dry weight (g) of roots, leaves, shoots, buds and flowers, and siliques, dependent upon growth stages. Then, biomass and partitioning of dry matter as well as nitrogen were determined. |

4.2 Seed Yield and Yield Component Analyses

Plants at maturity were windrowed first and secured in the field for drying about 8-10 days. Seeds from each plot were threshed from plants in the field and completely cleaned in a house by using a seed thresher (Washington State University, Pullman, Wash.) and a seed blower (Seedburo Equipment, Chicago, Ill. ), respectively. Actual plant density and harvest area for each plot were measured at post-harvest. Seed moisture (%) was assayed by oven drying 30-gram bulk seeds to constant weight at 105±2° C. for 8 hrs. It calculated as ($W_1$-$W_2$)/$W_1$×100, where $W_1$ was seed weight before drying (30 grams) and $W_2$ seed weight after oven drying. Final seed yield and 1000-seed weight of all trial plots for treatment comparisons and statistical analyses were adjusted at seed moisture of 8%.

Before windrowing plots at harvest, one-foot plants were selected at random from each of the inner two rows. All plants within sampled one foot were carefully dug out and transported into a house for air drying. Based on two 1-ft samples from each plot, the seed yield components were determined.

They included number of plants per foot, number of primary branches per plant, number of secondary branches per plant, number of siliques on main raceme, number of siliques on primary branches, number of siliques on secondary branches, number of seeds per silique. In addition, some traits of agronomical importance, such as plant height (cm), height to the first productive primary branch (cm), length of the main raceme, and thickness of the silique-setting layer (cm) were determined as well.

4.3 Chemical Assays for Plant and Soil Samples

According to AOAC (1995) methods, samples from plant tissues were analyzed to determine contents of total nitrogen (%) and nitrate-N (ppm), respectively. Soil of each plot from Block 5s was periodically sampled at different growth stages at three depths: 0-12", 12-24", and 24-36". For all trial plots, the bulk soil from 0-36" was sampled before the experimental onset and at the end of experiments. All soil samples were assayed to determine total nitrogen (%), nitrate nitrogen (ppm), ammonium nitrogen (ppm), available nitrogen (ppm), and organic nitrogen. In addition, bulk seeds from each plot will be analyzed for oil content and fatty acid composition by using the 5508 method (ISO, 1990).

5. Statistical Analyses

All data were analyzed using the analysis of variance (ANOVA) procedures for split-plot experimental design, as described in Table 3, to identify genotypic differences in responses to different levels of nitrogen supplied in the form of ammonium nitrate and in the form of urea. Wherever differences were observed, the L.S.D. (least significant difference) between treatment levels would be calculated for comparison of experimental effects at the 5% level. Linear or non-linear regression analyses between two variables were made by employing the least square-sum technique to reveal the minimal, optimal, and cost-effective points of nitrogen additions for different genotypes.

TABLE 3

Analysis of variance (ANOVA) outline of field trials for NUE-transgenic canola in a split-plot design.

| SOURCE OF VARIATION | | DEGREES OF FREEDOM |
|---|---|---|
| Main plots (MP) | Block | 4 |
| | Nitrogen | 3 |
| | MP error | 12 |
| Subplots (SP) | Genotype | 2 |
| | Genotype × Nitrogen | 6 |
| | SP error | 32 |
| TOTAL | | 59 |

Results

The seedlings were measured at 10 weeks for a wide range of traits intended to determine how well the plants grow in soil before the addition of fertilizers. The results are summarized below in table 4. From the table, it is clear that the non-naturally occurring plants have an enhanced growth phenotype when compared to the naturally occurring plant of the same variety. The non-naturally occurring plants are significantly larger. Thus, the non-naturally occurring plants are better able to utilize the existing nitrogen in the soil when compared to the naturally occurring variety.

TABLE 4

Seedling growth vigor before application of fertilizer

| Trait investigated | BNAT-041 | BNAT-043 | Westar | Significant Difference |
|---|---|---|---|---|
| Plant Height (cm) | 17.20 | 17.50 | 13.72 | 0.01 |
| Canopy Width (cm) | 25.57 | 19.75 | 16.07 | 0.01 |
| Leaf Age | 4.99 | 5.38 | 4.36 | 0.01 |
| Largest green leaf | | | | |
| Length (cm) | 16.93 | 15.94 | 12.32 | 0.01 |
| Width (cm) | 6.72 | 5.84 | 4.93 | 0.01 |
| Area (cm$^2$) | 115.37 | 93.67 | 60.83 | 0.01 |
| Fresh weight (g/plant) | | | | |
| Shoot | 12.04 | 9.10 | 5.19 | 0.01 |
| Root | 1.29 | 0.89 | 0.56 | 0.01 |
| Dry Weight (g/plant) | | | | |
| Shoot | 1.11 | 0.84 | 0.47 | 0.01 |
| Root | 0.16 | 0.12 | 0.07 | 0.01 |

Sample plants isolated at the flowering stage five weeks post application of nitrogen fertilizer were compared. The average biomass when the fertilizer is ammonium nitrate is indicated below in table 5 and the optimal fertilizer levels have been calculated. The optimal fertilizer levels and maximum yield when urea is the fertilizer is indicated in table 6. Both tables show that the non-naturally occurring plants produce more biomass at the maximum levels and can achieve the same biomass as a naturally occurring plant of the same variety with significantly less nitrogen fertilizer.

TABLE 5

Biomass differences between genotypes at different levels of UAN

| | Biomass Yield (g/plot dry weight) | | | |
|---|---|---|---|---|
| Nitrogen (lb/acre, UAN) | BNAT-041 | BNAT-43 | Westar | Difference |
| 0 | 2717 | 3070 | 2652 | n.s. |
| 80 | 3126 | 4527 | 2850 | p = 0.05 |
| 240 | 2284 | 7105 | 3998 | p = 0.01 |
| 400 | 4617 | 4627 | 3013 | n.s. |
| Optimal N (lb/ac) | | 233 | 232 | |
| Max Biomass Yield (g/plot) | | 6761 | 3764 | |
| UAN needed to achieve yield of 3764 g/plot (lb/ac) | | 31 | 232 | |

TABLE 6

Biomass differences between genotypes at different levels of Urea

| | BNAT-041 | BNAT-43 | Westar |
|---|---|---|---|
| Optimal N (lb/ac) | 166 | 250 | 159 |
| Max Biomass Yield (g/plot) | 4068 | 5916 | 3363 |
| Urea needed to achieve yield of 3363 g/plot (lb/ac) | 80 | 93 | 159 |

The seed yield in the plants at harvest when grown at suboptimal nitrogen supplementation (50 lb N/acre of urea) were compared. The results are shown in table 7. Table 7 clearly indicates that the non-naturally occurring plants produced significantly more seed than the naturally occurring plant of the same variety.

TABLE 7

| | Seed yield | | | |
|---|---|---|---|---|
| Yield component | BNAT-041 | BNAT-043 | Westar | Significant Difference |
| Number of plants per ft$^2$ | 3.0 | 2.4 | 3.6 | n.s. |
| Number of primary branches (PB) | 5.8 | 6.1 | 3.7 | n.s. |
| Number of secondary branches (SB) | 6.0 | 8.5 | 1.2 | p = 0.05 |
| Number of siliques on the main raceme | 36.5 | 39.5 | 33.0 | n.s. |
| Number of siliques on PB | 129.8 | 164.6 | 60.9 | p = 0.01 |
| Number of siliques on SB | 43.2 | 66.3 | 4.5 | p = 0.01 |
| Number of seeds per silique | 25.6 | 25.6 | 22.0 | n.s. |

Thus, the non-naturally occurring plants of the present invention show enhanced growth phenotypes when compared to naturally occurring plants of the same variety.

Example 7

Comparison of Different Transgenes

In this example, a number of different transgenes were tested in conjunction with a root-epidermis-specific promoter to demonstrate the broad applicability of the present invention and to demonstrate the application of the criteria that one of skill in the art would use to assess what constitutes a nitrogen utilization protein.

Materials and Methods

Vector constructs, transformation and selection of T2 homozygous lines was as described in above. The phenotype of the resulting lines were evaluated by a number of different methods. The results described below were all in vermiculite conditions.

Hydroponic conditions: Seeds were germinated in vermiculite in 6-inch pots. Fertilizer treatments began 14 days after seeding. Plants were provided with nutrients based upon Long Ashton's media (Hewitt, 1966), containing phosphorus (16 mmol), potassium (25 mmol), Mg, Ca, Fe and micronutrients. Two levels of nitrogen were applied: high nitrogen (60 mmol) and low nitrogen (20 mmol). Nitrogen was supplied as urea. Plants were harvested after 5 weeks of growth (approximately 7-leaf stage) for measurement of fresh and dry weight.

Construct: btg26/AlaDH

The enzyme alanine dehydrogenase (AlaDH) is a bacterial gene that converts ammonium ($NH_4^+$), along with pyruvate, into alanine and alpha-ketoglutarate ($\alpha$-KG). However, the reaction is energetically unfavorable, so the enzyme would be expected to lead to the breakdown of alanine and release of ammonium. In fact, the plant glutamate dehydrogenase is coupled with NADP or NADPH to drive the forward reaction, i.e., to force the generation of alanine. Thus, one would expect the reaction to run in reverse since the bacterial enzyme is not coupled with NADP.

Thus, one of skill in the art would not expect that AlaDH would be a good candidate for a nitrogen utilization protein. Testing this construct in plants confirmed this expectation, thus demonstrating that one of skill in the art would have little difficulty in determining what is and what is not a nitrogen utilization protein.

Results

The construct, btg26/AlaDH, was transformed into Westar using the *Agrobacterium* strain LBA4404 and the binary vector pCGN1547. All T0s were screened by PCR for presence of the transgene using NPTII primers. Nineteen plants were positive. The lines were evaluated for enhanced growth on low nitrogen. An analysis of the data clearly indicated that this transgene does not result in enhanced growth. In addition to the growth experiments that performed, the plants were tested for AlaDH activity, since this enzyme is not present in plants. No activity was detected. The expectation is that the plants that expressed AlaDH were not viable due to a futile cycle between the AlaDH catalyzing the release of ammonium from alanine while the plant is assimilating ammonium via the GS-GOGAT cycle at an energetic cost.

Dry Weights for Transgenic btg26AlaDH Plants Grown Hydroponically on Vermiculite

| | Dry Weight (g) | | | |
|---|---|---|---|---|
| | Shoots | | Roots | |
| Genotype | Mean | Std. Error | Mean | Std. Error |
| Westar | 16.52 | 1.36 | 5.08 | 0.32 |
| btg26/AlaAT | 21.51 | 3.65 | 6.78 | 0.93 |
| Line 26 | 23.00 | 7.38 | 5.83 | 0.56 |
| Line 32c* | 3.05 | 0.45 | 2.27 | 0.12 |
| Line 38 | 13.68 | 2.91 | 3.99 | 0.45 |
| Line 16b | 3.27 | 0.63 | 2.36 | 0.16 |

Construct: btg26/AspAT

The enzyme aspartate aminotransferase (AspAT) catalyzes the conversion of glutamate, along with oxaloacetate, into aspartate and $\alpha$-KG.

It is an important enzyme in the downstream events of incorporating organic nitrogen into the plant. The aspartate produced represents a pool of stored nitrogen that is the precursor to five other amino acids and ureides (urea like compounds) that are transportable nitrogen-containing compounds. This transamination reaction completes the process of bringing nitrogen into the plant and converting it to a readily usable form. By combining this enzyme with the root specific, inducible promoter, btg26, one of skill in the art would expect enhanced growth on low nitrogen. Thus the protein was a good candidate for a nitrogen utilization protein.

Results

Figure 19:
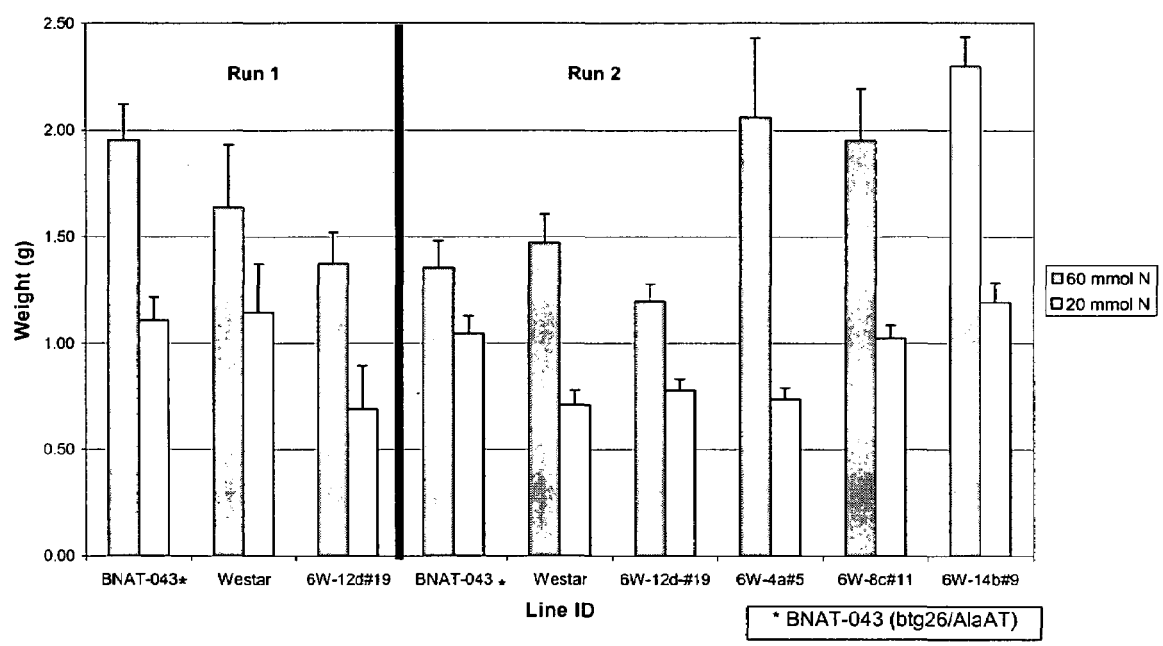
FIG. 19: Average shoot weight of control canola (westar) and transgenic lines transformed with btg-26/AlaAT (BNAT-043) or btg-26/AspAT (6W lines).
Figure 20:
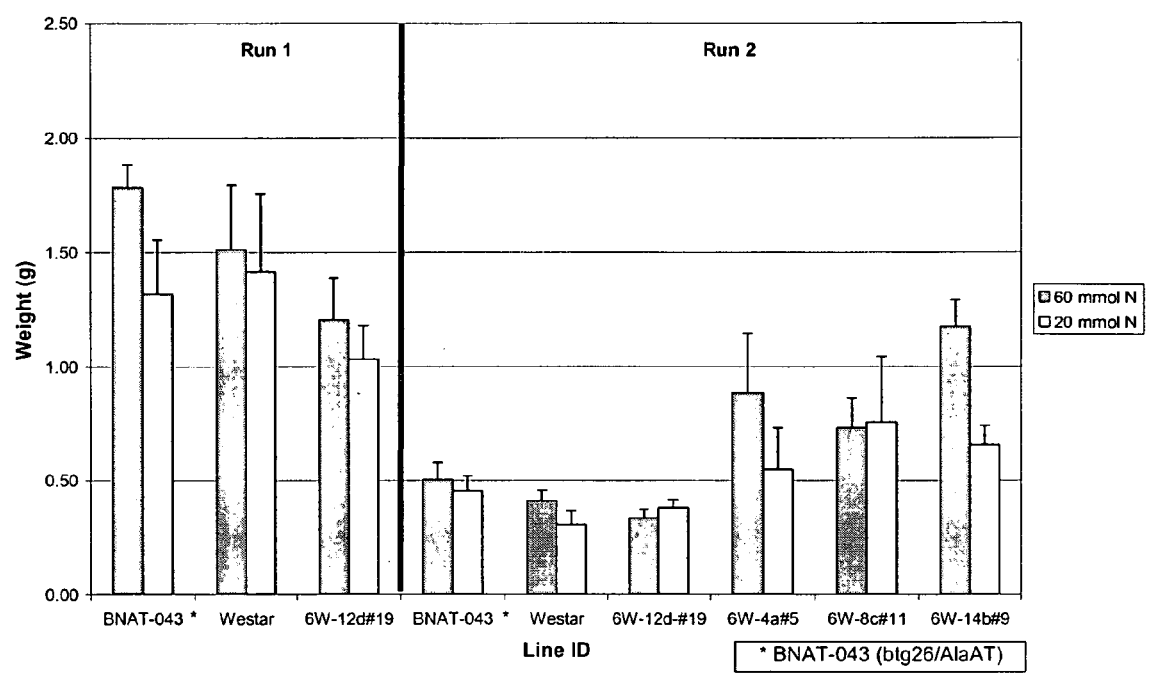
FIG. 20: Average root weight of control canola (westar) and transgenic lines transformed with btg-26/AlaAT (BNAT-043) or btg-26/AspAT (6W lines).

*Brassica napus* cv. N01 and cv. Q2 were transformed with the *Agrobacterium* strain LBA4404 using the pCGN1547 binary vector containing the btg26/AspAT construct. Forty-six transgenic N01 lines and 2 transgenic Q2 lines were produced. All T0s were screened by PCR for presence of the transgene using NPTII primers. All positive plants (39 lines of N01 and 2 lines of Q2) were selfed and T1 seed collected. FIGS. 19 and 20 indicate that the btg26/AspAT transgenic lines outperformed the controls under vermiculite conditions. Thus, as expected AspAT is a nitrogen utilization protein as defined hereunder.

Example 8

Comparison of Different Promoters

In this example, a number of different promoters were tested in conjunction with a nitrogen utilization protein to demonstrate the necessity of the tissue specificity of the promoter in the present invention.

Construct: nr2/AlaAT

As demonstrated in previous Examples, the AlaAT protein is a nitrogen utilization protein. The nitrate reductase (nr2) promoter is induced by nitrate and is root specific, but not root epidermis specific.

Results

Plant transformations were performed on *Brassica napus* cv. N01 and cv. Q2 using the *Agrobacterium* strain LBA4404 and the binary vector pCGN1547, containing the construct nr2/AlaAT. Fifty-six independent lines were produced which were screened for presence of the transgene using NPTII primers. Of the 56 lines, 46 were positive for presence of the transgene and were subsequently selfed and T1 seed collected.

| Total N—P—K per plant: | | |
|---|---|---|
| Nitrogen: | High Nitrogen Treatment | 56 mmol |
| | Low Nitrogen Treatment | 10.71 mmol |
| Phosphorous: | | 16.44 mmol |
| Potassium: | | 24.84 mmol |

Figure 21A:
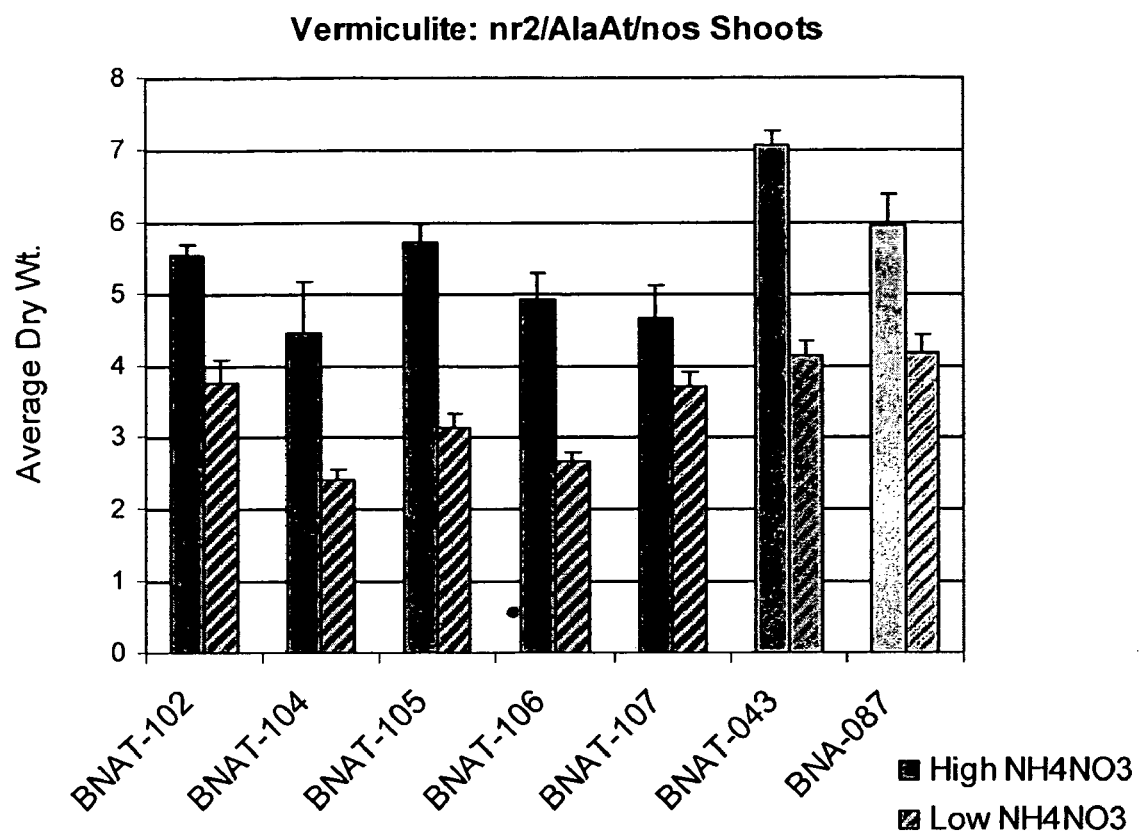
FIG. 21A: Average shoot weight of transgenic lines transformed with btg-26/AlaAT (BNAT-043 and -087) or tr/AlaAT (BNAT-102, -104, -105, -106, and -107).
Figure 21B:
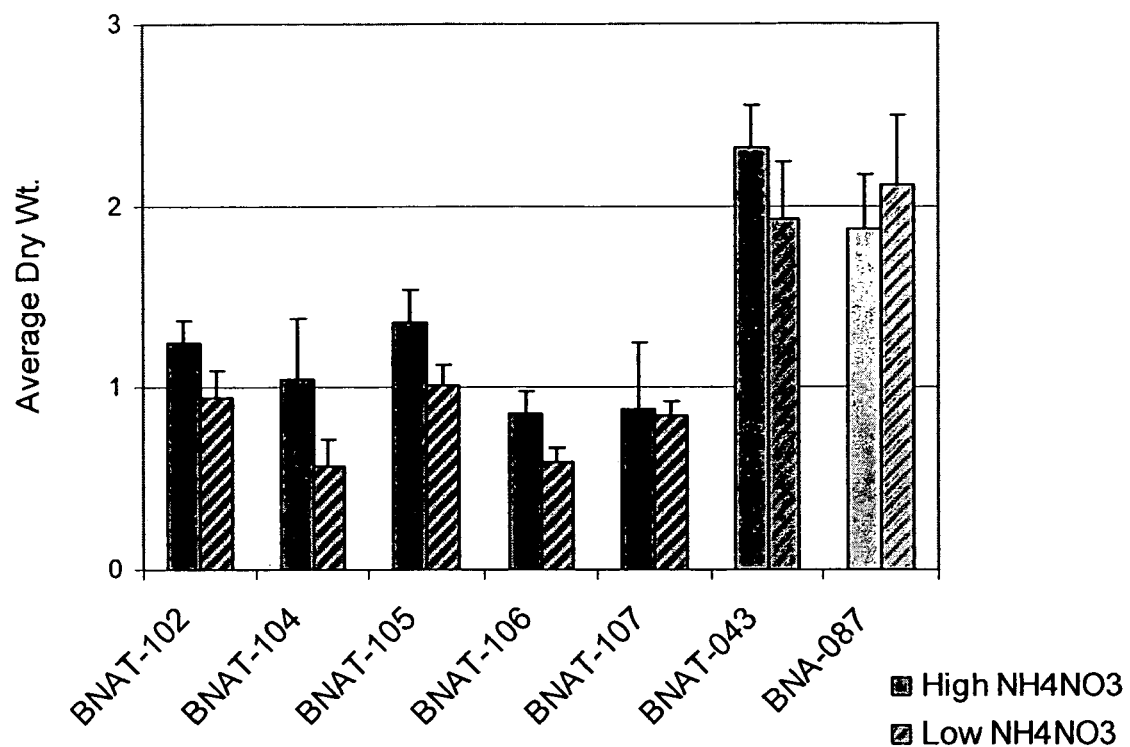
FIG. 21B: Average root weight of transgenic lines transformed with btg-26/AlaAT (BNAT-043 and -087) or tr/AlaAT (BNAT-102, -104, -105, -106, and -107).

The data for this is shown in FIG. 21. The data is from several experiments conducted separately, which were done using different nitrogen sources. The data shows that the nr2/AlaAT constructs do not appear to show any enhanced growth. This indicates that having a root specific promoter does not, in and of itself result in an enhanced growth phenotype.

Construct: Ca2/AlaAT

The Cauliflower Mosaic Virus 35S (CaMV35S) promoter is known to be constitutively expressed in all different tissues. The published reports have shown that the resulting phenotype is variable. We decided to test an additional number of lines to evaluate the increase uptake of nitrate fertilizers and increase the organic nitrogen that is available for plant growth.

Results

Plant transformations were performed on *Brassica napus* cv. N01 using the *Agrobacterium* strain LBA4404 and the binary vector pCGN1547, containing the construct CaMV/AlaAT. Independent lines were produced which were screened for presence of the transgene using NPTII primers. Growth conditions were the same as shown for nr2/AlaAT.

Figure 22:
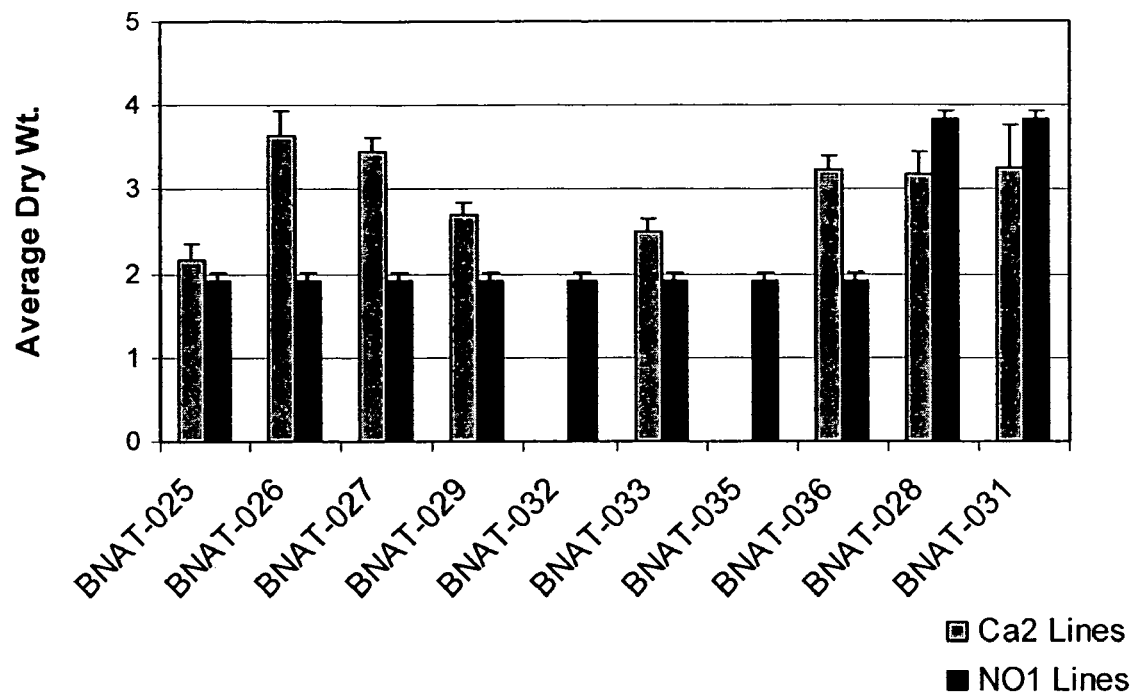
FIG. 22: Average total dry weight of transgenic lines transformed with Ca2/AlaAT compared with the negative control.

The data for this is reported in FIG. 22. The data shows several separate experiments conducted separately, which were done using different nitrogen sources. As expected, the results were variable with some lines showing enhanced growth phenotypes and others showing no enhancement of their growth.

Construct: trg31/AlaAT

The trg31 promoter is known to be stress induced and a detailed analysis of its expression shows that it is expressed in all different tissues. In particular, it is highly expressed in the vascular tissue of plants, including root vascular tissue. The resulting transgenic plants were evaluated in terms of their increase in uptake of nitrate fertilizers and increase the organic nitrogen that is available for plant growth.

Results

Plant transformations were performed on *Brassica napus* cv. N01 using the *Agrobacterium* strain LBA4404 and the binary vector pCGN1547, containing the construct CaMV/AlaAT. Independent lines were produced which were screened for presence of the transgene using NPTII primers. Growth conditions were the same as shown for nr2/AlaAT.

Figure 23:
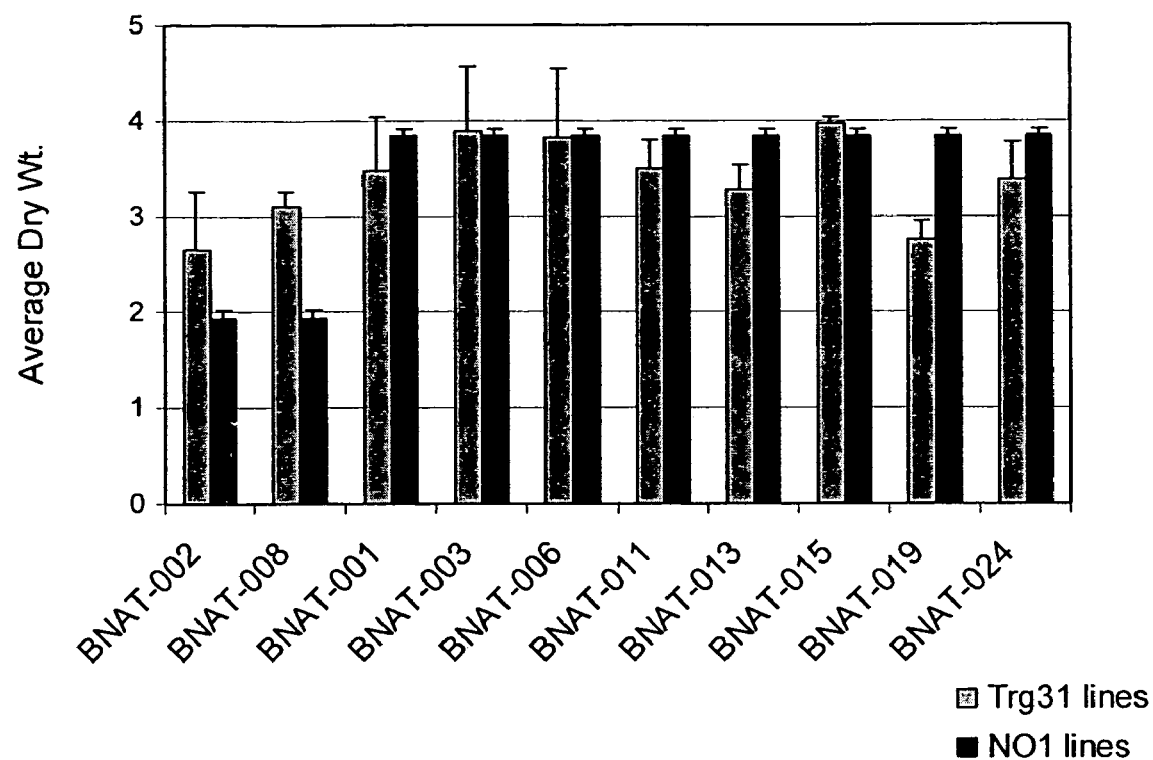
FIG. 23: Average total dry weight of transgenic lines transformed with Trg31/AlaAT compared with the negative control.

The data for this is shown in FIG. 23. Data shown is from experiments conducted separately. Although both lines all show enhanced growth in experiment 1, none of the lines showed an increase in growth under non-optimal condition in any subsequent experiments. This indicates that having a stress inducible promoter does not, in and of itself result in an enhanced growth phenotype. In addition, expression in the vascular tissue of roots does not result in an enhanced growth phenotype.

REFERENCES

Amarashinghe B H R R, et al., (1998) Planta 206:44-52,
Becker T, et al., (1992) Plant Mol. Biol. 19:367-379
Bock B R (1984) In. Nitrogen in Crop Production pp. 273-294.,
Borlaug N E (2000) Plant Physiol. 124:487-490
Brownlee A, and Arst H J (1983) J Bacteriol 155:1136-1146
Caboche M, and Rouze P (1990) Trends Genet 6:187-192
Campbell W H (1999) Ann. Rev. Plant Physiol. and Plant Mol. Biol. 50:277-303
Carpenter S R, et al., (1995) Science 269:324-327
Cheng C-L, et al., (1986) PNAS USA 83:6825-6828
Cheng C-L, et al., (1988) EMBO J 7:3309-3314
Cheng C-L, et al., (1991) Plant Physiol. 96:275-279
Crawford N M, et al., (1988) PNAS USA 85:5006-5010
Crawford N M, and Glass A D M (1998) Trends in Plant Sci. 3:389-395
Coruzzi G, and Last R (2000) Amino Acids. In Biochemistry and Molecular Biology of Plants
Cotelle V, et al., (2000) EMBO J. 19:2869-76
Deng M D, et al., (1989) Physiol. Plant. 91:304-309
Deng M D, et al., (1991) Plant Physiol. Biochem. 29:239-247
Downs C G et al., (1994) Plant Cell Environ. 17:1045-1052
Dubois F, et al., (1996 Plant Mol. Biol. 31:803-817
Eckes P, et al., (1989) Mol. Gen. Genet. 217: 263-268
FAO yearbook (1996) Fertilizer. Vol. 46. FAO statistics series No. 136.
Henon P, et al., (1990) Plant Mol. Biol. 15: 895-904
Finnemann J. and Schoerring J K (1999) Physiol. Plant. 105: 469-477
Finnemann J, and Schoerring J K (2000) Plant J. 24:171-181
Fraisier V, et al., (2000) Plant J. 23:489-495
Forde B G (2000) 1465:219-235
Fukuoka H, et al., (1996) Plant Physiol. 111:39-47
Guerrero M, et al., (1981) Ann Rev Plant Physiol 32:169-204
Goulding K W T, et al., (1998) New Pytologist. 139:49-58
Hirel B, et al., (1992) Plant Mol. Biol. 20:207-218
Howitt S M, and Udvardi M K, (2000) BBA Biomembranes. 1465:152-170
Johnston I L, et al., (1990) Gene 90: 181-192
Lam H M, et al., (1996) Annual Review of Plant Physiol. and Mol. Biol. 47:569-593
Lappartient A, et al., (1999) Plant J. 18: 89-95
Lejay L, et al., (1999) Plant J. 18:509-519
Lea P, et al., (1990). In Methods in plant biochemistry. Academic Press, New York, pp 257-276
Lightfoot D A, et al., (1988) Plant Mol. Biol. 11:191-202-427
Limami A, et al., (1999) Planta. 209: 495-502
Matson P A, (1998) Science 280:112-114
Migge A, et al., (2000) Planta. 210:252-260
Mitchell A P (1985) Genetics 111:243-258
Moorhead G, et al., (1996) Curr. Biol. 6:1104-1113
Moorhead G, et al., (1999) Plant J. 18:1-12
Ninnemann O, et al., (1994) EMBO J. 13:3464-3471

Oaks, A. (1994) Can. J. Bot. 72: 739-750
Peterman T, and Goodman H (1991) Mol. Gen. Genet. 230: 145-154
Porter P M (1993) J. Plant Nutr. 16:2371-2381
Sohlenkamp C, et al., (2000) FEBS lett. 467:273-278
Su, W. et al., (1996) The Plant Cell 8:519-527.
Tilman D. (1999) PNAS. 96:5995-6000
Tingey S, et al., (1988) J. Biol. Chem. 263:9651-9657
Tingey S, et al., (1987) EMBO J. 6:1-9
Tsay Y-F, et al., (1993) Cell 72:705-713
Unkles S E, et al., (1991). PNAS USA 88:204-208
Vance C P(1997) The molecular biology of N metabolism. In *Plant Metabolism* 2$^{nd}$ *edition*. 449-477
Vidmar J J, et al., (1999) Plant Mol. Biol. 40: 883-892
Vidmar J J, et al., (2000a) Plant Physiol. 122:783-792
Vidmar J J, et al., (2000b) Plant Physiol. 123:307-318
Vidmar J J, et al., (2000c) FEBS lett. 475: 65-69
Vincent R, et al., (1997) Planta 201:424-433
Vincentz M, and Caboche M (1991) EMBO J. 10:1027-1035
Vincentz M, et al., (1993) Plant J. 3:315-324
Weiner H, and Kaiser W M (1999) FEBS Lett. 455:75-78
Yaffe M B, et al., (1997) Cell. 91:961-71
Zhou D, et al., (1999). Plant J. 17:563-569
Zhou J J, et al.,(2000) J. Biol. Chem. 275: 39894-39899

Incorporation by Reference

All patents, published patent applications and other references disclosed herein are hereby expressly incorporated herein in their entireties by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A transgenic plant comprising elevated levels of barley alanine aminotransferase in the root epidermis, wherein said transgenic plant comprises a transgene, wherein said transgene comprises SEQ ID NO: 2 operably linked to SEQ ID NO: 1.

2. A seed of said transgenic plant of claim 1, comprising said transgene.

3. A method of producing the plant according to claim 1, comprising
providing an expression vector, wherein said expression vector comprises SEQ ID NO: 2 operably linked to SEQ ID NO: 1;
introducing said expression vector into a plant cell; and
producing said plant from said plant cell.

4. A method for preferentially producing alanine aminotransferase in the root epidermis of a plant, comprising
operatively linking a nucleic acid encoding alanine aminotransferase to SEQ ID NO: 1 to form a construct;
introducing said construct into a plant cell;
producing a plant from said plant cell, wherein said plant comprises a root epidermis; and
expressing said construct in said plant to preferentially produce alanine aminotransferase in said root epidermis of said plant.

5. The method of claim 4, wherein said plant is selected from the group consisting of corn, wheat, rice, barley, canola, soybean, cotton, alfalfa, safflower, tomato and potato.

6. The method of claim 4, wherein said plant is canola.

7. The method of claim 4, wherein said plant is corn.

8. The method of claim 4, wherein said plant is wheat.

9. The method of claim 4, wherein said alanine aminotransferase is barley alanine aminotransferase.

10. The method of claim 9, wherein said barley alanine aminotransferase nucleic acid has the nucleotide sequence of SEQ ID NO: 2.

11. A method for increasing nitrogen use efficiency of a plant, comprising
operatively linking a nucleic acid encoding alanine aminotransferase to a root epidermis promoter to form a construct;
introducing said construct into a plant cell;
producing a plant from said plant cell, wherein said plant comprises a root epidermis; and
expressing said construct in said plant to produce elevated levels of alanine aminotransferase preferentially in said root epidermis in order to increase nitrogen use efficiency of said plant.

12. The method of claim 11, wherein said root epidermis promoter has the nucleotide sequence of SEQ ID NO: 1.

13. The method of claim 11, wherein said plant is a canola plant.

14. The method of claim 11, wherein said alanine aminotransferase is barley alanine aminotransferase.

15. The method of claim 14, wherein said barley alanine aminotransferase nucleic acid has a nucleotide sequence of SEQ ID NO: 2.

16. A method for increasing biomass of a plant, comprising
operatively linking a nucleic acid encoding alanine aminotransferase to a root epidermis promoter to form a construct;
introducing said construct into a plant cell;
producing a plant from said plant cell, wherein said plant comprises a root epidermis; and expressing said construct in said plant to produce elevated levels of alanine aminotransferase preferentially in said root epidermis in order to increase biomass of said plant.

17. The method of claim 16, wherein plant is a canola plant.

18. The method of claim 16, wherein said root epidermis promoter has the nucleotide sequence of SEQ ID NO: 1.

19. The method of claim 16, wherein said alanine aminotransferase is barley alanine aminotransferase.

20. The method of claim 19, wherein said barley alanine amino transferase nucleic acid has the nucleotide sequence of SEQ ID NO: 2.

* * * * *